United States Patent
Shanechi

(10) Patent No.: US 12,097,029 B1
(45) Date of Patent: Sep. 24, 2024

(54) DECODING NEUROPSYCHIATRIC STATES FROM MULTI-SITE BRAIN NETWORK ACTIVITY

(71) Applicant: University of Southern California, Los Angeles, CA (US)

(72) Inventor: Maryam Shanechi, Los Angeles, CA (US)

(73) Assignee: UNIVERSITY OF SOUTHERN CALIFORNIA, Los Angeles, CA (US)

(*) Notice: Subject to any disclaimer, the term of this patent is extended or adjusted under 35 U.S.C. 154(b) by 1347 days.

(21) Appl. No.: 16/031,925

(22) Filed: Jul. 10, 2018

Related U.S. Application Data

(60) Provisional application No. 62/530,790, filed on Jul. 10, 2017, provisional application No. 62/530,690, filed on Jul. 10, 2017.

(51) Int. Cl.
*A61B 5/16* (2006.01)
*A61B 5/00* (2006.01)
(Continued)

(52) U.S. Cl.
CPC ............... *A61B 5/165* (2013.01); *A61B 5/16* (2013.01); *A61B 5/316* (2021.01); *A61B 5/369* (2021.01);
(Continued)

(58) Field of Classification Search
None
See application file for complete search history.

(56) References Cited

U.S. PATENT DOCUMENTS

| | | | | |
|---|---|---|---|---|
| 2010/0145176 A1* | 6/2010 | Himes | ............... | A61B 5/0002 600/545 |
| 2011/0301431 A1* | 12/2011 | Greicius | ............ | G01R 33/4806 600/300 |

(Continued)

OTHER PUBLICATIONS

Fell, Juergen. Identifying neural correlates of consciousness: The state space approach. Conscious Cogn. Dec. 2004; 13(4):709-29. (Year: 2004).*

(Continued)

*Primary Examiner* — Meredith Weare
(74) *Attorney, Agent, or Firm* — Snell & Wilmer LLP

(57) ABSTRACT

A method for decoding mood or other neuropsychiatric states from large-scale brain activity includes receiving, by a processor, large-scale brain activity signals from an electrode assembly coupled to a subject. The method includes continuously and automatically decoding a neuropsychiatric state of the subject from the large-scale brain activity signals received from a predictive network subset of brain sites coupled to the electrode assembly, contemporaneously with the receiving. The method includes providing a signal indicative of the neuropsychiatric state. A method for adaptive tracking of large-scale brain network activity includes characterizing, by one or more computers, a time-variant linear state-space model predictive of a brain state, at least in part by updating estimates of time-varying covariance matrices at time steps. The method includes tracking large-scale brain network activity in a subject using an electrode array and continuously and automatically estimating the subject's brain state contemporaneously with the characterizing and tracking.

41 Claims, 37 Drawing Sheets

(51) Int. Cl.
*A61B 5/316* (2021.01)
*A61B 5/369* (2021.01)
*G16H 50/20* (2018.01)

(52) U.S. Cl.
CPC .......... *A61B 5/4803* (2013.01); *A61B 5/7267* (2013.01); *G16H 50/20* (2018.01)

(56) References Cited

U.S. PATENT DOCUMENTS

| | | | |
|---|---|---|---|
| 2013/0184558 A1* | 7/2013 | Gallant | A61B 5/316 600/409 |
| 2014/0148657 A1* | 5/2014 | Hendler | A61B 5/291 600/545 |
| 2014/0236039 A1* | 8/2014 | Strokova Aksenova | A61B 5/369 600/544 |
| 2016/0242690 A1* | 8/2016 | Principe | A61B 5/316 |
| 2017/0043167 A1* | 2/2017 | Widge | A61B 5/4836 |
| 2017/0202475 A1* | 7/2017 | Leuthardt | A61B 5/316 |
| 2018/0039328 A1* | 2/2018 | Malik | A61B 5/377 |

OTHER PUBLICATIONS

Ho et al. "A state-space approach to modelling brain dynamics." Apr. 2005. Statistica Sinica 15(2):407-425. (Year: 2005).*

Wu et al. "Neural Decoding of Hand Motion Using a Linear State-Space Model With Hidden States." IEEE Trans Neural Syst Rehabil Eng. Aug. 2009;17(4):370-8. (Year: 2009).*

Stamoulis et al. Estimation of Brain State Changes Associated with Behavior, Stimulation and Epilepsy. Annu Int Conf IEEE Eng Med Biol Soc. 2009; 2009: 4719-22. (Year: 2009).*

Goshvarpour et al. "Modeling Epileptic EEG Time Series by State Space Model and Kalman Filtering Algorithm." Feb. 2014. International Journal of Intelligent Systems and Applications 6(3):26-34. (Year: 2014).*

Breakspear, Michael. "Dynamic models of large-scale brain activity." Nature Neuroscience vol. 20, pp. 340-352 (2017). (Year: 2017).*

Sani et al. "Mood variations decoded from multi-site intracranial human brain activity." Nature Biotechnology vol. 36, pp. 954-961 (2018). (Year: 2018).*

Montgomery, D.C., Peck, E.A. and Vining, G.G. (2012) Introduction to Linear Regression Analysis. vol. 821, John Wiley & Sons, Hoboken. (Year: 2012).*

* cited by examiner

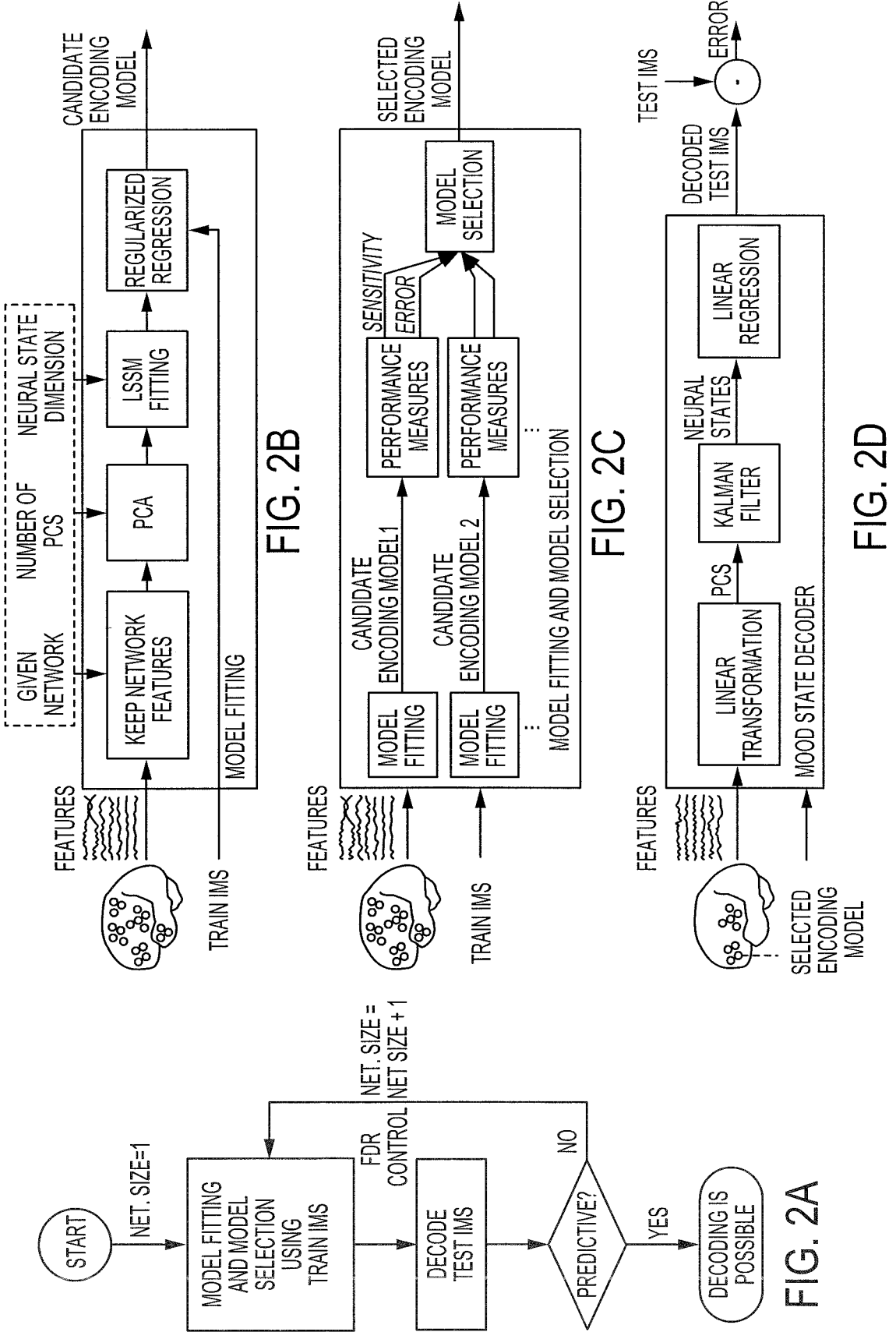

| SUBJECT | NRMSE ×100% | P VALUE [FDR-CORRECTED IF DIFFERENT] | | REGIONS IN MOOD-PREDICTIVE NETWORK |
|---|---|---|---|---|
| | | RANDOM-TEST | PERMUTED-TEST | |
| EC79 | 78.5% | 0.047 | 0.042 | OFC |
| EC82 | 35.1% | 0.00011 | 0.00013 | OFC |
| EC87 | 56.0% | 0.0088 [0.035] | 0.012 [0.050] | OFC, dACC, vACC |
| EC108 | 51.5% | 0.0058 | 0.0059 | AMYG |
| EC137 | 72.8% | 0.0092 [0.037] | 0.0075 [0.030] | dACC, HPC, sFG, mFG |
| EC150 | 78.5% | 0.035 | 0.045 | HPC |
| EC166 | 40.3% | 0.00042 | 0.0027 | OFC |
| POPULATION | 68.3% | $3.8 \times 10^{-12}$ | $1.1 \times 10^{-15}$ | - |

ABBREVIATIONS: OFC: ORBITOFRONTAL CORTEX, dACC: DORSAL ANTERIOR CINGULATE CORTEX, vACC: VENTRAL ANTERIOR CINGULATE CORTEX, AMYG: AMYGDALA, sFG: SUPERIOR FRONTAL GYRUS, mFG: MIDDLE FRONTAL GYRUS, HPC: HIPPOCAMPUS.

FIG. 8

| SUBJECT | GENDER | AGE | IMPLANT DURATION [DAYS] | SEIZURE FOCI | PATHOLOGICAL FINDINGS |
|---|---|---|---|---|---|
| EC79 | F | 47 | 8 | AMYG, TC | MILD GLIOSIS IN RIGHT LATERAL TEMPORAL LOBE |
| EC82 | M | 65 | 20 | HPC | MILD LEFT HIPPOCAMPAL SCLEROSIS |
| EC87 | F | 53 | 8 | OFC, vACC, FC | CHRONIC INFLAMMATION IN RIGHT FRONTAL LOBE |
| EC108 | F | 20 | 8 | HPC, TC | FOCAL CORTICAL DYSPLASIA IN LEFT LATERAL TEMPORAL LOBE |
| EC137 | M | 20 | 22 | - | - |
| EC150 | F | 40 | 8 | RIGHT AMYG AND HPC | - |
| EC166 | F | 34 | 8 | HPC | RIGHT HIPPOCAMPAL SCLEROSIS |

FIG. 20

| QUESTION | NEGATIVE MOOD STATE DESCRIPTOR | POSITIVE MOOD STATE DESCRIPTOR |
|---|---|---|
| 1 | DEPRESSED | HAPPY |
| 2 | DISTRACTED | FOCUSED |
| 3 | WORTHLESS | VALUABLE |
| 4 | LONELY | ENGAGED |
| 5 | SLEEPY | ALERT |
| 6 | SLOW | SPEEDY |
| 7 | TIRED | ENERGETIC |
| 8 | PESSIMISTIC | OPTIMISTIC |
| 9 | APATHETIC | MOTIVATED |
| 10 | GUILTY | PROUD |
| 11 | NUMB | INTERESTED |
| 12 | WITHDRAWN | WELCOMING |
| 13 | FRUSTRATED | PEACEFUL |
| 14 | IMPULSIVE | CAREFUL |
| 15 | MOODY | STABLE |
| 16 | HOPELESS | HOPEFUL |
| 17 | IRRITABLE | EASY-GOING |
| 18 | TENSE | RELAXED |
| 19 | WORRIED | UNTROUBLED |
| 20 | FEARFUL | FEARLESS |
| 21 | ANXIOUS | PEACEFUL |
| 22 | RESTLESS | CALM |
| 23 | EASILY ANNOYED | CALM |
| 24 | STUCK ON NEGATIVE THOUGHTS | ENGAGED IN POSITIVE THOUGHTS |

FIG. 21

| SUBJECT | NUMBER OF IMS POINTS | IMS VARIATIONS | | | IMS RANGE RELATIVE TO TOTAL POSSIBLE RANGE [%] | TIME DIFFERENCE BETWEEN CONSECUTIVE IMS POINTS [HOURS] | | | TIME DIFFERENCE BETWEEN FIRST AND LAST IMS POINTS |
|---|---|---|---|---|---|---|---|---|---|
| | | MIN | MAX | RANGE | | MIN | MAX | MEDIAN | |
| EC79* | 11 | -9 | +25 | 34 | 25% | 1.3 | 28 | 17 | 5.7 DAYS |
| EC82 | 16 | -40 | -4 | 36 | 25% | 1 | 11.5 | 3.5 | 3.0 DAYS |
| EC87 | 10 | -24 | +18 | 42 | 29% | 0.5 | 23 | 0.5 | 3.0 DAYS |
| EC108 | 10 | -10 | +50 | 60 | 42% | 2.5 | 48 | 8 | 4.7 DAYS |
| EC137 | 15 | -48 | +11 | 59 | 41% | 3.5 | 71 | 22 | 16.0 DAYS |
| EC150 | 12 | -6 | +42 | 48 | 33% | 1.5 | 42 | 4 | 4.5 DAYS |
| EC166 | 13 | +2 | +57 | 55 | 38% | 2 | 22 | 8 | 5.0 DAYS |

* THIS SUBJECT FILLED A 23-ITEM IMS QUESTIONNAIRE RESULTING IN A TOTAL POSSIBLE RANGE OF -69 TO +69.

FIG. 22

| SUBJECT | NRMSE [%] | P VALUE [FDR-CORRECTED IF DIFFERENT] | |
|---|---|---|---|
| | | RANDOM-TEST | PERMUTED-TEST |
| EC79* | - | - | - |
| EC82 | 61.9% | 0.0047 [0.0094] | 0.0045 [0.0090] |
| EC87 | 70.6% | 0.022 [0.065] | 0.034 [0.10] |
| EC108 | 50.2% | 0.018 [0.054] | 0.02 [0.03] |
| EC137 | 81.7% | 0.0088 | 0.031 |
| EC150 | 48.9% | 3.2×10⁻⁸ [9.7×10⁻⁸] | 5.4×10⁻⁶ [1.6×10⁻⁵] |
| EC166 | 71.5% | 0.039 | 0.0086 |

*A ROBUST COHERENCE-BASED DECODER WAS NOT FOUND FOR THIS SUBJECT.

FIG. 23

| SUBJECT | HEMI-SPHERE | TOTAL NUMBER OF CHANNELS | COVERAGE WITHIN THE LIMBIC REGIONS* | | COVERAGE OUTSIDE THE LIMBIC REGIONS | |
|---|---|---|---|---|---|---|
| | | | REGION (NUMBER OF INTRACRANIAL ELECTRODES IN REGION) | NUMBER OF VERIFIED CHANNELS | REGION (NUMBER OF INTRACRANIAL ELECTRODES IN REGION) | NUMBER OF CHANNELS |
| EC79 | RIGHT | 16 | OFC (1), dACC (1), HPC (1) | 7 | ITC (3), PUT (1) | 8 |
| EC82 | LEFT | 35 | OFC (2), HPC (2) | 15 | TC (1), ITC (3), FC (1) | 20 |
| EC87 | RIGHT | 62 | OFC (2), dACC (3), vACC (1) | 20 | PC (1), TC (1), FP (1), FC (3) | 36 |
| EC108 | LEFT | 70 | OFC (1), dACC (1), AMYG (1), HPC (1), INS (1) | 41 | TC (2), ITC (2) | 19 |
| EC137 | RIGHT | 26 | OFC (1), dACC (1), AMYG (1), HPC (1) | 12 | TC (1), FC (1) | 8 |
| EC150 | STEREO | 49 | OFC (2), dACC (3), AMYG (2), HPC (2), INS (3) | 39 | - | - |
| EC166 | RIGHT | 56 | OFC (2), dACC (1), vACC (1), AMYG (1), HPC (1), INS (1) | 21 | TC (1), ITC (4) | 24 |

*NOTE THAT THERE WERE SOME RECORDING CHANNELS IN THESE ELECTRODES THAT WERE NOT VERIFIED TO BE IN THE LIMBIC REGIONS, E.G., 10 CHANNELS IN EC150 (10 = COLUMN 3 - COLUMN 5 - COLUMN 7). THESE CHANNELS WERE NOT INCLUDED IN THE LIMBIC SEARCH (SEE METHODS) AND ARE NOT COUNTED UNDER COLUMN 5 "NUMBER OF VERIFIED CHANNELS".

FIG. 24

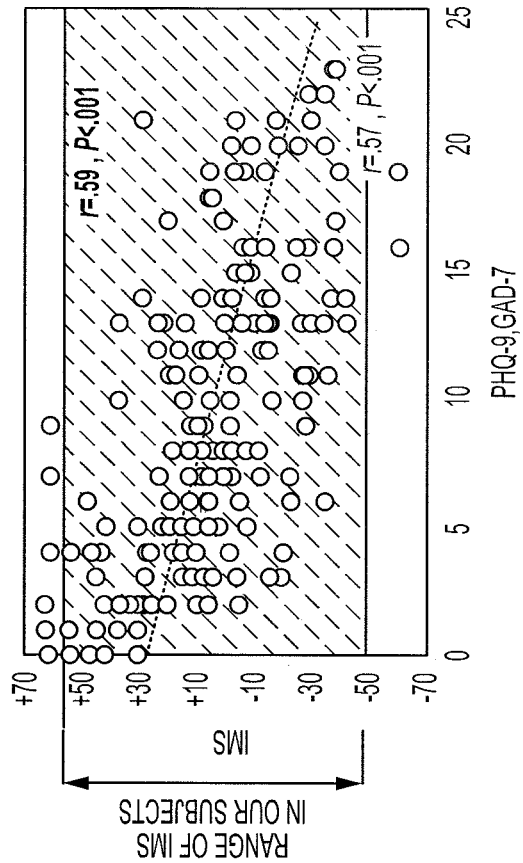
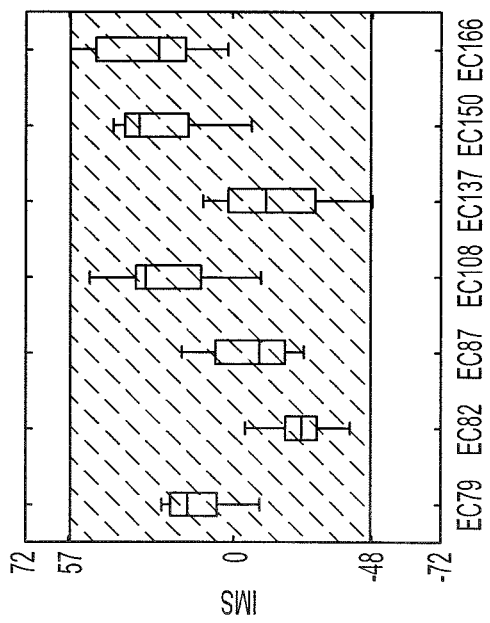
FIG. 25A
FIG. 25B

| SUBJECT | TOTAL NUMBER OF FEATURES | NUMBER OF FEATURES IN THE SELECTED NETWORK | NUMBER OF RETAINED PCS (EXPLAINED VARIANCE [%]) | NEURAL STATE DIMENSION | EFFECTIVE NUMBER OF REGRESSION PARAMETERS | NUMBER OF IMS POINTS |
|---|---|---|---|---|---|---|
| EC79 | 35 | 20 | 5 (95.5%) | 6 | 3.69 | 11 |
| EC82 | 75 | 20 | 15 (99.1%) | 6 | 6.83 | 16 |
| EC87 | 100 | 70 | 15 (95.2%) | 9 | 5.38 | 10 |
| EC108 | 205 | 20 | 5 (94.3%) | 3 | 3.93 | 10 |
| EC137 | 130 | 60 | 5 (86.4%) | 9 | 6.16 | 15 |
| EC150 | 195 | 30 | 5 (91.2%) | 5 | 5.28 | 12 |
| EC166 | 105 | 15 | 10 (99.8%) | 6 | 6.91 | 13 |

FIG. 29

| SUBJECT | NETWORK SELECTED WHEN SEARCHING | | |
|---|---|---|---|
| | ONLY LIMBIC REGIONS | ALL REGIONS | ONLY OUTSIDE LIMBIC REGIONS |
| EC79 | OFC | - | - |
| EC82 | OFC | OFC | - |
| EC87 | OFC, vACC, dACC | OFC, vACC, dACC, FC, PC, TC | - |
| EC108 | AMYG | AMYG | ITC |
| EC137 | - | sFG, mFG, dACC, HPC | - |
| EC150 | HPC | HPC | - |
| EC166 | OFC | OFC | ITC |

FIG. 30A

| ABBREVIATIONS | ANATOMICAL REGION |
|---|---|
| OFC | ORBITOFRONTAL CORTEX |
| ACC | ANTERIOR CINGULATE CORTEX |
| dACC | DORSAL ACC |
| vACC | VENTRAL ACC |
| AMYG | AMYGDALA |
| HPC | HIPPOCAMPUS |
| INS | INSULA |
| FC | FRONTAL CORTEX |
| sFG | SUPERIOR FRONTAL GYRUS |
| mFG | MIDDLE FRONTAL GYRUS |
| FP | FRONTAL POLE |
| TC | TEMPORAL CORTEX |
| ITC | INFERIOR TEMPORAL CORTEX |
| PUT | PUTAMEN |
| PC | PARIETAL CORTEX |

FIG. 30B

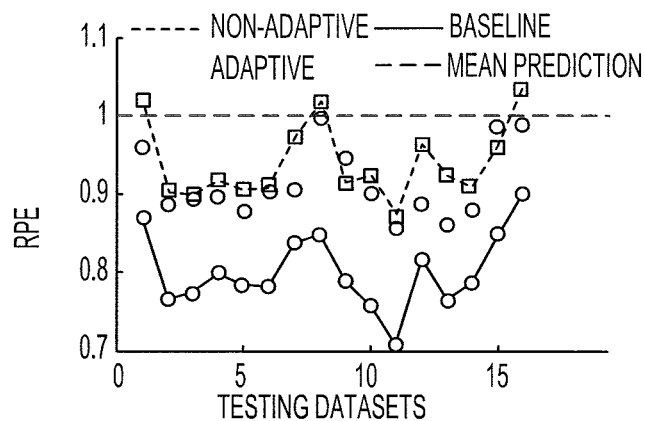 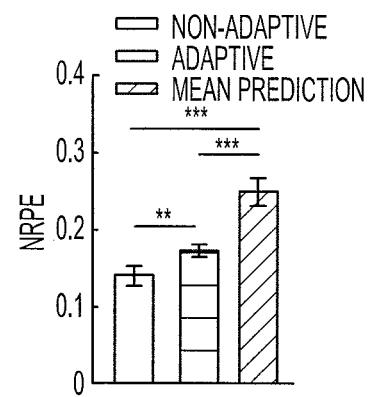
FIG. 34A  FIG. 34B
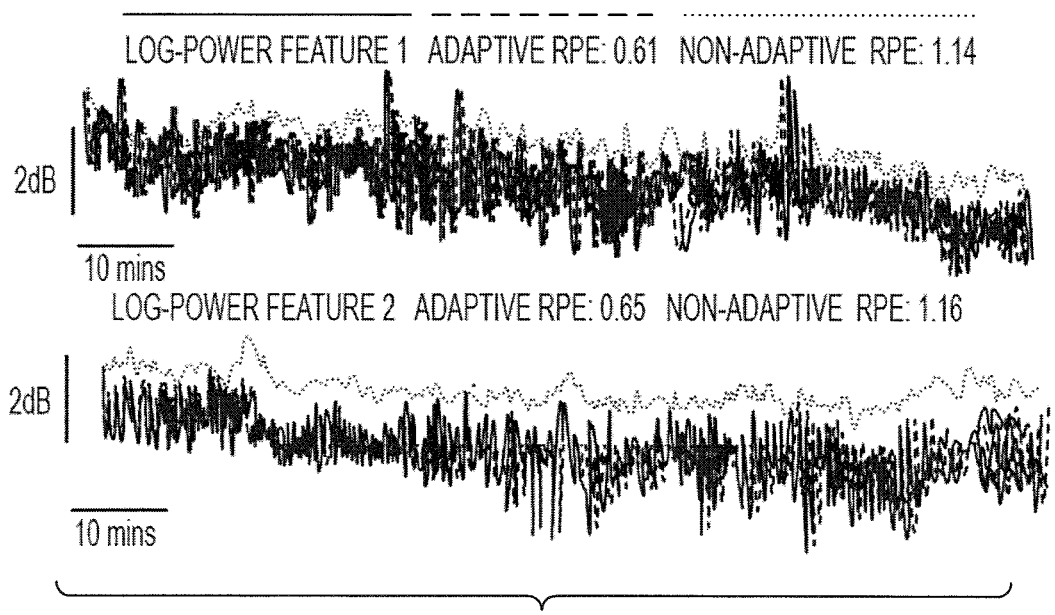
FIG. 34C

100
DECODING NEUROPSYCHIATRIC STATES FROM MULTI-SITE BRAIN NETWORK ACTIVITY

CROSS-REFERENCE TO RELATED APPLICATIONS

This application claims the benefit and priority of U.S. Provisional Application No. 62/530,690, entitled "ADAPTIVE TRACKING OF LARGE-SCALE BRAIN NETWORK ACTIVITY FOR DECODING AND CONTROL OF BRAIN STATES," filed on Jul. 10, 2017, and U.S. Provisional Application No. 62/530,790, entitled "DECODING MOOD OR OTHER NEUROPSYCHIATRIC STATE FROM LARGE-SCALE MULTISITE BRAIN NETWORK ACTIVITY," filed on Jul. 10, 2017, the entire disclosure of both being hereby incorporated by reference herein in their entirety.

GOVERNMENT RIGHTS

This invention was made with government support under Contract No. W911NF-14-2-0043 awarded by the Defense Advanced Research Projects Agency (DARPA), issued by the Army Research Office (ARO). The government has certain rights in the invention.

BACKGROUND

1. Field

The present disclosure relates to decoding neuropsychiatric states, such as mood, anxiety, or pain, from large-scale multisite brain network activity, and uses thereof in neuroscience and therapy.

2. Description of the Related Art

Characterization of large-scale neural dynamics underlying human affective processing and design of decoders for mood and other neuropsychiatric states are critical for understanding the neural substrates of neuropsychiatric disorders and for developing effective therapies for their treatment. However, several major challenges have impeded this level of understanding. Neurobiological, neuroanatomical, and functional neuroimaging studies have suggested that regulation circuits of mood and other neuropsychiatric states do not reside in a single brain region, but rather involve multiple cortical, subcortical, and limbic regions. Moreover, tracking the variations of natural neuropsychiatric states over long time periods is difficult given the complex nature of neuropsychiatric states. Thus characterization and decoding would require recording neural activity across multiple distributed brain sites, and simultaneously obtaining neuropsychiatric state measurements. Also, importantly, identifying neural networks that predict and decode neuropsychiatric states require developing modelling techniques that incorporate data from distributed large-scale neural sites and further deal with the sparsity in available neuropsychiatric state measurements, caused by the difficulty of neuropsychiatric state assessment. Thus decoding neuropsychiatric states from neural activity has so far remained elusive.

Given the above challenges, functional representations of neuropsychiatric states in the human brain have been largely studied in experimental settings using non-invasive neuroimaging techniques. These studies have provided significant insight by showing regional changes induced by presentation of an emotional stimulus in healthy subjects and identifying altered resting-state activity that may be related to neural circuit dysfunctions or to treatment effect in patients with neuropsychiatric state disorders. Informed by these findings, some work has been done on open-loop deep brain stimulation (DBS) for major depressive disorder (MDD).

While open-loop treatments including DBS have been promising, precisely-tailored therapies for neuropsychiatric disorders such as depression and anxiety would require a closed-loop approach in which an objective decoding of neuropsychiatric state, such as mood, guides treatment. For example, for DBS, one route to optimize treatment efficacy would be to use neural recordings to decode mood or other neuropsychiatric state and guide stimulation in real time. However, a major obstacle to implementation of such tailored treatments is the lack of understanding and methodology necessary to robustly decode neuropsychiatric states such as mood or anxiety level. The precise spatiotemporal characteristics of neural activity in the distributed cortico-limbic networks relevant to neuropsychiatric states are not well-understood; also, the tuning of neural activity to neuropsychiatric state may be different depending on factors such as the subject's psychiatric conditions, e.g., depression vs. anxiety vs. healthy. These factors create a challenging decoding problem. Prior studies have failed to focus on investigating activity co-variations with neuropsychiatric state changes over time in an individual or on decoding neuropsychiatric states, such as mood. Also continuous long-term experiments may not be practical in current neuroimaging settings, hindering the tracking of natural neuropsychiatric states over long time periods and localized local field potential (LFP) leads may hinder neural recording from the relevant distributed cortico-limbic regions. Thus the precise spatial distribution and temporal dynamics of neural activities that are predictive of neuropsychiatric state variations over time are largely unknown.

Moreover, the extent to which neural representations of neuropsychiatric states manifest in similar and idiosyncratic ways among individuals is also unknown. This poses another major obstacle to decoding because the brain sites and neural features that should be included in decoding are not known and may vary from subject to subject. Inter-subject variabilities, such as genetic variations and idiosyncratic clinical mood symptoms, suggest that, while there may exist conserved neuropsychiatric state-relevant brain regions across the population, the most neuropsychiatric state-predictive neural networks might need to be learned in each individual from data. Such inter-subject variabilities may explain the inconsistencies in results from clinical trials that have attempted translational application.

It would be desirable, therefore, to overcome these and other limitations of prior approaches for decoding mood or other neuropsychiatric states such as anxiety, fear, pain, or the like.

SUMMARY

Disclosed is a method for decoding mood or other neuropsychiatric states from large-scale brain activity. The method includes receiving, by one or more computers, large-scale brain activity signals from an electrode assembly coupled to a subject. The method also includes continuously and automatically decoding, by the one or more computers, at least one of a mood or neuropsychiatric state of the subject from the large-scale brain activity signals received from a predictive network subset of brain sites coupled to the electrode assembly, contemporaneously with the receiving.

The method also includes providing a signal indicative of the detected mood or neuropsychiatric state, based on the decoding.

Also disclosed is an apparatus for decoding mood or neuropsychiatric state from large-scale brain activity. The apparatus includes one or more processors coupled to a memory holding program instructions. The instructions, when executed by the one or more processors causes the apparatus to receive, by one or more computers, large-scale brain activity signals from an electrode assembly coupled to a subject. The instructions also cause the apparatus to continuously and automatically decode, by the one or more computers, at least one of a mood or neuropsychiatric state of the subject from the large-scale brain activity signals received from a predictive network subset of brain sites coupled to the electrode assembly, contemporaneously with the receiving. The instructions also cause the apparatus to provide a signal indicative of the detected mood or neuropsychiatric state, based on the decoding.

Also disclosed is a method for enabling decoding of mood or neuropsychiatric state from large-scale brain activity using a state space brain activity model that estimates a subject's mood or neuropsychiatric state from contemporaneous neurophysiological signal data. The method includes selecting a most predictive network subset of a large-scale electrode network coupled to a brain of a subject by a progressive region selection technique. The method also includes extracting signal features from neurophysiological signal data output by the large-scale electrode network. The method also includes fitting a state space brain activity model to the extracted signal features and to independently derived measures of mood or neuropsychiatric state using a machine learning technique, resulting in a brain activity model that continuously estimates an averaged state indicator of the subject's mood or neuropsychiatric state. The method also includes regressing the averaged brain state indicator or the extracted neural signal features to the independently derived behavioral, psychological, and/or physiological measures of mood or neuropsychiatric state. The method also includes automatically selecting regression parameters that minimize error and sensitivity of the regression model in decoding of mood or neuropsychiatric state. The regression may be ridge regression, lasso regression, logistic regression, or support vector machine regression, for example.

Also disclosed is an apparatus for enabling decoding of mood or neuropsychiatric state from large-scale brain activity. The apparatus includes one or more processors coupled to a memory holding program instructions. The instructions, when executed by the one or more processors causes the apparatus to select a most predictive network subset of a large-scale electrode network coupled to a brain of a subject by a progressive region selection technique. The instructions also cause the apparatus to extract signal features from neurophysiological signal data output by the large-scale electrode network. The instructions also cause the apparatus to fit a state space brain activity model to the extracted signal features and to independently derived measures of mood or neuropsychiatric state using a machine learning technique, resulting in a brain activity model that continuously estimates an averaged state indicator of the subject's mood or neuropsychiatric state. The instructions also cause the apparatus to regress the averaged brain state indicator and/or the extracted neural signal features to the independently derived behavioral, psychological, and/or physiological measures of mood or neuropsychiatric state. The instructions also cause the apparatus to automatically select regression parameters that minimize error and sensitivity of the regression model in decoding of mood or neuropsychiatric state.

Also disclosed is a method for adaptive tracking of large-scale brain network activity. The method includes characterizing, by one or more computers, a time-variant linear state-space model predictive of a brain state such as mood or other neuropsychiatric state, at least in part by updating estimates of time-varying covariance matrices at time steps, including weighting recent large-scale brain network activity data more heavily than less recent large-scale brain network activity data. The method also includes tracking large-scale brain network activity in a subject using an electrode array coupled to the one or more computers that collect the brain network activity data. The method also includes continuously and automatically estimating, by the one or more computers coupled to the electrode array, the subject's brain state such as mood or neuropsychiatric state contemporaneously with the characterizing and tracking based on the time-variant linear state-space model and the brain network activity data.

Also disclosed is an apparatus for adaptive tracking of large-scale brain network activity, comprising one or more processors coupled to a memory holding program instructions. The instructions, when executed by the one or more processors, causes the apparatus to characterize, by one or more computers, a time-variant linear state-space model predictive of a brain state such as mood or other neuropsychiatric state, at least in part by updating estimates of time-varying covariance matrices at time steps, including weighting recent large-scale brain network activity data more heavily than less recent large-scale brain network activity data. The instructions also cause the apparatus to track large-scale brain network activity in a subject using an electrode array coupled to the one or more computers that collect the brain network activity data. The instructions also cause the apparatus to continuously and automatically estimate, by the one or more computers coupled to the electrode array, the subject's brain state such as mood or neuropsychiatric state contemporaneously with the characterizing and tracking based on the time-variant linear state-space model and the brain network activity data.

To resolve the modeling challenge, the key idea is to restrict the number of model parameters that need to be fitted using the sparse neuropsychiatric state measurements, such as the sparse immediate mood scaler (IMS) points to be less than the number of available IMS points, thus enabling generalizable decoding. Thus, a two-component neural encoding model is constructed to relate neural activity to IMS. Training this model fully specifies the decoder. The first component extracts a small number of hidden variables from neural activity by performing dimensionality reduction. The second component linearly regresses only these hidden variables, termed neural predictors, to IMS points. Since for a given neural encoding model only the regression parameters are fitted using the IMS points, during dimensionality reduction, the number of neural predictors—which is equal to the number of regression parameters—is restricted to be smaller than the number of available IMS points. The neural encoding models are chosen to be dynamic to describe mood state variations over time in terms of the time-variations, i.e., dynamics, of neural activity.

To reduce dimensionality in the first component, multiple steps are used. First, since mood is likely represented across multiple distributed brain regions, it is hypothesized that it may be sufficient to model and use a small subset of these regions for decoding. Thus, instead of using the large number of neural features, a progressive region selection method is used to identify and model only the smallest network of brain regions that were sufficient for decoding. This small network is selected purely based on the train data, and to minimize both sensitivity to and prediction error for this train data. Second, even within a small network and unsupervised with respect to IMS points (i.e., only using the neural data, for example, consisting of multiple days of electrocorticogram (ECoG) recordings), a dynamic model for neural features is trained to describe their time-variations in terms of a low-dimensional hidden neural state. The dynamic model first applies principal component analysis (PCA) on neural features and then identifies the low-dimensional hidden neural state by training a linear state-space model (LSSM) on the retained principal components (PCs). This hidden neural state constitutes the neural predictors; thus its dimension is restricted to be similar to or smaller than the number of available IMS points. The second component consists of a regularized linear regression from neural predictors to IMS points. Together, these components avoid overfitting to the train IMS and thus enable generalizable decoding.

Once the neural encoding model is fitted and selected using the train data, it is used to build the decoder that predicts the test IMS. Optimal decoding involves using a Kalman filter to estimate the hidden neural state at the time of the test IMS, and then the regression model is used to predict the test IMS from the estimated neural state, all within cross-validation. An average cross-validated IMS prediction error across all test IMS points is obtained. To evaluate significance, the same modeling framework is applied to IMS points randomly drawn from the same range as the true IMS in each subject (random-test), and to time-permuted IMS points (permuted-test). The random/permuted P value is defined as the probability that random/permuted IMS points will have lower cross-validated prediction error than the true IMS points.

Described herein are systems and methods for developing mood and other neuropsychiatric state decoders to facilitate future neurotechnologies for tailored therapies. Experiments were carried out that continuously recorded large-scale intracranial ECOG signals and simultaneously collected self-reported mood state measurements over multiple days in epilepsy subjects. Critically, a robust data-driven modeling framework was derived that can use the sparse mood state measurements to identify a parsimonious mood-predictive network (or a network predictive of other neuropsychiatric states) from high-dimensional neural recordings in each subject and train a dynamic neural encoding model within the identified network. The trained model was used to develop decoders that predict mood state over time from neural spectral features in each subject.

The present disclosure illustrates that the decoders predicted mood state variations in each subject over multiple days from large-scale neural activity. In all subjects, the decoders largely recruited networks within the limbic regions. Moreover, specific spectro-spatial neural features within these networks were tuned to mood state variations over time, allowing the decoder to leverage their collective tuning to predict mood state. Finally, the dynamic neural encoding models can be used as a tool to analytically calculate the time-scales of the decoded mood state. This disclosure provides a mood state or other neuropsychiatric state decoding framework with significant implications for future personalized closed-loop therapies for neuropsychiatric disorders, such as depression and anxiety.

BRIEF DESCRIPTION OF THE DRAWINGS

Other systems, methods, features, and advantages of the present invention will be or will become apparent to one of ordinary skill in the art upon examination of the following figures and detailed description. Additional figures are provided in the accompanying Appendix and described therein.

FIGS. 2A, 2B, 2C, and 2D illustrate details of model fitting, selection, and evaluation according to an embodiment of the present disclosure;

FIG. 8 illustrates a summary of cross validated IMS prediction accuracy of mood state decoders and spatial distribution of optimal small mood-predictive networks according to an embodiment of the present disclosure;

FIG. 20 illustrates demographic information, intracranial implant duration, and seizure foci for each of multiple subjects of experiments according to an embodiment of the present disclosure;

FIG. 21 illustrates a list of questions in an IMS test according to an embodiment of the present disclosure;

FIG. 22 illustrates specifications of mood state measurements in each of multiple subjects of experiments according to an embodiment of the present disclosure;

FIG. 23 illustrates a summary of cross-validated prediction error of coherence-based mood state decoders according to an embodiment of the present disclosure;

FIG. 24 illustrates specifications of intracranial electrode coverage in each of multiple subjects of experiments according to an embodiment of the present disclosure;

FIGS. 25A and 25B illustrate a range of mood state variations observed in each of multiple subjects and correlation between PHQ-9 and GAD-7 scores with IMS scores according to an embodiment of the present disclosure;

FIG. 29 illustrates details of a fitted neural encoding model corresponding to a best small mood-predictive network according to an embodiment of the present disclosure;

FIG. 30A illustrates details of a best small mood-predictive network for decoding in each of multiple subjects of experiments according to an embodiment of the present disclosure;

FIG. 30B illustrates a list of abbreviations used for anatomical regions according to an embodiment of the present disclosure;

FIGS. 34A, 34B, and 34C illustrate adaptive and non-adaptive tracking of ECoG dynamics in one subject according to an embodiment of the present disclosure.

DETAILED DESCRIPTION

Figure 1A:
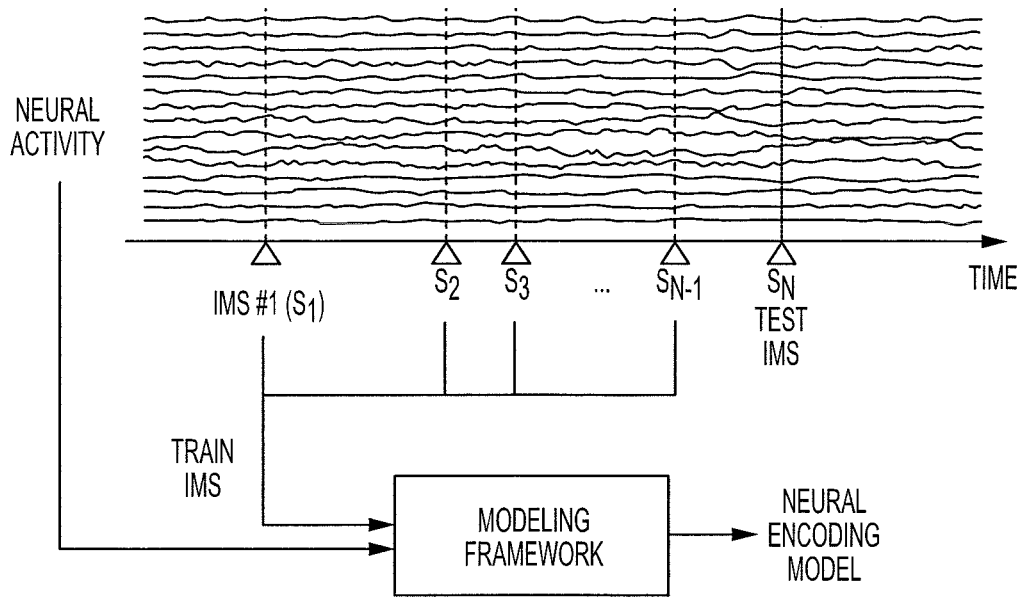
FIGS. 1A, 1B, and 1C illustrate decoder training and evaluation using cross validation according to an embodiment of the present disclosure.

As used herein, "large-scale" means that the brain activity pertains to networks comprised of many neurons, and not to activity at a single neuron or small group of related neurons. "Multisite" means that activity is tracked at multiple sites in the brain, and not merely at a single site. The present technology pertains to multisite networks, and to single site networks. As used herein, "brain state" refers to any one or more of a neuropsychiatric state such as for example, fear, calm, anger or bliss, moods such as for example sadness, happiness, boredom, interest, and/or other confirmable brain states such as for example motor intention (e.g., intent to move a muscle) or cognitive states such as for example attention or inattention. As used herein, brain states are perceivable by the subject and/or objectively confirmable by means other than brain activity as sensed by an electrode array or the like.

Neuropsychiatric State Decoding Methods

The present disclosure describes systems and methods for decoding neuropsychiatric states (e.g., mood) from large-scale multisite brain activity (or in the special case, single-site brain activity) using a state space brain activity model that estimates a mood or other neuropsychiatric state of a subject from contemporaneous neurophysiological signal data, or enablement of such decoding.

Decoding technologies have conventionally been largely designed for brain states that are well-represented in localized brain areas. For example, in motor brain-machine interfaces (BMIs), given the somatotopic organization of the motor cortex, motor intentions can be decoded from localized regions in motor cortical areas. Moreover, the behavioral measurements required for training these decoders are not sparse, for example, movements can be measured or inferred continuously in time. These aspects have facilitated personalized motor decoding in real-time BMIs using neural spiking, localized intracranial local field potential (LFP), and electrocorticogram (ECoG). Decoding mood and other neuropsychiatric states poses critical new modeling challenges due to multiple differences. Representation of mood involves multiple distributed brain sites rather than localized regions, and the functional organization of mood-predictive networks is not as well-understood. Further, mood cannot be behaviorally measured frequently, resulting in sparse measurements at discrete times (e.g., 12 plus or minus 2.4 Immediate Mood Scaler (IMS) points per subject here). The present disclosure resolves the new modeling challenges by designing multiple components.

First, dimensionality reduction is applied using progressive region selection and dynamic modeling to identify a small number of hidden neural predictors. Then, only these predictors are related to IMS with regularized linear regression. Future chronic recordings may allow for more mood state measurements per subject and thus enable the incorporation of a larger number of neural predictors. This would allow for modeling larger mood-predictive networks to improve decoding accuracy. Moreover, as new IMS points are collected, models may be recalibrated and adapted (as detailed below) to maintain successful decoding over time despite neural non-stationarities and occurrence of new mood ranges.

Generally, the modeling framework of the systems and methods for decoding neuropsychiatric states first reduces the dimensionality of the neural features to obtain a small number of hidden variables to serve as neural predictors, and then only relates these neural predictors to the train IMS via a linear regression. It then uses the resulting trained decoder to predict the test IMS, which is not seen by any step of model training.

Figure 1B:
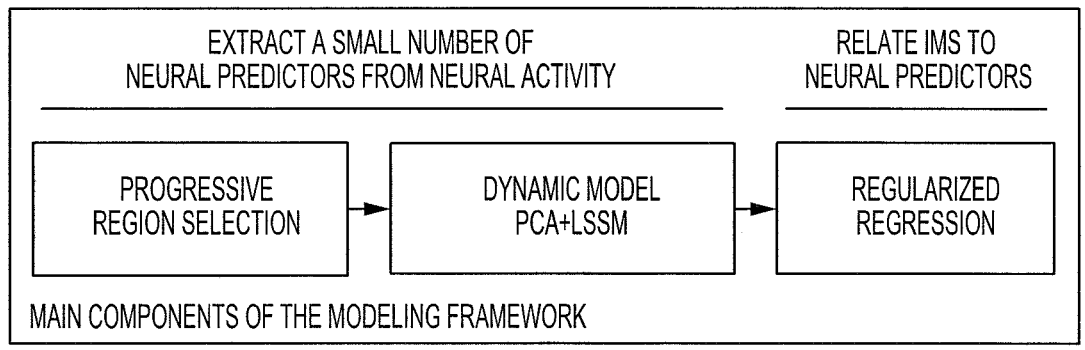
Figure 1C:
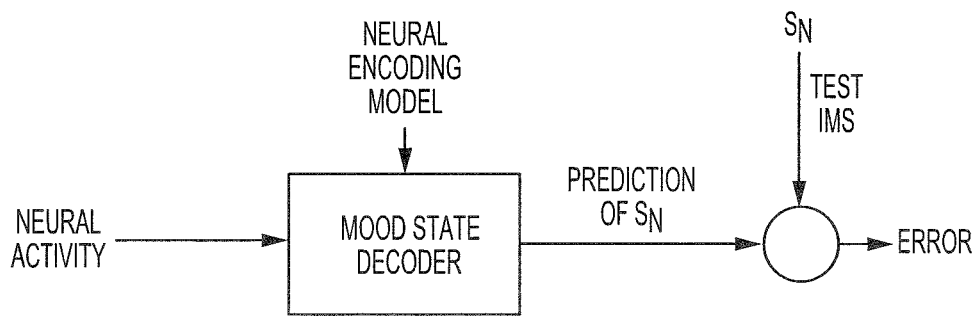

FIGS. 1A-1C illustrate decoder training and evaluation using cross-validation. Referring to FIG. 1A, in cross-validation, an IMS point (as an example, $S_N$) is left out as test IMS to be predicted. The other IMS points (i.e., train IMS, here $S_1$ to $S_{N-1}$) and the associated neural activity are used within the modeling framework to train a neural encoding model. Referring to FIG. 1B, to enable training generalizable decoders, multiple components within the modeling framework reduce the number of model parameters that need to be fitted using the IMS points (i.e., regression parameters). Progressive region selection selects only a small subset of regions for use in the decoder. Dynamic modeling using principal component analysis (PCA) and linear state-space model (LSSM) describes the temporal dynamics of neural activity in the selected network through a low-dimensional hidden neural state, which constitutes the neural predictors. A regularized regression model then relates this small number of neural predictors to mood state. Regularization further reduces the effective number of regression parameters. Referring to FIG. 1C, the trained neural encoding model is used to build a decoder that predicts mood state based on the observed neural activity. The decoder is used to predict the test IMS ($S_N$). We calculate the prediction error as the difference between the prediction of the test IMS and the true test IMS. The above procedure is performed once for each IMS, thus forming leave-one-out cross-validation. Decoding performance is evaluated using the average cross-validation error.

FIGS. 2A-2D provide details of model fitting, selection and evaluation. FIG. 2A illustrates that progressive region selection starts with a network size of one (Net. Size=1, i.e., one region), and progressively increases the network size until decoding becomes possible (with false discovery rate (FDR) control to correct for multiple comparisons). At each stage, model selection and model fitting are performed with leave-one-out cross-validation using the train IMS; then the corresponding decoder is tested on the test IMS. To assess significance, the same procedure is performed on sets of random IMS points to compute the random-test P value.

FIG. 2B illustrates model fitting for a candidate neural encoding model specified by a given network, a given number of principal components (PCs), and a given neural state dimension. PCA and LSSM are fitted purely based on neural features, unsupervised with respect to IMS points. Regression model is fitted using the train IMS with regularization.

FIG. 2C illustrates model selection involving fitting several candidate neural encoding models by considering different networks, number of PCs and neural state dimensions. For each candidate neural encoding model, prediction error for train IMS and sensitivity to train IMS are computed and a neural encoding model with small values for both measures is selected.

FIG. 2D illustrates that the selected neural encoding model is then used to build a decoder to predict the test IMS. Note that the test IMS is never seen in model fitting in FIG. 2B or in model selection in FIG. 2C, which together specify the decoder. The decoder extracts neural features from the selected network, linearly transforms them to PCs, extracts the neural state via Kalman filtering, and applies a linear regression to them to predict mood state at the time of the test IMS. The decoder is evaluated only at the discrete time-points that the questionnaire is filled, i.e., that a true measured IMS point is observed.

Dimensionality is reduced by considering candidate models that 1) preferably consist of a small number of regions and 2) describe the neural activity in these regions in terms of a low-dimensional hidden variable. A limited number of candidate models may be fit and compared with the above qualities and then one of them is selected, all using only the train IMS within cross-validation.

The candidate models are generated through progressive region selection and dynamic modeling, which constitute the dimensionality reduction steps. In progressive region selection (illustrated in FIG. 2A), the process starts from considering the smallest possible networks, i.e., all possible networks with a single region. To model activity in each region (illustrated in FIG. 2B), dynamic modeling consisting of principal component analysis (PCA) and linear state-space model (LSSM) is used that—completely unsupervised with respect to IMS points and purely based on neural features—extract a low-dimensional hidden neural state. This neural state constitutes the neural predictors. Thus in all candidate models, this neural state dimension is restricted to be similar to or smaller than the number of available IMS points. Then, a regularized linear regression is fit from this low-dimensional hidden neural state to train IMS. Given that the only parameters in a candidate model (illustrated in FIG. 2B) that need to be fitted using the train IMS are the regression parameters—which are equal in number to the small number of neural predictors—the dimensionality reduction process avoids overfitting to train IMS.

Once all the candidate models are obtained (e.g., corresponding to different single regions), one of them is selected purely using the train IMS (illustrated in FIG. 2C). To promote generalizability, a model is selected with not only small prediction error for train IMS but also low sensitivity to train IMS. Then the decoder for this model is constructed and used to predict the test IMS, which has not been seen by any step of modeling (illustrated in FIG. 2D). If prediction of test IMS is significant (random-test), the method is stopped (as shown in FIG. 2A). In 5 of 7 subjects, the method indeed stopped at one region. If not, it is declared that a one-region network is not sufficient for decoding and the cross-validated modeling process is started from scratch but this time with candidate models consisting of two regions. This progressive process continues until either prediction is possible or all regions have been considered and prediction is not possible. Additional details are provided below.

The method consists of progressive stages to find the smallest network size sufficient for decoding (illustrated in FIG. 2A). Each ECoG strip or depth electrode (which have several channels) is defined as a region. In the first stage, neural encoding models are fit for every single region on its own, i.e., networks of size one consisting of a single electrode's recording channels (illustrated by Model Fitting in FIG. 2B). Among the candidate single-region neural encoding models, a generalizable model is selected by considering both the prediction error and the sensitivity measures of candidate models, which are computed purely from the train data (illustrated by Model Selection in FIG. 2C). Finally, a mood state decoder is built based on the selected neural encoding model. This decoder is then used to predict the test IMS—which has not been seen by any step of model fitting or selection—and thus compute the cross-validated prediction error (illustrated in FIG. 2D). This process is repeated for all IMS points (i.e., conduct leave-one-out cross-validation) to compute the average cross-validated prediction error.

The decoding measure used is the error between the cross-validated prediction of a test IMS point and its true value. The average cross-validated prediction error may be normalized root mean-squared error (NRMSE), as shown in Equation 1 below.

$$NRMSE = \frac{\sqrt{\sum_{j=1}^{N}(\hat{s}^{(j)} - s^{(j)})^2}}{\sqrt{\sum_{j=1}^{N}(\bar{s}^{(j)} - s^{(j)})^2}} \quad \text{Equation 1}$$

In Equation 1, N is the total number of IMS points, $s^{(j)}$ is the jth IMS point, $\hat{s}^{(j)}$ is the cross-validated prediction of the jth IMS point (i.e., prediction of the jth IMS point with a decoder that is trained without seeing this IMS point) and $\bar{s}^{(j)}$ is the mean of other IMS points except for the jth IMS point. Thus, NRMSE is the cross-validated root mean-squared error (RMSE) normalized by the RMSE of predicting the test IMS point as the mean of other IMS points.

If the cross-validated prediction of test IMS is significant ($P \leq 0.05$, random-test), it is declared that mood state can be decoded from a network of size one and the region selection process is terminated. As shown in experimental data, this was the case for 5 of 7 subjects.

Only if decoding is not possible with a one-region network, the method proceeds to the second stage to construct two-region networks. The cross-validated model fitting, selection, and evaluation is repeated exactly as in the first stage, this time for candidate two-region networks. To make the search space practical, the first region of all candidate two-region networks is fixed as the region that is selected purely based on train IMS in the first stage. Also, in the second stage, a correction is made for making two comparisons (one for one-region network and one for two-region network) using false discovery rate (FDR) control. If the FDR corrected $P \leq 0.05$, it is declared that mood state can be decoded from a network of size two and the region selection process is terminated. If not, the process is repeated by progressively increasing the network size and performing FDR correction, until a stage is obtained in which the FDR corrected $P \leq 0.05$; at such a stage, it is declared that decoding is possible with a network size corresponding to that stage. If the procedure does not lead to significant decoding (i.e., $P > 0.05$) even when including all regions, it is declared that decoding is not possible. An alternative statistical test is also devised that empirically accounts for multiple comparisons and therefore does not require FDR correction (described in detail below). In experimental tests, the results were consistent using both tests across the subjects.

For a given candidate network in the progressive region selection procedure, a neural encoding model is built that describes the temporal dynamics of neural features in terms of a low-dimensional hidden neural state, and then this model is related to the neural state to train IMS points.

Assuming $n_z$ neural features in the network, the features at time t are denoted by $z_t \in \mathbb{R}^{n_z}$. The low-dimensional hidden neural state is identified completely unsupervised with respect to (i.e., without knowing) IMS points and merely to describe the temporal dynamics of neural features. PCA is performed to extract the top $n_y$ principal components (PCs), $y_t \in \mathbb{R}^{n_y}$, via a linear transform, as shown in Equation 2 below.

$$y_t = P z_t \quad \text{Equation 2:}$$

In Equation 2, rows of P consist of eigenvectors corresponding to the $n_y$ largest eigenvalues of the neural feature sample covariance matrix. Then, an LSSM is fit to these PCs $y_t$ to define the low-dimensional hidden neural state $x_t \in \mathbb{R}^{n_x}$. The LSSM is written as shown below in Equation 3.

$$\begin{cases} x_{t+1} = Ax_t + Ke_t \\ y_t = Cx_t + e_t \end{cases} \quad \text{Equation 3}$$

In Equation 3, the neural noise and model mismatch is modeled as a white Gaussian noise $e_t \in \mathbb{R}^{n_y}$ with covariance matrix $E\{e_i e_j^T\} = R\delta_{ij}$ ($S_{ij}=1$, if i=j and 0 otherwise). To enable generalizability, the upper-bounds on the number of retained PCs $n_y$ as restricted and the neural state dimension $n_x$, is restricted to be similar to or smaller than the typical number of available IMS points. For a given network, $n_y$, and $n_x$, the model parameters are the PCA matrix $P \in \mathbb{R}^{n_y \times n_z}$ and the LSSM matrices $A \in \mathbb{R}^{n_x \times n_x}$, $C \in \mathbb{R}^{n_x \times n_y}$, $K \in \mathbb{R}^{n_x \times n_y}$, $R \in \mathbb{R}^{n_y \times n_y}$. All model parameters are fitted unsupervised with respect to IMS points and only based on neural features using standard methods. Note that LSSMs have also been used in BMIs; there the state is largely taken as the behavioral (e.g., kinematic) state rather than a low-dimensional hidden neural state for dimensionality reduction.

Once the PCA/LSSM is fitted and the neural state is identified, a linear regression model is built that relates the neural state $x_t$ to train IMS points, denoted by $s_t$, as shown in Equation 4 below.

$$s_t = Tx_t + s_0 + \varepsilon_t. \quad \text{Equation 4:}$$

In Equation 4, $s_0 \in \mathbb{R}$ is the mean of the train IMS and $\varepsilon_t \in \mathbb{R}$ is a zero-mean white Gaussian noise.

Together, Equations 2-4 provide a parametric candidate neural encoding model. The only parameters of a candidate model that are fitted using the train IMS are the regression parameters $T \in \mathbb{R}^{1 \times n_x}$, $s_0$. The neural encoding model is dynamic, which introduces multiple benefits, e.g., denoising neural features and accumulating information from them over time, and time-scale computations.

The mood-encoding model expressed in Equations 2-4 is a dynamic linear model and thus facilitates a closed-form representation of the power spectral density (PSD), $S(\omega)$, of the decoded mood state $\hat{s}_t$ that can be derived as shown below.

$$S(\omega) = \sum_{i=1}^{n_y} \sum_{i=1}^{n_y} H_i(\omega) H_j^*(\omega) R_{ij}$$

where $\omega \in [-\pi, \pi]$ is the radial frequency, $R_{ij}$ is the (i,j)th component of the noise covariance matrix R in Equation 3, and $H_i(\omega)$ is the scalar transfer function from the ith component of noise $e_t$ to the decoded mood state $\hat{s}_t$ defined as $H_i(\omega) = T(e^{j\omega}I - A)^{-1}K^{(i)}$, where $K^{(i)}$ represents the ith column of the matrix K in Equation 3. The PSD shows the distribution of different frequencies (or equivalently their corresponding time-scales defined as the inverse of frequency) of neural feature dynamics that are used by the decoder. From the PSD, the frequency $\omega_0$ can be found, for example, below which 70% of the powers are concentrated. The equivalent time-scale corresponding to each frequency $\omega_0$ can be found as $$\frac{2\pi}{\omega_0 F_S} \text{ where } F_S = \frac{1}{10} \text{ Hz}$$

because of the 10 s time-step.

It is emphasized that the above PSD is the PSD of the neural feature time-series and should not be confused with the PSD of the raw ECOG signal time-series. Neural features consist of ECOG spectral powers in frequency bands above 1 Hz. As a pre-processing step, the method high-pass filters the raw ECOG time-series above 1 Hz before extracting the neural feature time-series. However, it is emphasized that no similar filtering is applied to the neural feature time-series, which are used for decoding mood. Therefore, unlike the PSD of the pre-processed raw ECoG time-series, the PSD of the neural feature time-series is not in any way limited in the frequency domain from below and could have low-frequency (i.e., slow time-scale) components. Thus, technically, the time-scale of neural features and similarly the time-scale of decoded mood can be arbitrarily slow. This would just mean that the neural features change slowly in time (in the special case, they can be constant in time corresponding to their PSD being concentrated at 0 frequency).

The optimal decoder for the neural encoding model in Equations 2-4 consists of three main steps (as illustrated in FIG. 2D). First, it applies the linear transformation in Equation 2 to the neural features $z_t$ to obtain the PCs, $y_t$. Second, it uses the optimal recursive Kalman filter for the LSSM in Equation 3 to estimate the neural state $\hat{x}_t$ from the PCs $y_t$ as shown below in Equation 5.

$$\hat{x}_t = A\hat{x}_{t-1} + K(y_t - C\hat{x}_{t-1})  \quad \text{Equation 5:}$$

In Equation 5, K is the gain matrix. The decoder then applies a moving average to estimate the neural state, $\bar{x}_t$, over the past several seconds and/or minutes, for example, 4 minutes which is roughly the time it takes to fill one full IMS questionnaire. Third, using Equation 4, the decoder estimates IMS, $\hat{s}_t$ as shown below in Equation 6.

$$\hat{s}_t = T\bar{x}_t + s_0 \quad \text{Equation 6:}$$

For a given network and a given number of retained PCs $n_y$ and neural state dimension $n_x$, the fitting of model parameters consists of an unsupervised learning step (i.e., which does not look at IMS points) and a supervised learning step (as illustrated in FIG. 2B).

In the unsupervised learning step, the PCA and LSSM parameters P, A, C, K, and R are fit purely from neural data, without any information from the train IMS. The neural spectral features are concatenated within 10 hours of IMS points, for example (union of 20 hour windows centered at each IMS point) to form $z_t$. Then, PCA is conducted on $z_t$ to fit P and retain the first $n_y$ PCs as $y_t$. The LSSM parameters A, C, K and R are then fitted using subspace identification, which is a stable numerical algorithm to fit LSSMs only from observed data $y_t$ when the neural state $x_t$ is hidden. Since the fitting of PCA and LSSM is simply based on days of continuous neural recordings, there is no shortage of data in this unsupervised learning step.

In the supervised learning step, the fitted LSSM is used to estimate the averaged neural state $\bar{x}_t$ from $y_t$ using Equation 6 and the 4-min (or other time period) averaging. Then, ridge regularization is used to fit T and $s_0$ as the optimal solution as shown in Equation 7 below.

$$\min_{T, s_0} \sum_{k=1}^{M} \left(s^{(k)} - T\bar{x}^{(k)} - s_0\right)^2 + \lambda \|T\|_2^2 \quad \text{Equation 7}$$

In Equation 7, $s^{(k)}$ is the k'th train IMS point, $\bar{x}^{(k)}$ is the average state around the k'th train IMS, M=N−1 is the number of train IMS points, and λ>0 is the regularization parameter selected using standard inner-level cross-validation. The total number of regression parameters is $n_x+1$ ($n_x$ parameters for T and 1 for $s_0$). Ridge regularization further ensures that the effective number of regression parameters is strictly less than $n_x+1$ and also less than the number of train IMS points. Together the progressive region selection, PCA, LSSM, and regularization could make the effective number of regression parameters to be about 30-50% of the number of available IMS points in every subject (as illustrated in FIG. 29).

In progressive region selection, at each stage, a pool of candidate models can be fit (for different choices of regions, number of retained PCs $n_y$ and neural state dimension $n_x$) and one should be selected (as illustrated in FIG. 2C). A model selection technique is therefore desirable that only uses the train IMS to pick a model that is likely to generalize to the test IMS. Thus, a measure is introduced that evaluates the sensitivity of a given model to the train IMS. A model is then selected among models that have low sensitivity to the train IMS even if they do not have the lowest prediction error for the train IMS. For simplicity, the model selection procedure for a network size of one, i.e., with a single region, is first provided. The method then extends to larger network sizes.

For G total regions, a single-region network can be built using any one of these G regions. For each region, 4 choices of PC dimension $n_y$ are considered from {1,5,10,15}, and 4 choices of neural state dimension are considered $n_x$ from {3,6,9, DR}. Here DR represents a special case of LSSM corresponding to a direct regression model from $y_t$ to $s_t$ (equivalent to a degenerate LSSM with A=C=$0_{n_y \times n_y}$ and K=$I_{n_y \times n_y}$, where $0_{n_y \times n_y}$ and $I_{n_y \times n_y}$ are $n_y \times n_y$ zero and identity matrices, respectively). The upper limits of $n_y$ and $n_x$ are selected to be comparable to the typical number of available IMS points. This ensures that the number of neural predictors are at most comparable to the number of available IMS points, thus helping prevent overfitting to the train IMS. For each combination of region, $n_y$ and $n_x$, a neural encoding model is fit using the train data as described above (as shown in Model Fitting of FIG. 2B). This forms a pool of 16G candidate models from which one generalizable model is to be selected.

To select a model, two performance measures are computed for each candidate model. First, the prediction error (i.e., NRMSE) of that model is calculated for the train IMS, which is found in an internal leave-one-out cross-validation purely on the train IMS points. Second, based on Cook's distance, the model sensitivity is quantified to train IMS points, denoted by D. For the jth train IMS point, Cook's distance Di is defined as shown below in Equation 8.

$$D_j = \frac{\sum_{k=1}^{M} \left(\hat{s}^{(k)} - \hat{s}^{(k,-j)}\right)^2}{f\hat{\sigma}_e^2} \quad \text{Equation 8}$$

In Equation 8, M=N−1 is the number of train IMS, $\hat{s}^{(k)}$ is the prediction of the kth train IMS by a model fitted to all train IMS, $\hat{s}^{(k,-j)}$ is the prediction of the kth train IMS by a model fitted to all train IMS except for the jth train IMS, f is the effective number of parameters in the regression model, and $$\hat{\sigma}_e^2 = \frac{1}{(M-f)} \sum_{k=1}^{M} \left(\hat{s}^{(k)} - s^{(k)}\right)^2.$$

$D_j$ shows how much influence the jth train IMS point has on the fitting of the neural encoding model. For a given fitted model, the maximum sensitivity to train IMS points is computed, $D=\max_{j \in (1,...,M)} D_j$ as the sensitivity measure. Since $D>1$ implies strong model sensitivity to data points, the model with the smallest prediction error is selected for the train IMS among those that have $D \leq 0.5$. If no model satisfies this limit, the maximum allowed D is gradually relaxed to 1 in 0.1 steps until a model is found that satisfies the limit. If no model has $D \leq 1$, D is discarded and the model with the smallest prediction error for the train IMS is selected. Note that the entire model selection described here is performed completely unaware of the test IMS to be decoded later using the selected model (as illustrated in FIG. 2D).

The model selection procedure is the same for larger networks, except in how the network size is grown. To build candidate networks of size two, the first region is fixed as the one selected in the first stage of the region selection based on train data. This results in G−1 possible two-region networks to choose from. A similar greedy procedure is then used for later stages: at stage h, the first h−1 regions are fixed as those selected in stage h−1 based on the train data, and thus have G−h+1 possible h-region networks to choose from. This greedy algorithm limits the search scope to be much smaller than all possible combinations of regions. Finally, note that all candidate models include all frequency bands.

In the main decoding analysis, the first focus is on limbic regions—including orbitofrontal cortex (OFC), anterior cingulate cortex (ACC), insular cortex (INS), amygdala (AMYG), and hippocampus (HPC)—in progressive region selection given their central role. From each ECoG strip or depth electrode, only included are channels that are confirmed to be within these limbic regions by FreeSurfer and further expert verification. Only if the limbic regions alone are not sufficient for significant prediction (only happened in EC137), is the search extended to all channels from all ECoG electrodes (excluding channels in white-matter). The progressive region-selection is then repeated from scratch. In this case, in addition to the region selection stages, the initial search is also corrected for within the limbic regions in FDR control.

Two control analyses are also performed. First, a search is performed within all electrodes for all subjects. Second, a search is performed only within electrodes outside limbic regions, i.e., exclude all limbic electrodes from the search.

To evaluate decoding at the population level, the IMS points in each subject are standardized by z-scoring the true and cross-validated IMS predictions based on the true IMS points. These standardized values are then pooled from all subjects and the cross-validated NRMSE is computed. To assess statistical significance, one set of the random IMS points is randomly selected from each subject and pooled with a similar procedure. This process is repeated $10^9$ times and the P value is calculated based on the resulting NRMSE distribution. This procedure is repeated to get the permuted-test P value.

Figure 3:
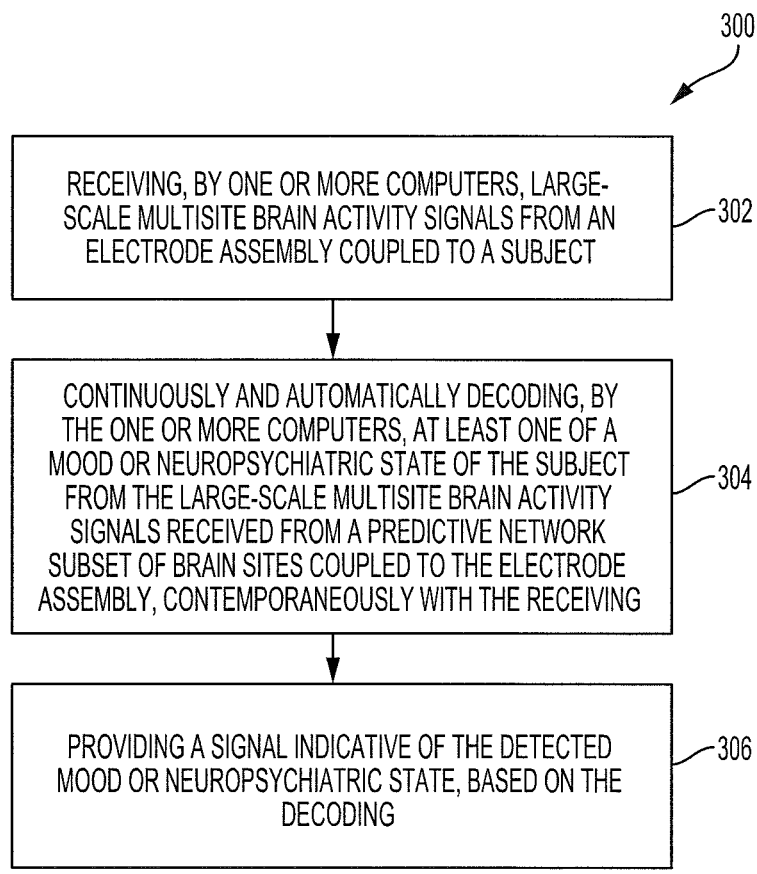
FIG. 3 illustrates a method for identifying a mood or other neuropsychiatric state based on large-scale multisite brain activity signals according to an embodiment of the present disclosure.

FIG. 3 illustrates a method 300 for decoding a neuropsychiatric state from large-scale brain activity. The method 300 includes, at 302, receiving, by one or more computers or processors, large-scale brain activity signals from an electrode assembly coupled to a subject. The brain activity signals may be collected by a multisite network. The method 300 may also be implemented in the special case of a single-site network configured for monitoring large-scale brain activity.

The method 300 may further include, at 304, continuously and automatically decoding, by the one or more processors, at least one of a mood or neuropsychiatric state of the subject from the large-scale brain activity signals received from a predictive network subset of brain sites coupled to the electrode assembly, which may be performed contemporaneously with the receiving. The decoding may include extracting neural signal features from the large-scale brain activity signals received from the predictive network subset. For example, the decoding may include estimating low dimensional neural states by filtering, such as Kalman filtering or other Bayesian filtering, using linear state system parameters derived for the mood-predictive network by state space model fitting. For further example, the decoding may include executing a regression algorithm on the low dimensional neural states using regression parameters for a selected and fitted regression model. In some embodiments, fitting the regression model may be based on the low-dimensional neural state and behavioral/psychological/physiological measures of mood or neuropsychiatric states such as self-reports, facial tracking, audio tracking and speech recognition, pulse, skin temperature, skin wetness, or any other means of tracking behavioral/psychological/physiological measures of the neuropsychiatric state.

In some embodiments, the decoding may include identifying neural signal features that include at least one of a function (e.g., log) of power, a function of coherence, a phase, a phase-amplitude coupling, a waveform, a waveform transform, or the like. For example, the decoding may include measuring coherence of the signals across electrode pairs for multiple frequency bands, measuring power factors of the signals across electrodes for different frequency bands, or aggregating information from multiple recording channels at multiple frequency bands.

The method 300 may further include, at 306, providing a signal indicative of the detected mood or neuropsychiatric state, based on the decoding. The method 300 may further include identifying the predictive network subset at least in part by comparing sensitivity and error of competing regression models.

Figure 4:
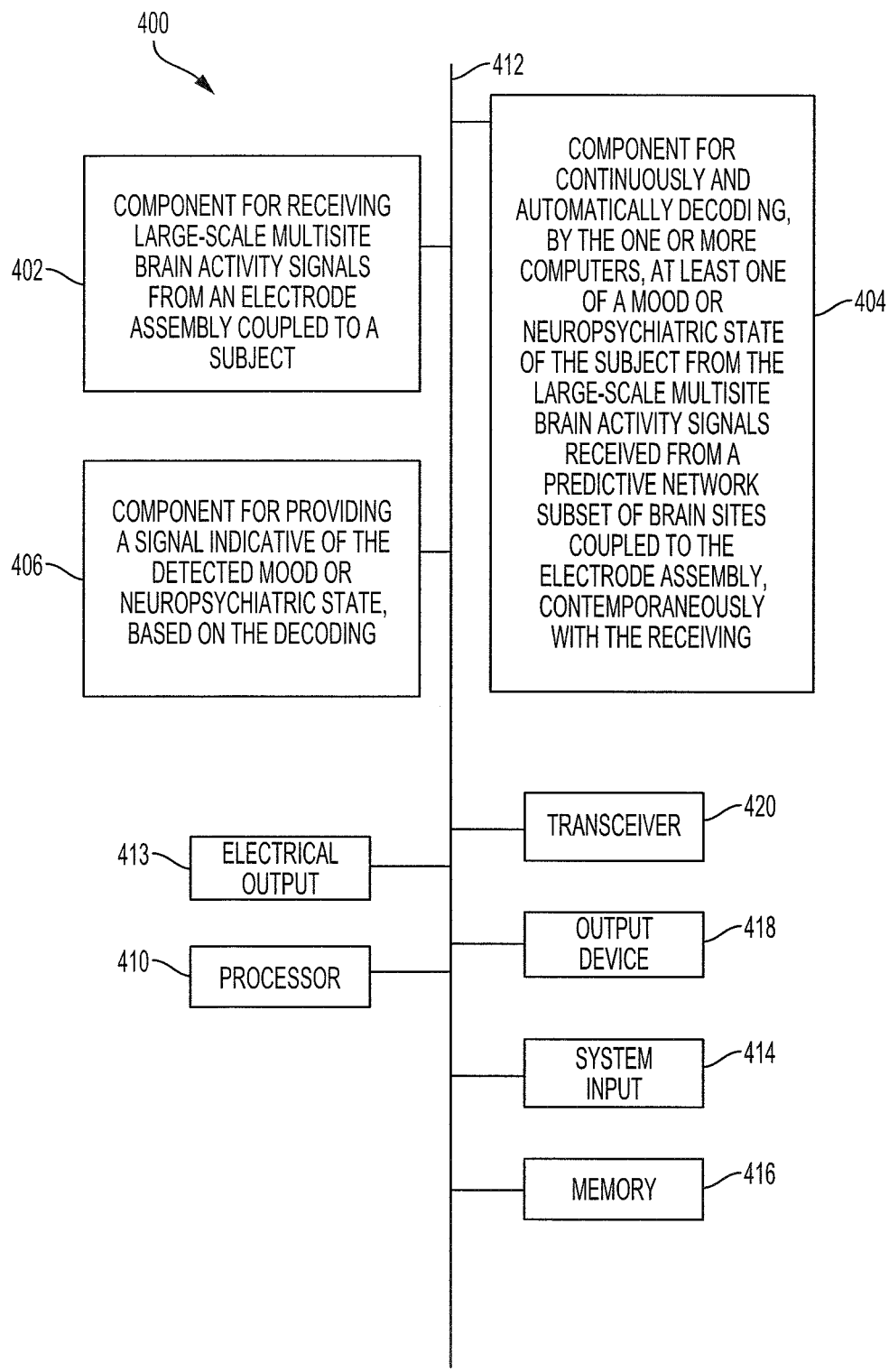
FIG. 4 illustrates a system for identifying a mood or other neuropsychiatric state based on large-scale multisite brain activity signals according to an embodiment of the present disclosure.

FIG. 4 is a conceptual block diagram illustrating components of an apparatus or system 400 for decoding mood or other neuropsychiatric states from large-scale multisite brain activity (or in the special case, single-site activity), as described herein. The apparatus or system 400 may include additional or more detailed components for performing functions or process operations as described herein. For example, a processor 410 and a memory 416 may contain or perform an instantiation of a process for decoding as described herein above. As depicted, the apparatus or system 400 may include functional blocks that can represent functions implemented by a processor, software, or combination thereof (e.g., firmware). In some embodiments, the functional blocks may be performed by the processor 410 as instructions stored in the memory 416, or as programmed into the processor 410.

As illustrated in FIG. 4, the apparatus or system 400 may comprise an electrical component 402 for receiving large-scale multisite brain activity (or in the special case, single-site activity) signals from an electrode assembly coupled to a subject. The component 402 may be, or may include, a means for said receiving. Said means may include the processor 410 coupled to the memory 416, the processor 410 executing an algorithm based on program instructions stored in the memory, or the processor 410 performing an algorithm as stored in the processor (i.e., the processor may be an application specific integrated circuit (ASIC)). Such algorithm may include a sequence of more detailed operations, for example, receiving multiple channels of analog data from an electrode network via a multiplexer or the like, digitizing the analog data, and storing the digitized data in a cache or other memory for processing contemporaneously with receiving.

The apparatus or system 400 may further include an electrical component 404 for continuously and automatically decoding, by the one or more computers, at least one of a mood or neuropsychiatric state of the subject from the large-scale multisite brain activity (or in the special case, single-site activity) signals received from a predictive network subset of brain sites coupled to the electrode assembly, which may be performed contemporaneously with the receiving. The component 404 may be, or may include, a means for said decoding. Said means may include the processor 410 coupled to the memory 416 and to an input device 412, the processor 410 executing an algorithm based on program instructions stored in the memory 416. Such algorithm may include a sequence of more detailed operations, for example, as described herein above in connection with block 304 of the method 300, or as described below.

The apparatus 400 may further include an electrical component 406 for providing a signal indicative of the detected mood or neuropsychiatric state, based on the decoding. The component 406 may be, or may include, a means for said providing. Said means may include the processor 410 coupled to the memory 416, the processor 410 executing an algorithm based on program instructions stored in the memory 416. Such algorithm may include a sequence of more detailed computational operations, for example, receiving a code indicating a mood or neuropsychiatric state from the decoder 404, generating an output signal indicating the code or a human-readable or machine-readable interpretation of the code, and outputting the code, the human-readable interpretation, or machine-readable interpretation to an output device 418 (e.g., a display screen, a touchscreen, or an Ethernet port). For example, the output device 418 may be, or may include, an electrical deep brain stimulator (DBS) that determines its stimulation pattern based on the output signal indicating a decoded mood or neuropsychiatric state (e.g., a closed-loop DBS apparatus).

The apparatus 400 may optionally include the processor 410. The processor 410 may include one or more processor or controller and may be in operative communication with the components 406-406 via a bus 410 or similar communication coupling. In the alternative, one or more of the components may be instantiated as functional modules in a memory of the processor 410. The processor 410 may effect initiation and scheduling of the processes or functions performed by electrical components 402-406.

In some embodiments, the apparatus 400 may include a system input port 414, for example a network interface module operable for communicating with system components over a computer network, or other input such as a touchscreen, a keyboard, a mouse, or the like. A network interface module may be, or may include, for example, an Ethernet port or serial port (e.g., a Universal Serial Bus (USB) port), a Wi-Fi port, a Bluetooth port, or the like. Likewise, the apparatus 400 may include an output port 413 for providing data to an output device for human or machine use, e.g., to a closed-loop DBS apparatus.

In some embodiments, the apparatus 400 may optionally include a component for storing information, such as, for example, a non-transitory memory 416. The computer readable medium or the memory 416 may be operatively coupled to the other components of the apparatus 400 via the bus 410, or the like. The memory 416 may be adapted to store computer readable instructions and data for effecting the processes and behavior of the modules 402-406, and subcomponents thereof, or the processor 410, or the method 300 and one or more of the additional operations disclosed herein. The memory 416 may retain instructions for executing functions associated with the components 402-406. While shown as being external to the memory 416, it is to be understood that the components 402-406 can exist within the memory 416 or an on-chip memory of the processor 410.

The apparatus 400 may include a transceiver 420 configured as a wireless transmitter/receiver, or a wired transmitter/receiver, for transmitting and receiving a communication signal to/from another system component such as, for example, a server or client device. In alternative embodiments, the processor 410 may include networked microprocessors from devices operating over a computer network. In addition, the apparatus 400 may include any suitable display output 418 and user interface device for interaction with a user.

Figure 5:
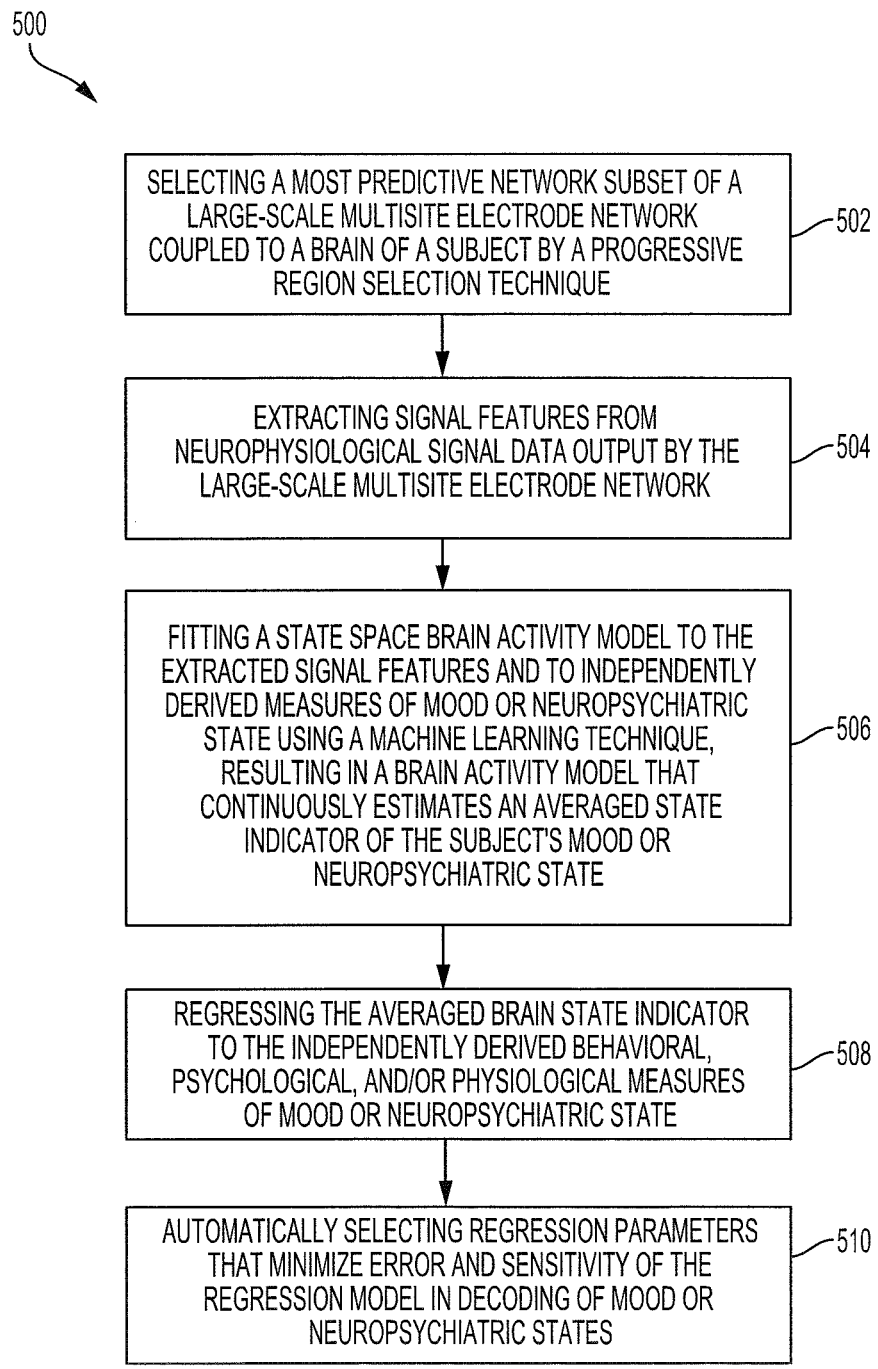
FIG. 5 illustrates a method for enabling decoding of mood or neuropsychiatric state from large-scale multisite brain activity (or in the special case, single-site activity) using a state space brain activity model that estimates a mood or neuropsychiatric state of a subject according to an embodiment of the present disclosure.

Referring to FIG. 5, a method 500 for enabling decoding of mood or neuropsychiatric state from large-scale multisite brain activity (or in the special case, single-site activity) using a state space brain activity model that estimates a mood or neuropsychiatric state of a subject from contemporaneous neurophysiological signal data is shown. The method 500 may be performed by, for example, a system that may include a processor, a memory, or the like.

The method 500 may include, at 502, selecting a most predictive network subset of a large-scale multisite electrode network coupled to a brain of a subject by a progressive region selection technique. The method 500 may further include, at 504, extracting signal features from neurophysiological signal data output by the large-scale multisite electrode network (or in the special case, a single-site network).

The method 500 may further include, at 506, fitting a state space brain activity model to the extracted signal features and to independently derived measures of mood or neuropsychiatric state using a machine learning technique, resulting in a brain activity model that continuously estimates an averaged state indicator of the mood or neuropsychiatric state of the subject. In some embodiments, the state space brain activity model is a linear state-space model (LSSM) as described below. In some embodiments, the model may be a non-linear state-space model. The independently derived measures of mood or neuropsychiatric state may be, or may include, at least one of a subject survey or a measure derived automatically from biometric data collected from the subject exclusive of any data from the large-scale multisite electrode network. Biometric data may include, for example, facial expression, pulse, skin temperature, tone, or wetness, or any other biometric indicator of a mood or neuropsychiatric state. In some embodiments, the state-space model may be used to analytically calculate one or more time-scales of predictive neural dynamics for decoding the mood or neuropsychiatric state, for example as further described below.

The method 500 may further include, at 508, regressing the averaged brain state indicator to the independently derived behavioral, psychological and/or physiological measures of mood or neuropsychiatric state. The method 500 may further include, at 510, automatically selecting regression parameters that minimize at least one of error or sensitivity of the regression model in the decoding of the mood or neuropsychiatric states. The method 500 may further include recording in a computer-readable medium (such as a non-transitory memory) a definition of the selected predictive network, the state space model parameters, and the regression parameters for use in decoding a mood or neuropsychiatric state from large-scale multisite brain activity (or in the special case, single-site activity) of the subject.

Figure 6:
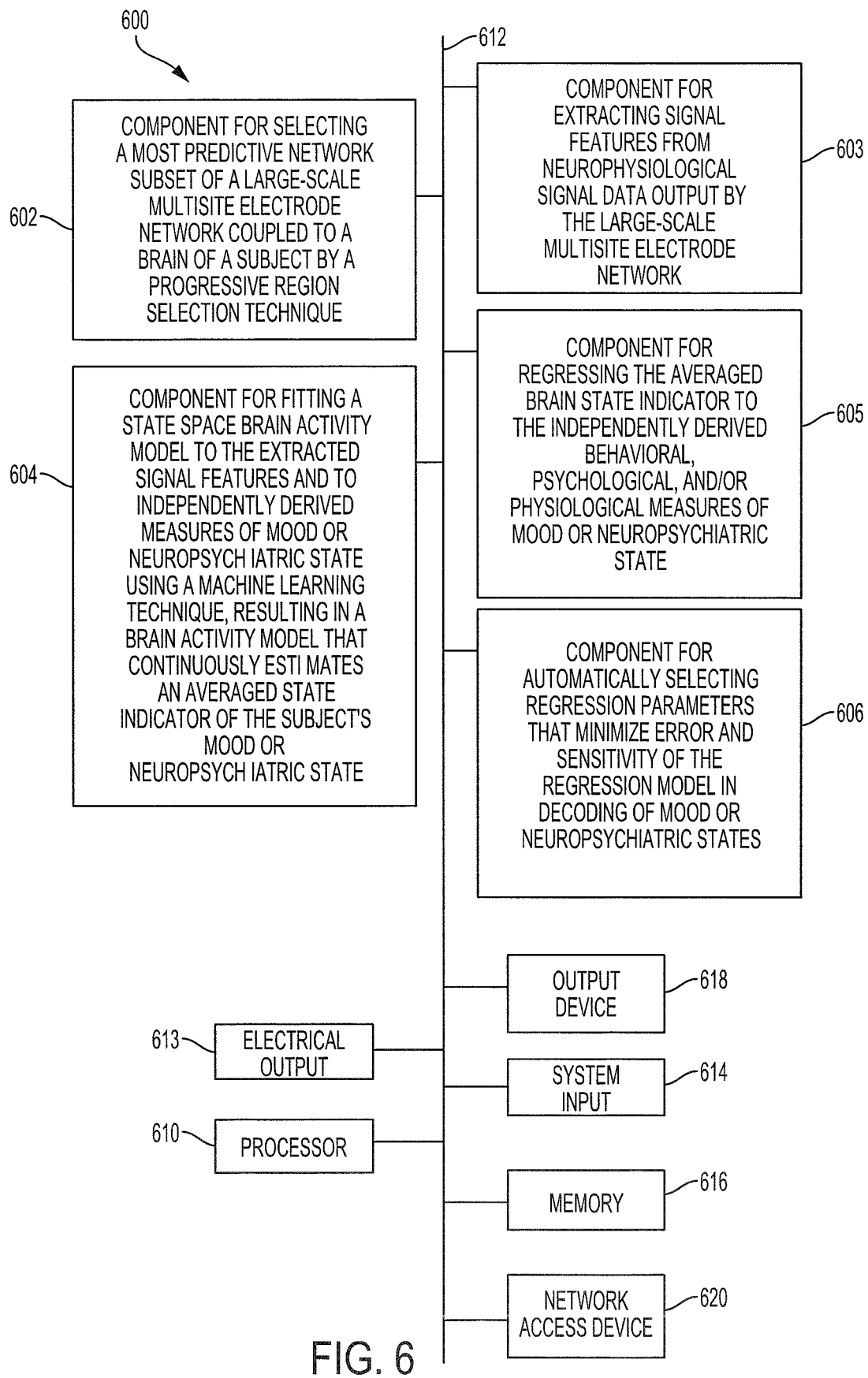
FIG. 6 illustrates a system for enabling decoding of mood or neuropsychiatric state from large-scale multisite brain activity (or in the special case, single-site activity) using a state space brain activity model that estimates a mood or neuropsychiatric state of a subject according to an embodiment of the present disclosure.

FIG. 6 is a block diagram illustrating components of an apparatus or system 600 for enabling decoding of mood or neuropsychiatric state from large-scale multisite brain activity (or in the special case, single-site activity) using a state space brain activity model that estimates a mood or neuropsychiatric state of a subject from contemporaneous neurophysiological signal data. The apparatus or system 600 may include additional or more detailed components for performing functions or process operations as described herein. As depicted, the apparatus or system 600 may include functional blocks that can represent functions implemented by a processor, software, or combination thereof (e.g., firmware), such as by one or more of a processor 610 or a non-transitory memory 616.

As illustrated in FIG. 6, the apparatus or system 600 may comprise an electrical component 602 for selecting a most predictive network subset of a large-scale multisite electrode network coupled to a brain of a subject by a progressive region selection technique. The component 602 may be, or may include, a means for said selecting. Said means may include the processor 610 coupled to the memory 616, the processor 610 executing an algorithm based on program instructions stored in the memory 616, or the like. Such algorithm may include a sequence of more detailed operations, for example, as described below.

The apparatus 600 may further include an electrical component 603 for extracting signal features from neurophysiological signal data output by the large-scale multisite electrode network. The component 603 may be, or may include, a means for said extracting. Said means may include the processor 610 coupled to the memory 616, the processor 610 executing an algorithm based on program instructions stored in the memory 616, or the like. Such algorithm may include a sequence of more detailed operations, for example, accessing a signal feature definition, digitizing the neurophysiological signal data output, and applying the feature definition to the digitized neurophysiological signal data output, or the like.

The apparatus 600 may further include an electrical component 604 for fitting a state space brain activity model to the extracted signal features and to independently derived measures of mood or neuropsychiatric state using a machine learning technique, resulting in a brain activity model that continuously estimates an averaged state indicator of the mood or neuropsychiatric state of the subject. The component 604 may be, or may include, a means for said fitting. Said means may include the processor 610 coupled to the memory 616, the processor 610 executing an algorithm based on program instructions stored in the memory 616, or the like. Such algorithm may include a sequence of more detailed operations for fitting, for example as explained below.

The apparatus 600 may further include an electrical component 605 for regressing the averaged brain state indicator to the independently derived behavioral, psychological, and/or physiological measures of mood or neuropsychiatric state. The component 605 may be, or may include, a means for said regressing. Said means may include the processor 610 coupled to the memory 616, the processor 610 executing an algorithm based on program instructions stored in the memory 616, or the like. Such algorithm may include a sequence of more detailed operations, for example, any regression technique as described more fully below.

The apparatus 600 may further include an electrical component 605 for automatically selecting regression parameters that minimize error and sensitivity of the regression model in decoding of mood or neuropsychiatric states. The component 605 may be, or may include, a means for said parameter selecting. Said means may include the processor 610 coupled to the memory 616, the processor 610 executing an algorithm based on program instructions stored in the memory 616, or the like. Such algorithm may include a sequence of more detailed operations, for example, any selection technique as described more fully below.

The apparatus 600 may optionally include a processor 610. The processor 610 may be in operative communication with the components 602-606 via a bus 612 or similar communication coupling. In the alternative, one or more of the components 602-606 may be instantiated as functional components in a memory of the processor 610 (e.g., the processor 610 may be an ASIC). The processor 610 may effect initiation and scheduling of the processes or functions performed by electrical components 602-606.

In some embodiments, the apparatus or system 600 may include a system input port 614 for receiving the neurophysiological signal data output from an electrode array couple to the brain of the subject. The apparatus may further include an output port for electrical signals or data 613, for example a network access device 620 operable for communicating with system components over a computer network, or an output device 618 (such as a display, a touchscreen, a speaker, or the like). A network access device 620 may be, or may include, for example, an Ethernet port or serial port (e.g., a Universal Serial Bus (USB) port), a Wi-Fi port, a Bluetooth port, or the like. In some embodiments, the apparatus or system 600 may optionally include a component for storing information, such as, for example, a non-transitory memory 616.

The computer readable medium or the memory 616 may be operatively coupled to the other components of the apparatus 600 via the bus 612, or the like. The memory 616 may be adapted to store computer readable instructions and data for effecting the processes and behavior of the components 602-606, and subcomponents thereof, or the processor 610, or the method 500 and one or more of the additional operations disclosed herein. The memory 616 may retain instructions for executing functions associated with the components 602-606. While shown as being external to the memory 616, it is to be understood that the components 602-606 can exist within the memory 616 or an on-chip memory of the processor 610, or hard-wired into the processor 610 (e.g., if the processor 610 is an ASIC).

The network access device 620 may be designed as a wireless transmitter/receiver, or a wired transmitter/receiver, for transmitting and receiving a communication signal to/from another system component such as, for example, a server or client device. In some embodiments, the processor 610 may include networked microprocessors from devices operating over a computer network. In addition, the apparatus 600 may include any suitable output device 618 and input device 614 for interaction with a user.

Experimental Results

As experiments, continuously recorded large-scale intracranial activity was recorded from 7 human subjects with epilepsy across multiple days and simultaneously self-reported mood state measurements was collected. The recordings covered multiple limbic regions including the OFC, ACC, INS, AMYG, and HPC, as well as other regions in frontal, temporal, and parietal cortices.

Subjects' mood state was measured at discrete times during multiple days of neural recording using a validated tablet-based self-report questionnaire termed the IMS (12 plus or minus 2.4 IMS points, i.e., reports, across 6.0 plus or minus 4.5 days per subject; mean plus or minus standard deviation). IMS provides a momentary assessment of a set of mood states related to depression and anxiety symptoms and served as the operational definition of mood for developing interventional decoders. IMS score is based on sum of answers to 24 questions and lies between −72 to 72. IMS variations covered 73% of the total possible IMS range across the subjects and 33% plus or minus 7.2% (and at least 25%) of this range within each subject, reflecting meaningful mood state variations over multiple recording days.

The experiments aimed to build a decoder for each subject that generalized to prediction of a new IMS point. As the main neural features, powers were selected in various frequency bands, $\delta+\theta$ (1-8 Hz), $\alpha$ (8-12 Hz), $\beta$ (12-30 Hz), $\gamma_1$ (30-55 Hz), and $\gamma_2$ (65-100 Hz). Neural features were high-dimensional (224 plus or minus 99 features). The method could also use other neural features such as coherence features (detailed below). Since IMS points are sparse due to difficulties of mood assessment, training a generalizable decoder presents a challenging modeling problem. The decoders were evaluated using a rigorous leave-one-out cross-validation in which an IMS point was left out to be predicted (test IMS) and the rest of the IMS points (train IMS) were used to train the decoder; this cross-validated train-test procedure was repeated for all IMS points. The test IMS was never seen by any step of decoder training. Thus, if the decoder overfitted to the sparse train IMS, it would not generalize to the test IMS and would consequently fail for decoding in cross-validation.

Neural decoders of mood state were built for each subject. It was found that in each of the 7 subjects, the decoders were significantly predictive of the IMS points according to both evaluation tests ($P \leq 0.05$ for all subjects; all P values were corrected with false discovery rate (FDR) control if needed). The decoders were also highly predictive of the IMS points at the population level (random-test $P=3.8\times10^{-12}$ and permuted-test $P=1.1\times10^{-15}$). Finally, the robustness of the modeling framework to the choice of neural features was confirmed by decoding IMS using coherence features. These results suggest that the framework can tap into distributed neural representations to decode mood state.

Figure 7:
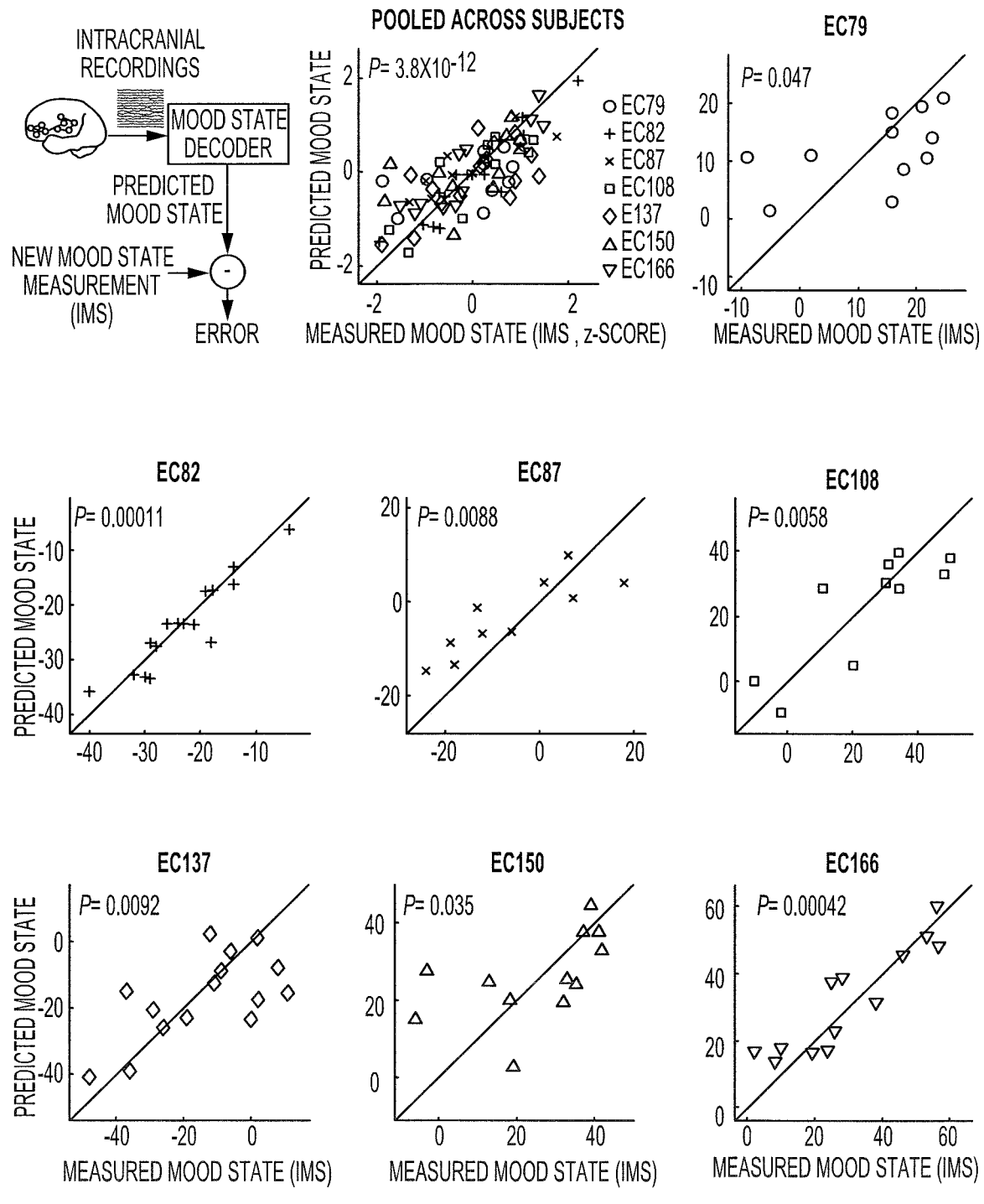
FIG. 7 illustrates a decoding process and results for decoding a mood state from neural activity in each of multiple subjects of experiments according to an embodiment of the present disclosure.

FIG. 7 illustrates that mood state may be decoded from neural activity in each subject. In particular, FIG. 7 illustrates (a) an overview of the decoding process. The decoder can process the intracranial recordings causally over time to predict mood state. At discrete time-points when a new mood state measurement is available, the subtraction of the predicted mood state from the measured mood state gives the prediction error. (b) Cross-validated prediction of the mood state is shown against the true measured mood state, pooled across subjects in (b) and within individuals in (c-i). Random-test P value is noted on each plot ($P<0.05$ for all after FDR correction). The present disclosure provides a modeling framework (described above and below) that was used to build subject-specific mood state decoders using multi-site intracranial recordings in 7 subjects. It is shown that the decoders predicted mood state variations over multiple days in each subject. The decoders largely recruited networks within the limbic regions to predict mood state. In addition, temporal changes in the spectro-spatial features within these networks were tuned to mood state variations and the decoder aggregated information across these features to predict mood state (more details below). Although the experiments focused on mood, the modeling framework can also be used to decode other neuropsychiatric states, such as anxiety or fear or pain.

FIG. 8 is a table illustrating cross-validated IMS prediction accuracy of the mood state decoders and the spatial distribution of the best small mood-predictive networks.

The decoders could generalize across time. The time-delay between the first and the last IMS points was on average 6 days and between consecutive IMS points was on average 13 hours. Since an IMS point that is decoded is not used for training the decoder (cross-validation), the decoders could generalize across hours and days. Further, even IMS points that were the only report obtained in a day were significantly predicted across subjects (random-test, $P=1.4\times10^{-3}$). Moreover, the time-distance from a test IMS to the closest train IMS was not correlated with its prediction error (Spearman's $P=0.99$ across the population and $P>0.15$ in every subject).

Figure 9:
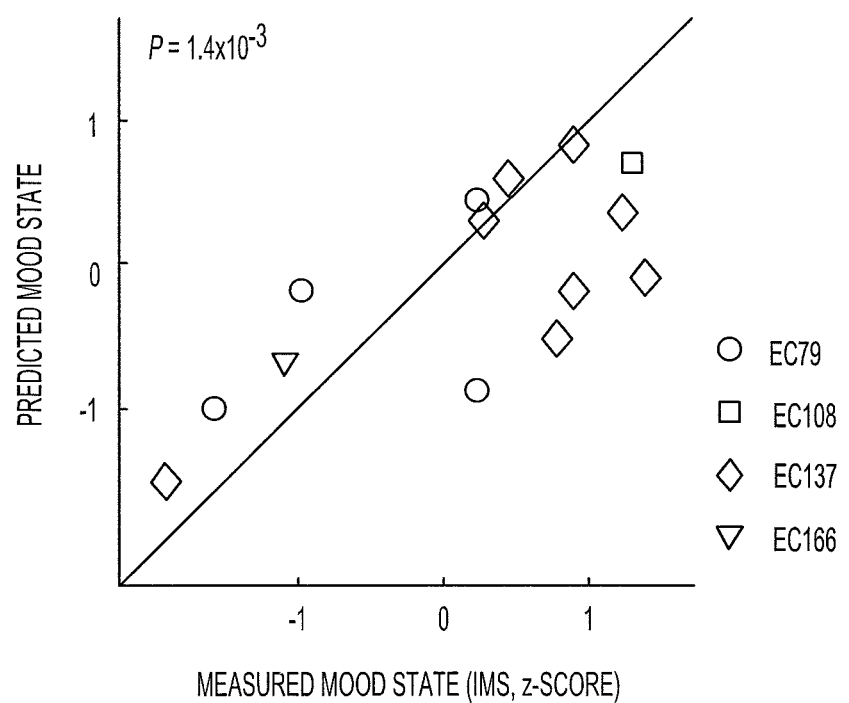
FIG. 9 illustrates decoders generalized from day-to-day according to an embodiment of the present disclosure.

FIG. 9 illustrates the decoders as generalized from day to day. Prediction of IMS points that were the only IMS point (i.e., report) obtained in a day was significant across subjects. The cross-validated IMS predictions in each subject are z-scored based on the mean and standard deviation of all true IMS points in that subject. Then z-scored predictions of the IMS points that were the only IMS point in a day were pooled together across all 4 subjects that had such IMS points. The same procedure was applied to sets of random IMS points to find the random-test P value.

The decoders could also generalize across a wide range of IMS. First, in cross-validation, the decoders could predict IMS variations that covered 73% and 33% plus or minus 7.2% of the total possible IMS range across the subjects and within individuals, respectively. Also, the minimum and the maximum IMS points in each subject could be decoded, which were outside the range of train IMS due to cross-validation (random-test $P=1.3\times10^{-6}$).

Figure 10:
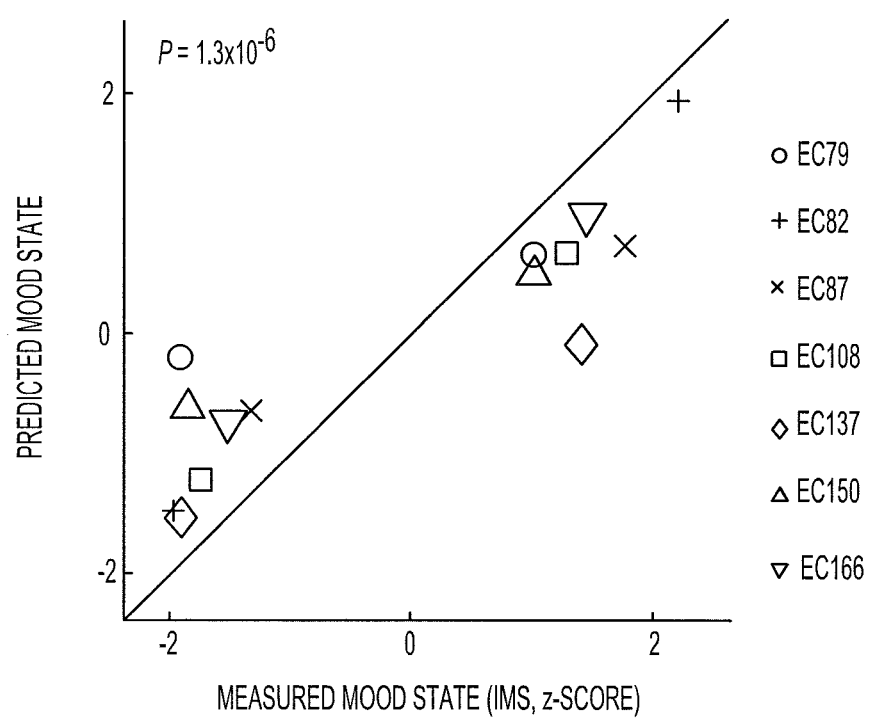
FIG. 10 illustrates that decoders may significantly predict maximum and minimum IMS values in each of multiple subjects of experiments according to an embodiment of the present disclosure.

FIG. 10 illustrates that the decoders could significantly predict the maximum and minimum IMS values in each subject, which were outside the range of IMS values used for decoder training. The cross-validated IMS predictions from each subject are z-scored based on mean and standard deviation of all true IMS points in that subject. Then the z-scores of the maximum and minimum IMS predictions in each subject were pooled across the population. The same procedure was applied to sets of random IMS points to find the random-test P value.

Figure 11:
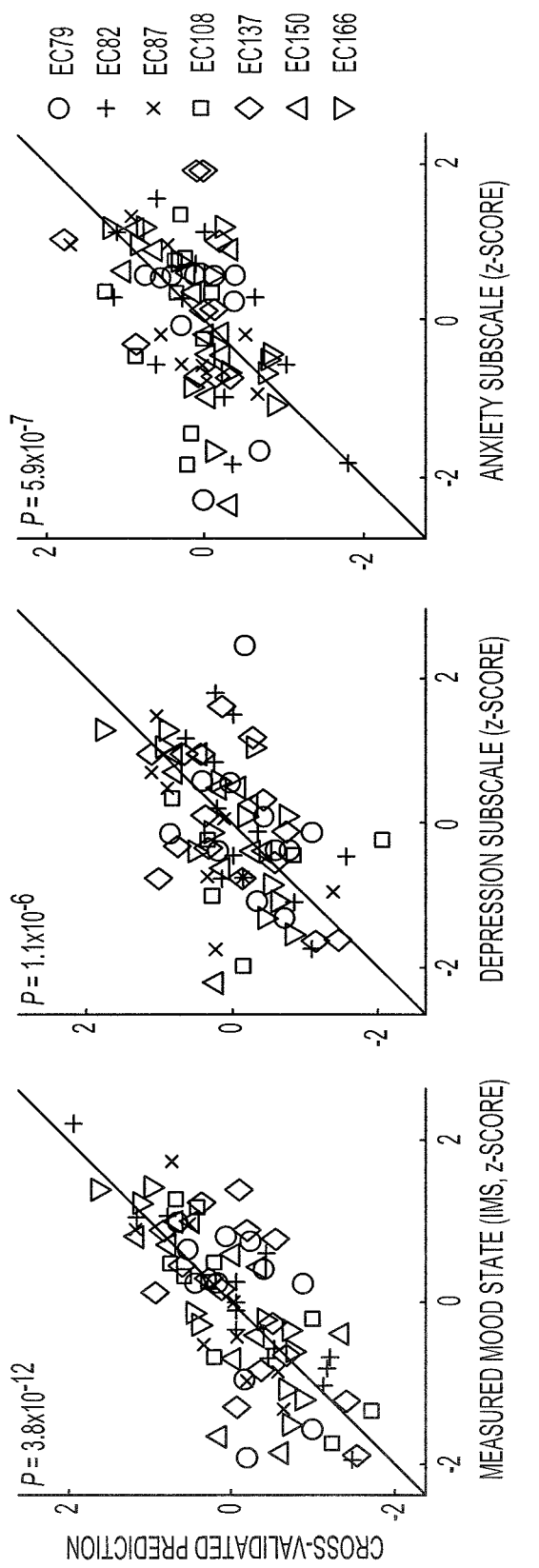
FIG. 11 illustrates that IMS depression and anxiety subscales could also be separately decoded using the same method and networks that were selected for decoding full IMS values according to an embodiment of the present disclosure.

Further, the same cross-validated modeling framework could separately decode the depression and anxiety subscales of IMS using the same method and networks that were predictive of the total IMS (random-test $P=1.1\times10^{-6}$ and $P=5.9\times10^{-7}$ across subjects, respectively), as shown in FIG. 11.

As a control, it was found that interictal discharge rates in the selected networks used for decoding were not significantly predictive of mood state in any subject ($P>0.18$ for random-test and permuted-test in all subjects). Taken together, these results show that the decoders can predict mood state variations from neural activity across multiple days of recordings in each subject.

FIG. 11 illustrates that IMS depression and anxiety subscales could also be separately decoded using the same method and the same networks selected for decoding the full IMS. IMS depression and anxiety subscales consist of 7 and 5 of the total 24 questions, respectively. Within cross-validation, the regression model was retrained to predict the IMS depression and anxiety subscales separately in each subject. The network, number of PCs and neural state dimension were fixed to be the same as those selected for decoding the full IMS. Despite the smaller number of questions and thus potentially a lower subscale measurement signal-to-noise ratio, the IMS depression and anxiety subscales could be significantly decoded across subjects using the same networks that were predictive of the full IMS. Cross-validated predictions were pooled across subjects by z-scoring using the true value of the scale in each subject. Cross-validated predictions versus the true value of the scales are shown for full IMS in (a), IMS depression subscale in (b), and IMS anxiety subscale in (c). The random-test P value in each case is noted on the figure and is significant in all cases. Performing a search of network, number of PCs and neural state dimensions for each IMS subscale separately led to similar results. This illustrates that the decoding technology can be applied to other neuropsychiatric states, such as anxiety scale in addition to mood.

It was found that decoding mood state was possible largely using networks within the limbic regions. In the main analysis, progressive region selection first searched only the limbic regions given their important role in mood representation. Only if the limbic regions alone were not sufficient for decoding, the method then searched all available regions (while using FDR correction). In 6 of 7 subjects, networks within the limbic regions alone were significantly predictive of mood state and only in one subject (EC137), progressive region selection proceeded to search all regions to achieve significant prediction.

Figure 12:
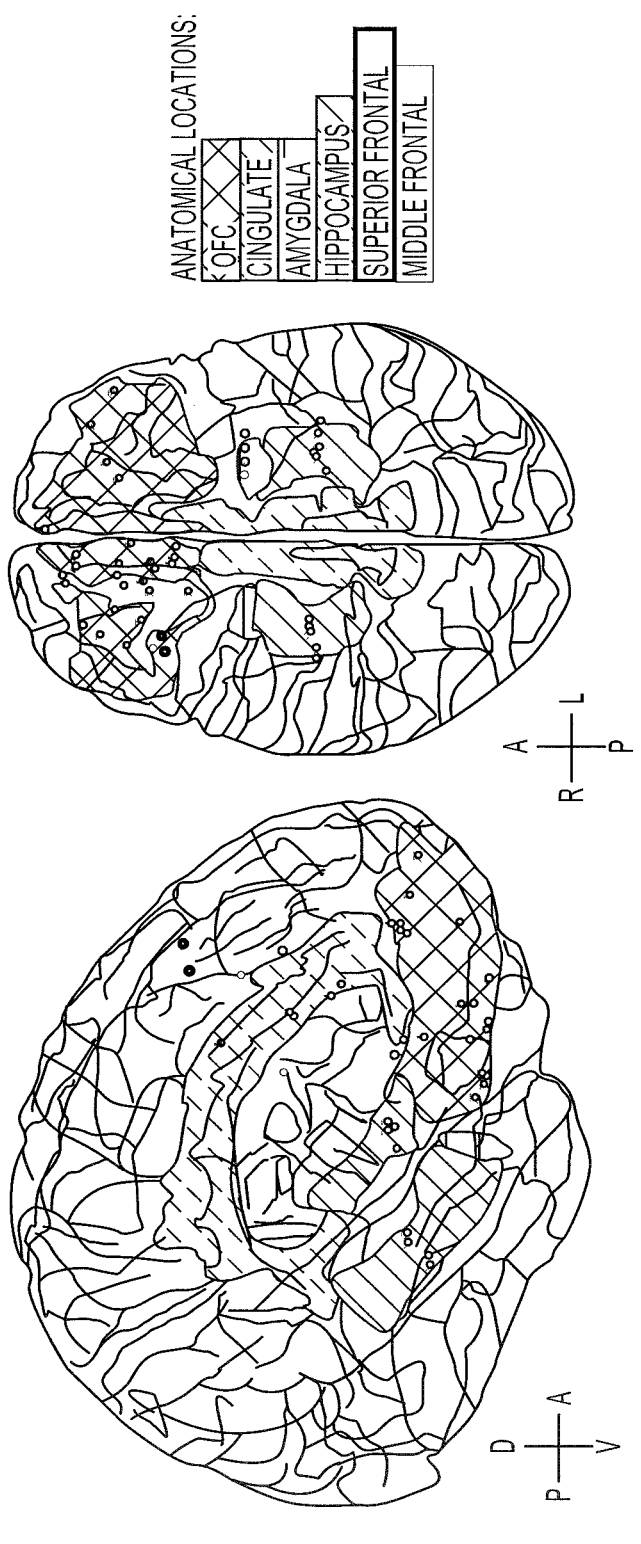
FIG. 12 illustrates that mood predictive networks selected for decoding were largely within the limbic regions in all subjects of experiments according to an embodiment of the present disclosure.
Figure 13:
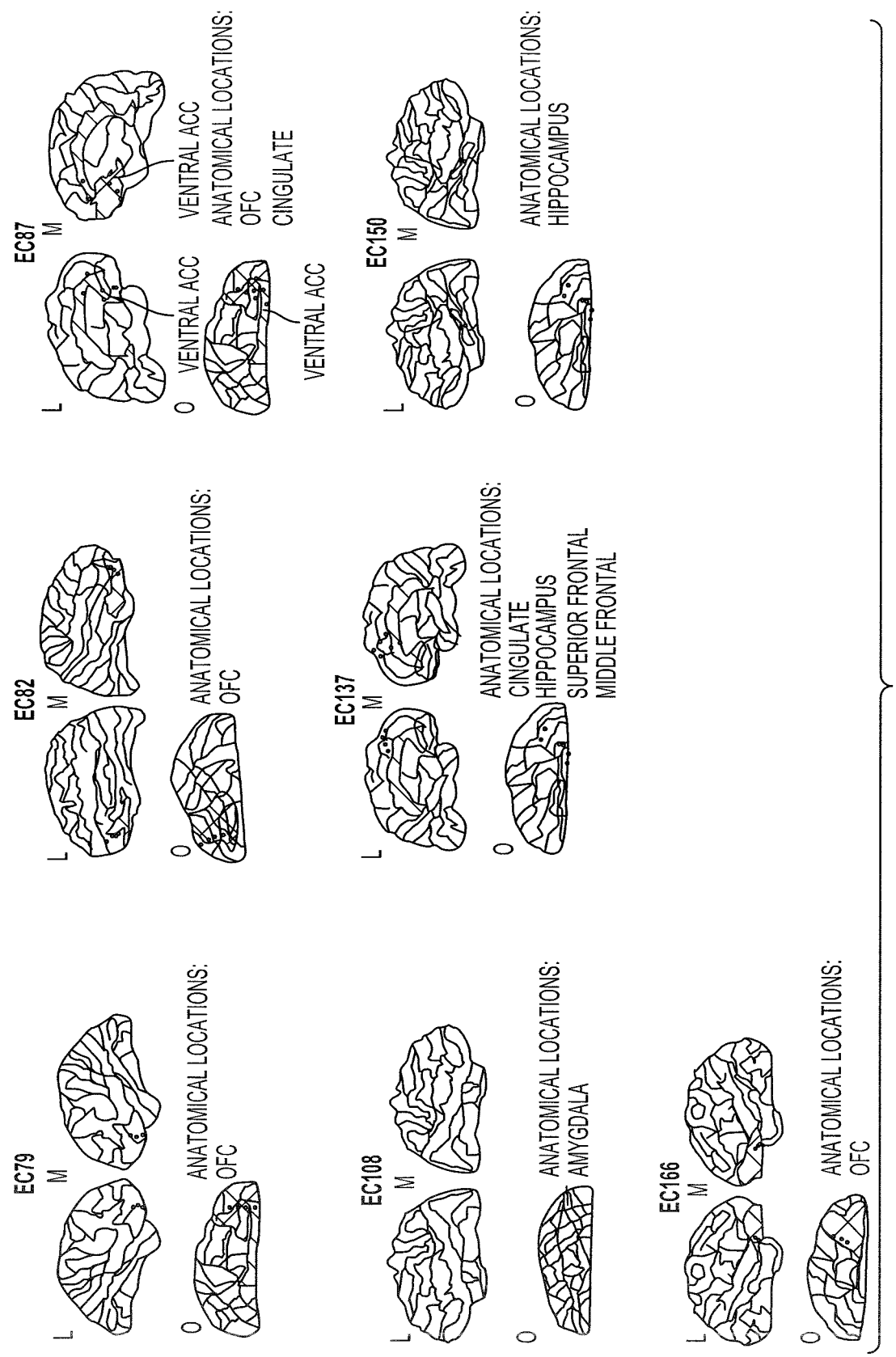
FIG. 13 illustrates that limbic regions alone were sufficient for decoding mood state in nearly all subjects of experiments according to an embodiment of the present disclosure.

The main analysis above established the significance of decoding and found the smallest network size that was sufficient for decoding in each subject. In each subject, the best mood-predictive network with that size was then identified. FIG. 12 illustrates that mood-predictive networks selected for decoding were largely within the limbic regions in all subjects. The location of all recording channels included in the best small mood-predictive network for decoding in each subject are shown on the standard Montreal Neurological Institute template brain. Anterior (A), posterior (P), dorsal (D), ventral (V), left (L) and right (R) directions are indicated on the figure. The areas corresponding to key limbic regions based on labeling from the FreeSurfer software are marked. Each recording channel is also marked with the marking of the anatomical region to which it is assigned. All displayed cingulate coverage was in dorsal anterior cingulate cortex (ACC), except for one intracranial electrode in EC87 which is marked as ventral ACC on the figure. FIG. 13 shows the networks selected for each subject.

FIG. 13 illustrates that limbic regions alone were sufficient for decoding mood state in all subjects except just EC137, whose decoding still required the limbic regions. The best small mood-predictive network sufficient for decoding in each subject is shown in (a-g). In each panel, lateral (L), medial (M) and orbital (O) views of the brain are shown. The areas corresponding to key limbic regions based on labeling from the FreeSurfer software are shaded. Each recording channel is also marked with the anatomical region to which it is assigned based on FreeSurfer labels and expert examination (with the latter having priority in case of any difference). All displayed cingulate coverage was in dorsal ACC, except for one intracranial electrode in EC87 which is marked as ventral ACC on the figure.

Interestingly, the most commonly recurring region was OFC, which was included in the network in 4 of 7 subjects. OFC alone was selected in EC79, EC82 and EC166, and a distributed network with OFC and ACC was selected in EC87. In EC108 and EC150, AMYG and HPC were selected, respectively. Finally, in EC137 the selected network consisted of limbic regions ACC and HPC together with an ECoG electrode covering the middle and superior frontal gyri (dorsolateral and dorsomedial prefrontal cortex), which have also been implicated in mood representation. These results suggest that using a subset of regions that belong to the distributed mood-representation networks is sufficient for decoding. Indeed, progressive region selection stops adding more regions as soon as significant prediction is achieved, and does not attempt to identify all mood-predictive regions.

Figure 14:
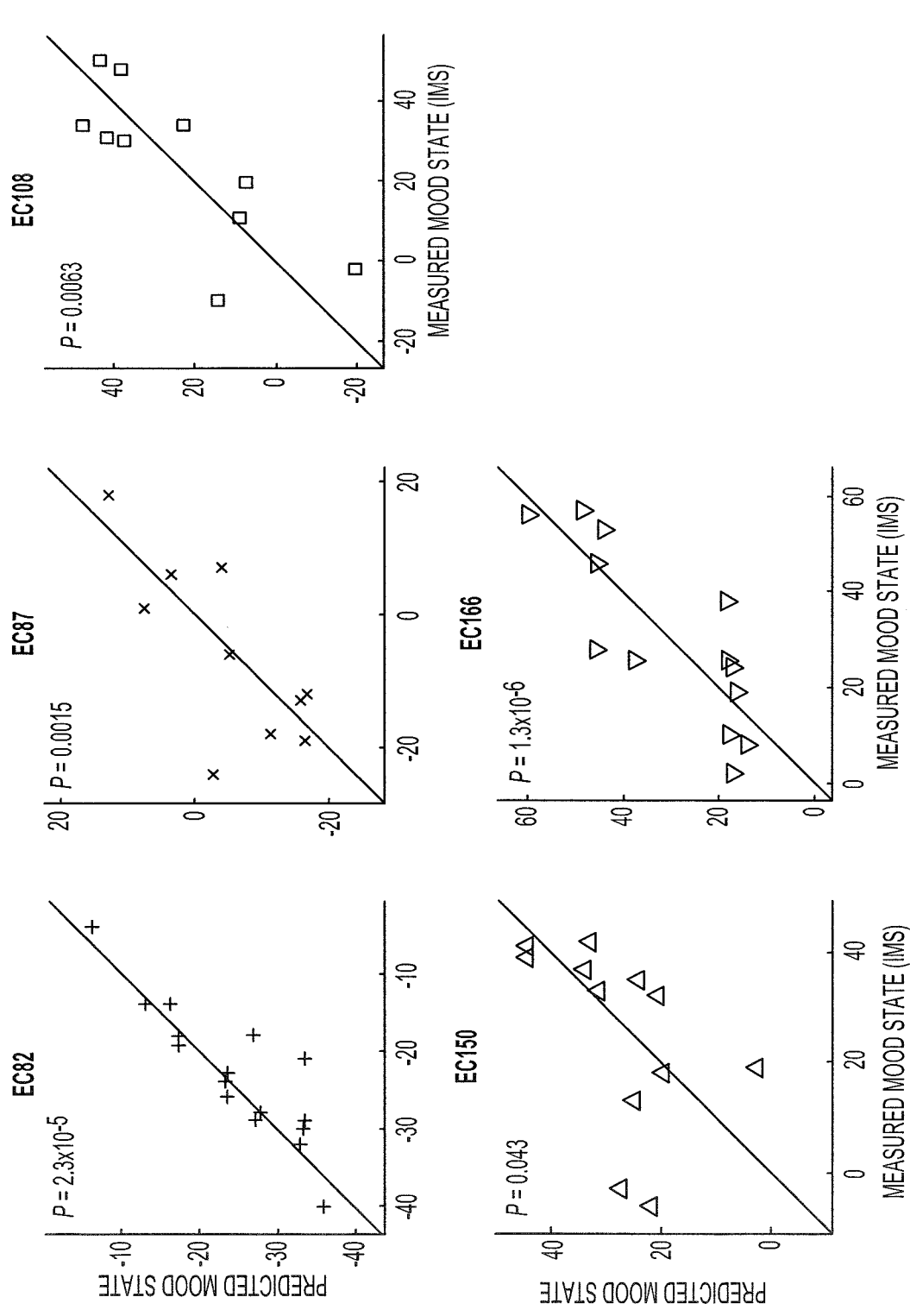
FIG. 14 illustrates that extending modeling and searching all regions robustly decoded mood state variations in nearly all subjects according to an embodiment of the present disclosure.

Two additional analyses further confirmed the role of limbic regions. First, the methods searched across all electrodes for every subject. FIG. 14 illustrates that extending the modeling and search to all regions robustly decoded mood state variations in 6 subjects. Random-test $P<0.05$ for all after FDR correction.

Figure 15:
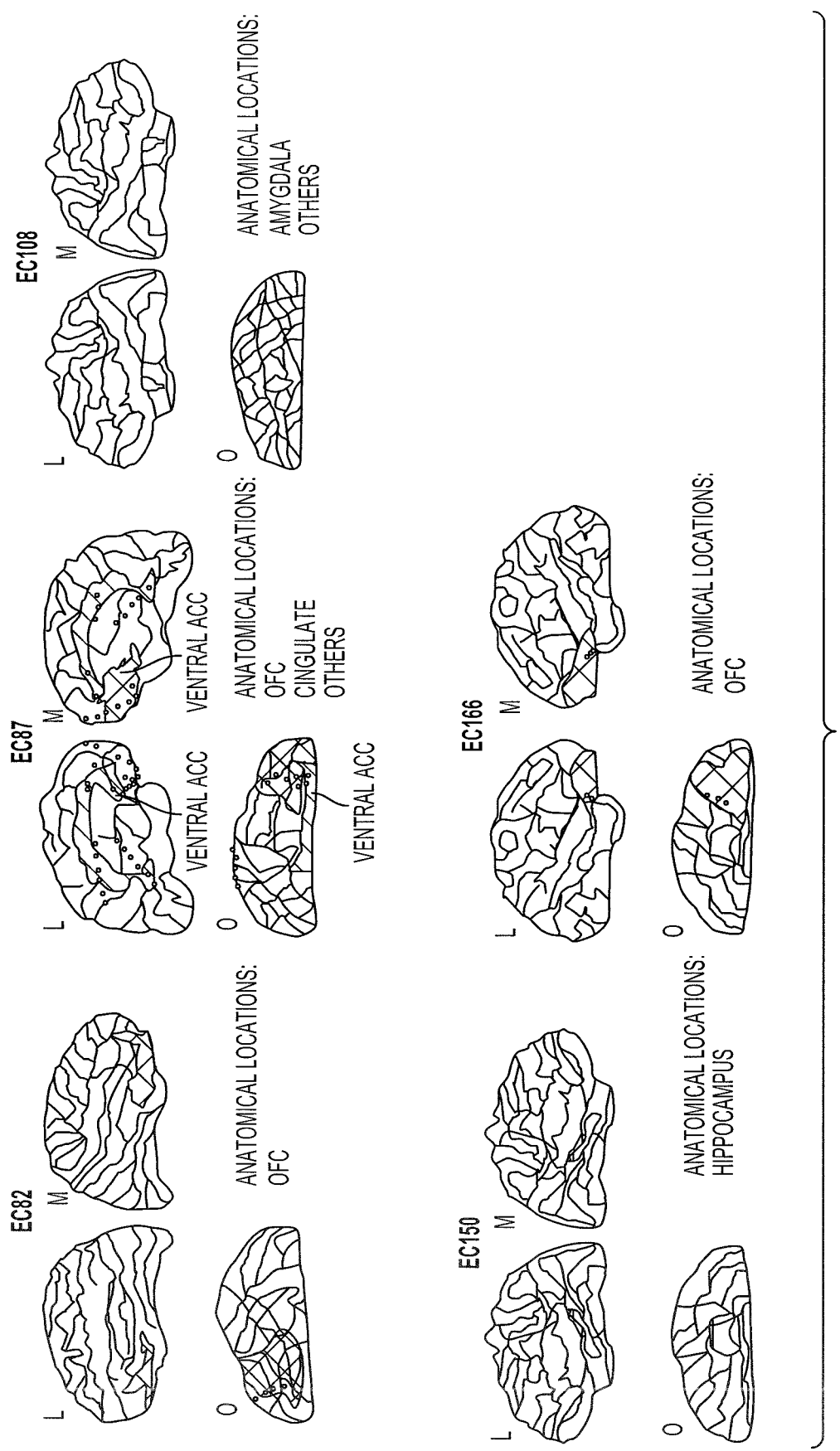
FIG. 15 illustrates that extending a search to all regions typically resulted in selection of the same regions as a search limited to only limbic regions according to an embodiment of the present disclosure.

Even without knowing where these electrodes were, our modeling framework largely selected the same regions for decoding as those selected in the limbic search. When searching among all electrodes and without knowing where these electrodes are, the modeling framework consistently selects the same limbic regions for decoding as the ones selected in the limbic search. FIG. 15 illustrates that extending the search to all regions consistently and robustly selected the same regions as those selected in a search within the limbic regions alone. Note that in EC108, the same AMYG electrode as the limbic search was selected; this electrode had some channels (indicated in black) that were not verified as being exactly in AMYG and thus were not included in the limbic search but were included in the all-region search.

FIG. 14 illustrates that extending the modeling and search to all regions robustly decoded mood state variations in 6 subjects. Random-test $P<0.05$ for all after FDR correction.

Second, it was found that decoding largely failed when searching within electrodes outside the limbic regions (subjects included had similar number of neural features inside and outside limbic regions).

Figure 16:
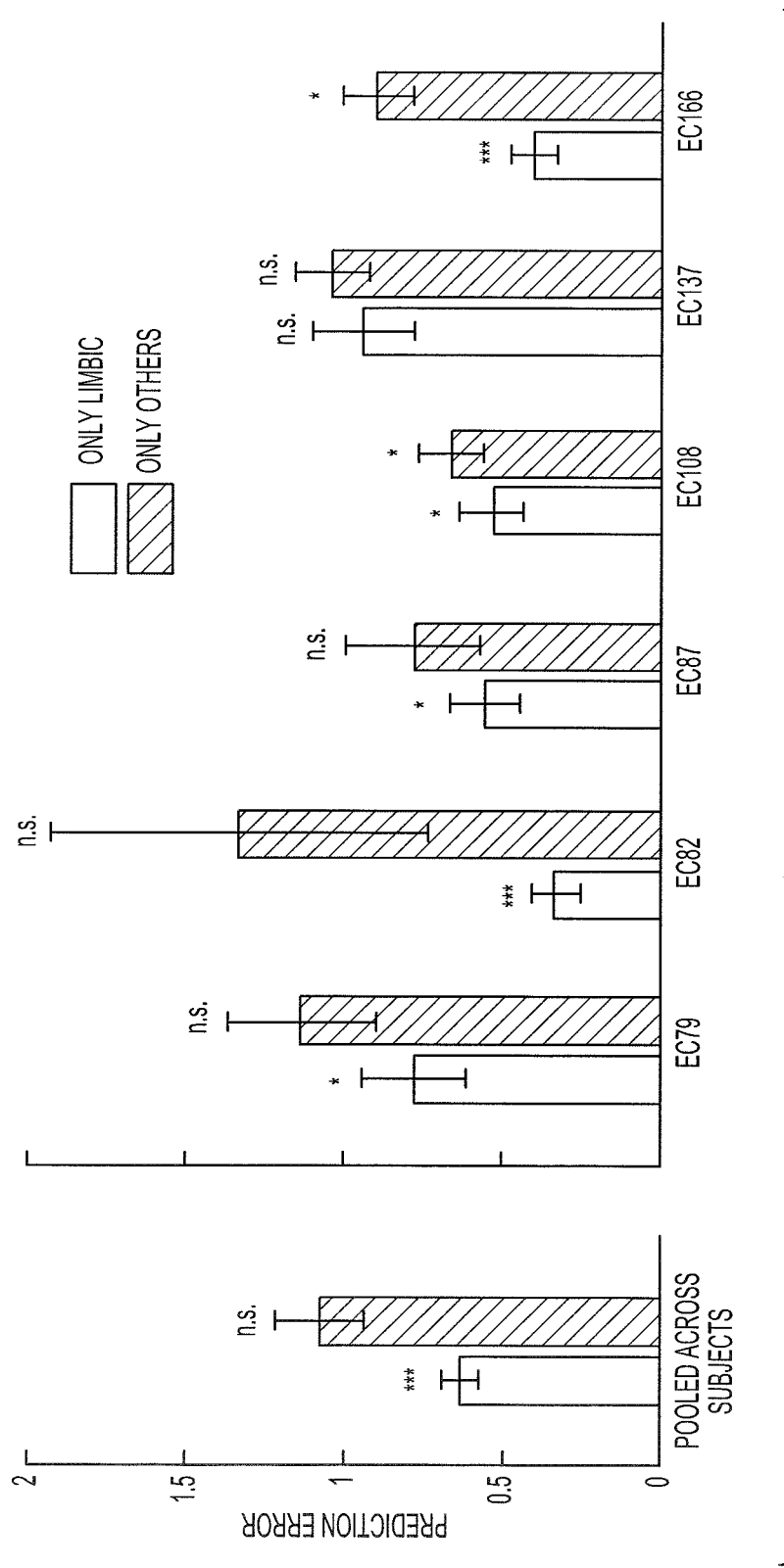
FIG. 16 illustrates mood state decoding with and without inclusion of limbic regions according to an embodiment of the present disclosure.

FIG. 16 illustrates that mood state decoding without limbic regions failed in most subjects. The cross-validated normalized mean-absolute error is shown when using only limbic regions or using only other regions for decoding across the population in (a) and in each individual in (b). This analysis was performed for the 6 subjects that had similar number of neural features inside (97 plus or minus 54) and outside (96 plus or minus 48) limbic regions (two-sided t-test $P=0.98$). Bars represent mean and error bars represent s.e.m. Number of samples in (a) is 75 (total number of IMS points across the 6 subjects) and in (b) is equal to the number of IMS points for each subject. (a) illustrates that decoding with features outside limbic regions failed at the population level. (b) illustrates that in 4 of the 6 subjects, decoding was not significant without the limbic regions; only in EC108 and EC166, a mood-predictive network was identified outside the limbic regions in both cases consisting of inferior temporal cortex, which has been implicated in prior studies as mood-relevant. Significance caption: n.s. (not significant), random-test $P>0.05$; *, random-test $P<0.05$; , random-test $P<0.005$; *, random-test $P<0.005$.

These results further validate the modeling because they are biologically consistent with prior neuroimaging studies that indicate the central role of distributed limbic regions in emotion and mood representation. Taken together, the decoders robustly recruited the limbic regions to decode mood state in all subjects.

To show the biological consistency and robustness of the modeling framework, the selected regions in the decoders were examined. It was found that the decoders recruited networks within the limbic regions in each subject, consistent with prior imaging studies that show the key role of limbic regions in mood representation. Using only the limbic regions was sufficient for decoding mood state in all subjects except just one. In contrast, without the limbic regions, decoding largely failed. Moreover, when searching all regions, in each subject, the methodology largely selected the same regions for decoding as those selected in the limbic search, showing robustness in selecting mood-predictive regions. Finally, all the selected limbic regions in the decoders (i.e., OFC, ACC, AMY, HPC) have been implicated in mood and emotion representation, for example for population level state classification.

While some limbic regions were consistently selected across some subjects, for example OFC in 4 of the 7 subjects, there was also variability in the selected limbic regions across subjects. There are multiple potential reasons for this variability. First, across subjects, there were differences in where the electrodes were implanted, and in the mood state ranges—multiple neuroimaging studies have suggested that different limbic regions may have differential roles in positive and negative mood state representation. These inter-subject variabilities may have contributed to region variability. Second, critically, to address the modeling challenge caused by the sparsity of mood state measurements, a key idea in the methodology was to identify and model only the smallest subset of regions that was sufficient for decoding in each subject. This allowed obtaining a less complex model that could be robustly fitted with the available train data (progressive region selection). Importantly, it was not attempted to find all mood-predictive regions. Instead, given the evidence that mood is represented across multiple distributed brain regions, it was hypothesized that decoding may still be possible with only modeling and using a subset of these regions. For the above reasons, there likely exist additional mood-predictive regions in a given subject. Thus, the selected regions should be interpreted as the best small networks sufficient for decoding in a subject (given their available electrode coverage), not as the only mood-predictive regions in that subject. Future chronic studies with more mood measurements may enable an exhaustive investigation of mood-predictive regions across different subjects, which may guide the choice of recording sites and electrode placement in future closed-loop therapies.

Figure 17:
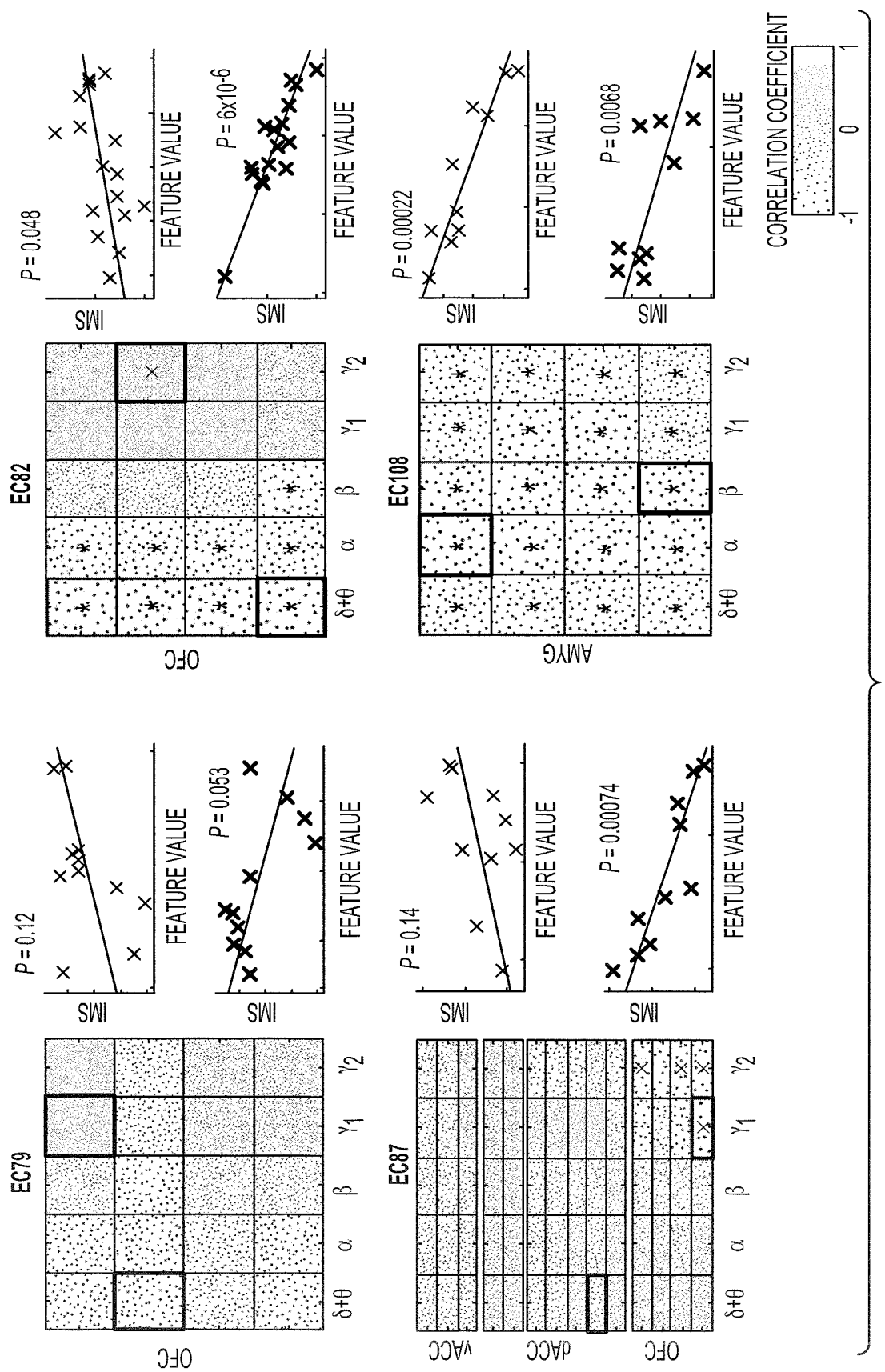
FIG. 17 illustrates spectro-spatial features within mood-predictive networks in each of multiple subjects of experiments according to an embodiment of the present disclosure.
Figure 17:
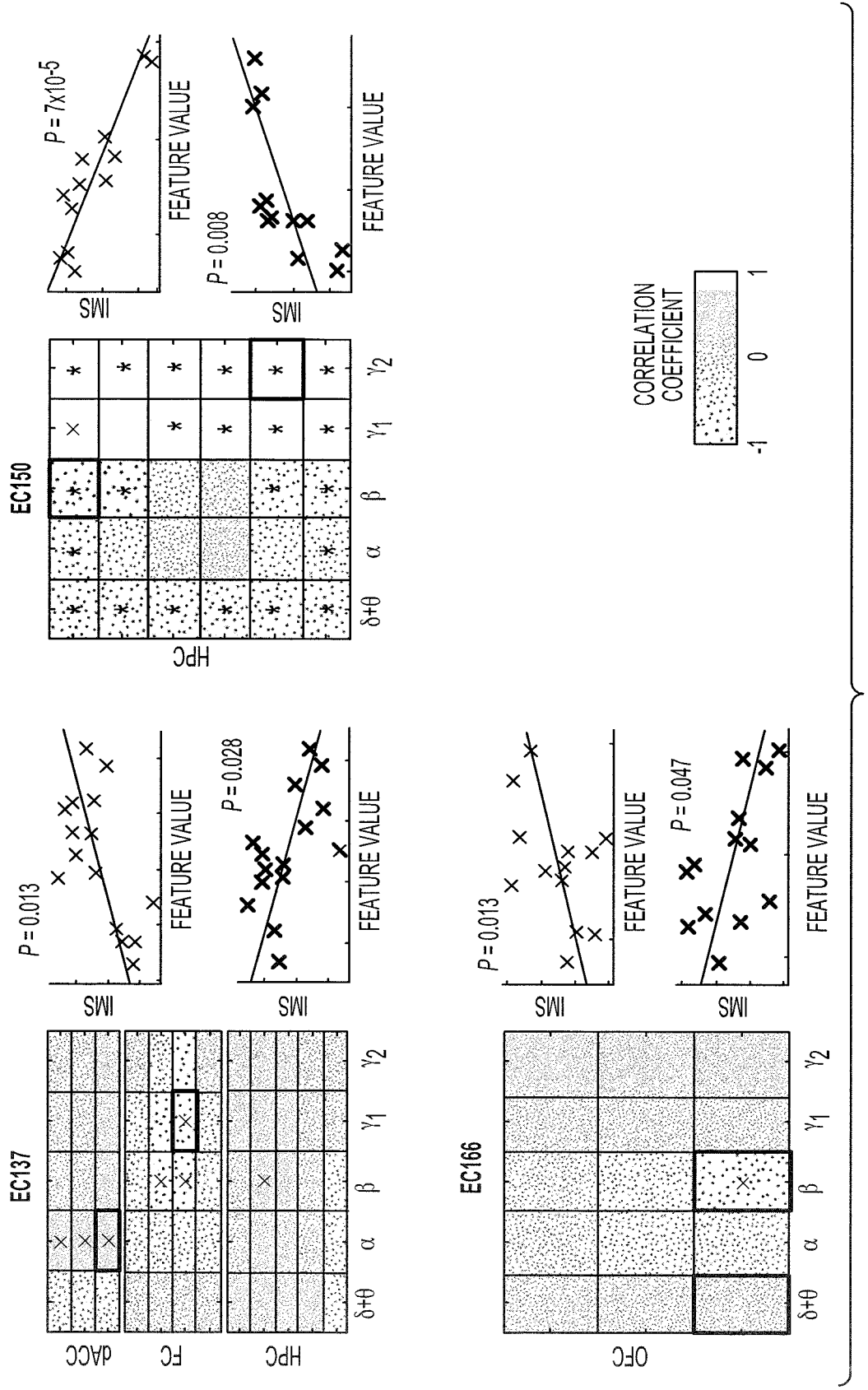

The spectro-spatial neural features within the identified mood-predictive networks (i.e., powers at different channels and frequency bands) were tuned to mood state variations over time. FIG. 17 illustrates that spectro-spatial features within the mood-predictive networks were tuned to mood state variations over time. Correlation of all individual features included in the best small mood-predictive network for decoding in each subject (a-g). The horizontal axes show the frequency bands. The vertical axes show the recording channels (recording channels from different regions are shown on separate plots). The plots indicate the correlation coefficient value. A positive correlation indicates that feature value increases with an increase in the IMS (better mood) and a negative correlation indicates that the feature value increases with a decrease in the IMS (worse mood). Features with Pearson's P value less than 0.05 are marked with an asterisk if they remain significant after FDR multiple comparison correction controlled at 0.05 and with a cross otherwise. For each subject, two samples (boxed) of tuned feature variations with IMS are plotted on the right (scheme consistent with the correlation plot). Pearson's correlation P value is noted for each plot.

Certain individual features in all 5 frequency bands had strong correlations with IMS, some of which were significant even after FDR correction ($P<0.05$ after FDR correction). All these significantly tuned features in low frequencies ($\delta+\theta$, $\alpha$ and $\beta$) were negatively correlated with IMS. In contrast, the significantly tuned features in high frequencies had both positive and negative correlations with IMS. These results suggest that the decoder predicted mood state by combining information across spectro-spatial features. Consistently, the prediction error when using all 5 frequency bands was significantly lower compared with using single frequency bands alone ($P<0.05$, one-sided Wilcoxon signed-rank test), suggesting that all frequency bands could contribute to decoding.

Figure 18:
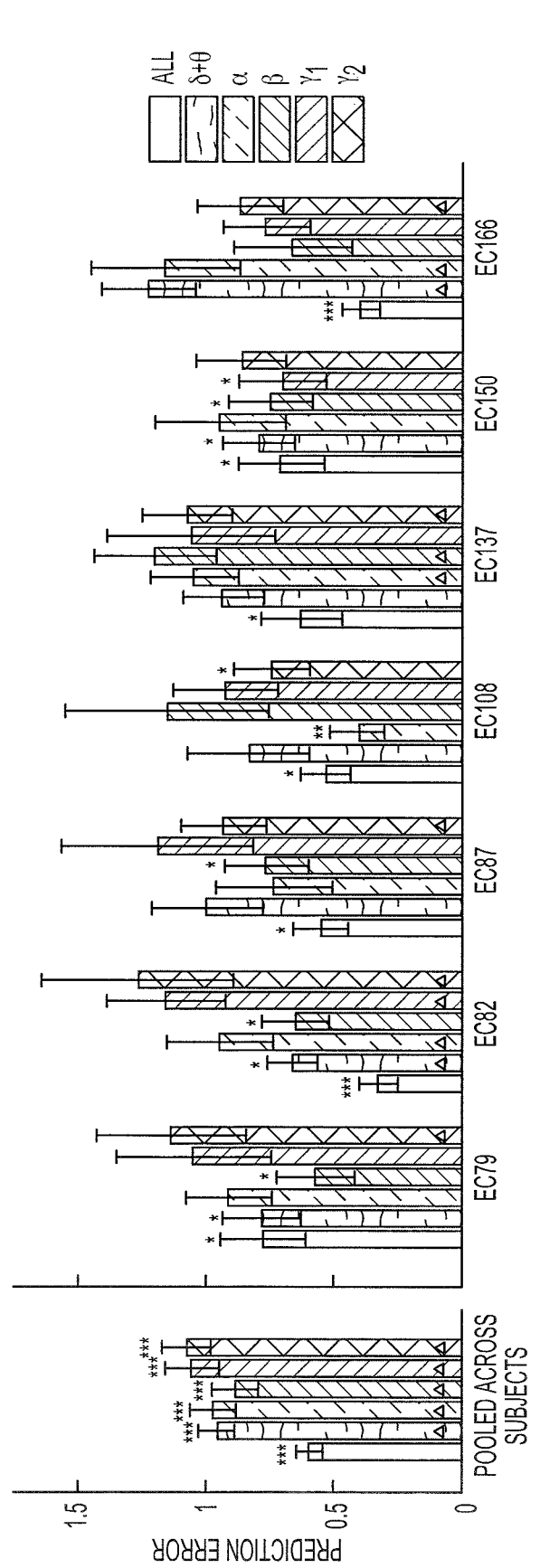
FIG. 18 illustrates decoding performance using only features from one frequency band compared to using features from five frequency bands according to an embodiment of the present disclosure.

FIG. 18 illustrates decoding performance using only features from one frequency band compared to using features from all 5 frequency bands. The cross-validated normalized mean-absolute error (NMAE) is shown for predictions pooled across the population in (a) and for each individual in (b). Within cross-validation, the selected network, the number of PCs, and the neural state dimension for each band were kept the same as those for all bands combined. Bars represent mean and error bars represent s.e.m. (number of samples in (a) is 87 and in (b) is equal to the number of IMS points for each subject provided in FIG. 22). Asterisks indicate significantly predictive decoding using the corresponding band(s) (*, random-test $P<0.05$; , random-test $P<0.005$; *, random-test $P<0.0005$). All frequency bands were predictive in one or more subjects even when used exclusively. Bands with significantly worse decoding error compared with all bands combined (one-sided Wilcoxon signed-rank $P<0.05$) are marked with an upward triangle. No band had significantly lower error than all bands combined. Also, on average, decoding error achieved when the decoder used all bands combined was significantly lower than when it used any single band exclusively as shown in (a). Performing a search of the network, the number of PCs and the neural state dimension for each individual band separately led to similar results.

Figure 19:
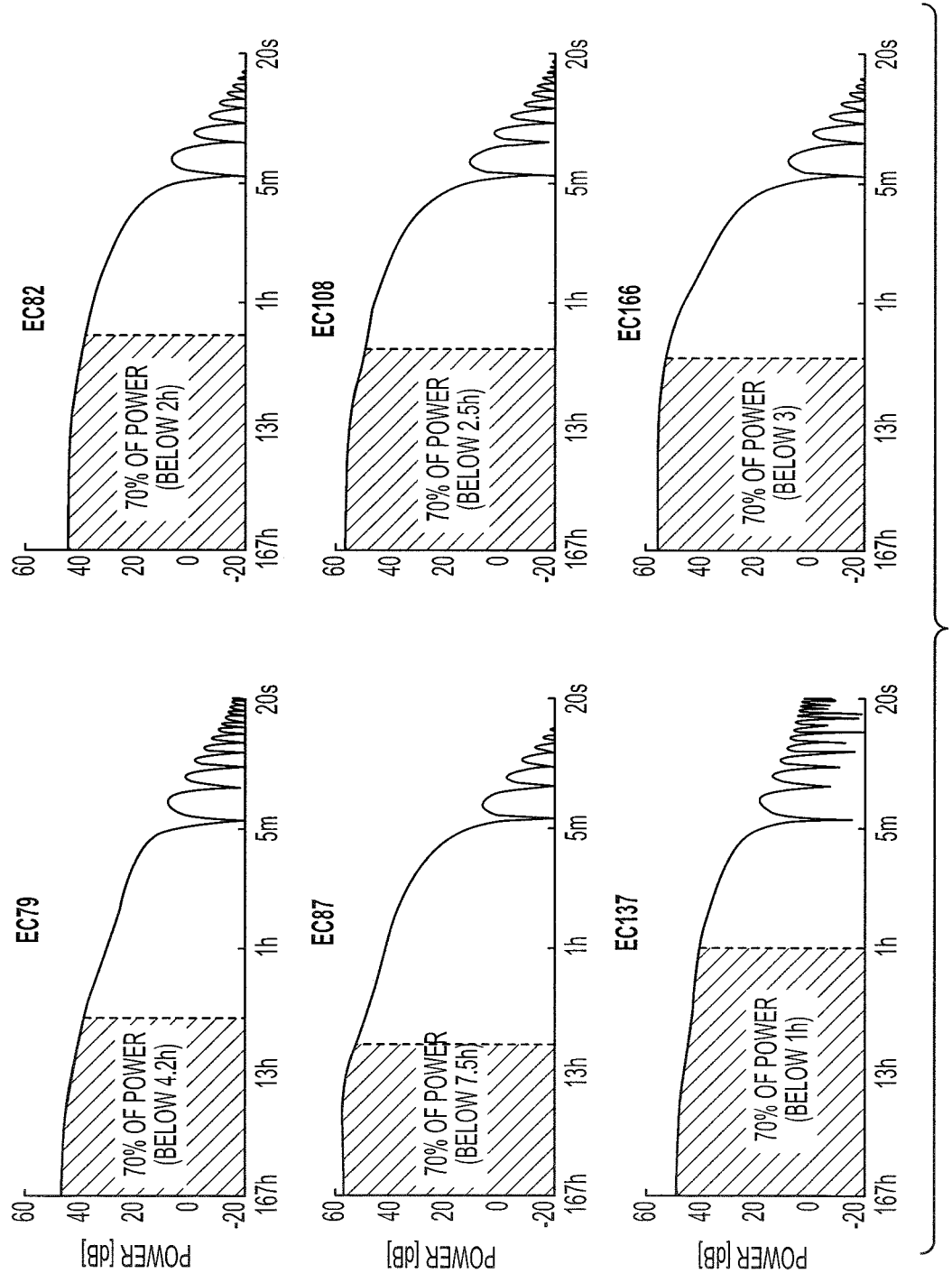
FIG. 19 illustrates analytically estimated power spectral density of decoding mood state in each of multiple subjects of experiments according to an embodiment of the present disclosure.

The LSSM together with the regression model facilitate a direct parametric calculation of the power spectral density (PSD) of the decoded mood time-series. FIG. 19 illustrates multiple plots showing analytically estimated power spectral density (PSD) of the decoded mood state in each subject (a-f). The horizontal axis is the time-scale (inverse of frequency) and the vertical axis is proportional to the log of PSD at the time-scale (dB units). The area under the curve (in original power units) over a certain set of time-scales is proportional to how prominent the decoded mood state variations are at those time-scales. For example, 70% of the variations in the decoded mood state occurred at time-scales of hours or slower. This analysis was not applicable to EC150 as its neural encoding model was the special case of direct regression (i.e., state-space with all eigenvalues of the A matrix equal to 0). Time-scale unit abbreviations: h: hours; m: minutes; s: seconds.

The PSD quantifies the relative prominence of different time-scales (defined as the inverse of frequency), in the decoded mood state variations. For example, it can be computed that more than 70% of the PSD was at time-scales of 3.4 plus or minus 2.3 hours and slower across subjects. It was also confirmed that the decoded mood state changed slowly within minutes of a measured IMS point. Thus, since the neural encoding models are dynamic, they may provide an analytical tool to study the temporal characteristics of the decoded mood state.

The choice of the most appropriate mood state measure for effective closed-loop stimulation is critical to study in future work. Here, IMS was chosen because it could be useful for developing decoders that guide clinical intervention for alleviating depression and anxiety symptoms.

First, interest lies in in tracking momentary variations in mood state because proof-of-concept DBS studies for mood disorders have shown acute mood symptom changes that happen within a short period of minutes. To close the loop in DBS, it is critical for the decoder to track such acute effects of intervention and thus IMS is a useful measure to train the decoders on. In contrast, traditional self-report measures of depression and anxiety symptoms such as PHQ-9 and GAD-7 do not measure such momentary variations because they are designed for diagnosis of depression and anxiety disorders and thus measure the recurrence of symptoms over long time periods relevant for diagnosis, e.g., two weeks. In contrast, IMS measures the current mood state, and thus, by design, is sensitive to momentary variations in mood state as also suggested by the comparison with PHQ-9 and GAD-7 above.

Second, IMS measures an overall mood state related to both depression and anxiety symptoms. Given the high comorbidity of depression and anxiety, an overall mood state measure could be useful in guiding clinical intervention in these disorders.

Third, to guide clinical intervention such as DBS, it is important to measure a full range of mood state effects due to intervention, whether positive or negative. IMS is specifically designed for this purpose by allowing the subject to explicitly indicate both negative and positive mood states. In contrast, in traditional measures of depression and anxiety symptoms (PHQ-9 and GAD-7, respectively), the subject can only indicate the absence of a negative state (e.g., 'depressed'), not the corresponding positive state (e.g., 'happy') explicitly. For example, the extreme score on the positive end of one of PHQ-9 questions represents 'not at all feeling down, depressed and hopeless' (i.e., the absence of a depression symptom not a positive state). IMS has an explicit positive mood state descriptor at the extreme of each question (e.g., 'happy'). So the subject can indicate a positive mood state on the continuum between the negative-positive descriptors. Consequently, high and low IMS scores represent positive and negative mood states, respectively.

Fourth, guiding clinical intervention using a momentary mood state measure (which the IMS provides) could help enable developing mood symptom-relieving therapies for subjects with baseline depression and anxiety disorders in the future As IMS provides a momentary assessment, training decoders on IMS could enable tracking acute momentary mood symptom changes that can happen within a short period of minutes in DBS intervention. Second, given the high comorbidity of depression and anxiety, to guide clinical intervention, it could be useful to decode an overall mood state related to both their symptoms as measured by IMS. Third, IMS allows reporting both negative and positive mood states to indicate both the alleviation of symptoms and the emergence of a positive mood state due to intervention. However, it is emphasized that the modeling framework can be applied to investigate the decoding of other mood measures, as well as other neuropsychiatric states. Mood is a complex construct and many self-reports, including IMS, can be decomposed into multiple components. Also, the IMS depression and anxiety subscales could be decoded using the same modeling framework, thus potentially enabling their future use in closed-loop DBS. The decoders may help facilitate future investigations of effective mood state measures for closed-loop therapies.

Since IMS provides a momentary assessment of anxiety and depression symptoms, a clinical intervention aimed at changing the decoded IMS could be beneficial for symptom control. A critical question is whether such an intervention could also shift the baseline level of mood. Mood often refers to a pervasive and sustained emotional state subject to transient fluctuations in affective state over time. Prior validation indicates that IMS is also significantly correlated with measures of sustained depression and anxiety symptoms.

The results have significant implications for neurotechnologies. The mood state decoders may provide a quantitative measure of mood state from continuous neural recordings. Therefore, the results suggest that future precisely-tailored closed-loop electrical stimulation therapies for depression and anxiety can be possible by using the decoded mood as feedback. Moreover, since the neural encoding models are dynamic and predictive (rather than correlative), they may be extended to predict the effect of stimulation on mood state and other neuropsychiatric states, thus enabling its model-based optimal closed-loop control of mood and other neuropsychiatric states in future.

Similar to mood state, neural processes related to other neuropsychiatric states implicated in disorders such as chronic pain, addiction, or post-traumatic stress disorder are not anatomically localized, but rather span a distributed network of brain regions. Moreover, these neuropsychiatric states are also complex and difficult to track, resulting in sparse behavioral measurements. Given these similar challenges, the modeling framework can generalize to decoding across these neuropsychiatric conditions for future closed-loop treatments.

Taken together, this disclosures provides a first demonstration that mood state variations in individual subjects can be decoded from large-scale intracranial recordings across multiple days, and shows the spatial and spectral aspects of neural activity used in the decoders. These mood state decoders may facilitate the future development of advanced personalized closed-loop therapies for neuropsychiatric disorders such as depression and anxiety.

FIG. 20 illustrates demographic information, intracranial implant duration, seizure foci, and any pathological findings about the resected areas for each subject if applicable.

The above methods were performed on several subjects. In particular, semi-chronic intracranial ECoG electrodes were surgically implanted in seven subjects with treatment-resistant epilepsy for localization of seizure foci.

Raw ECoG signals were continuously recorded during the hospitalization of each subject with a sampling rate of either 0.5 kHz or 1 kHz using Nicolet/XLTex EEG clinical recording systems (available from Natus Medical, Inc. of Pleasanton, CA). ECOG electrodes included 4-contact and 6-contact strip electrodes with 10 millimeter (mm) center-to-center spacing and 2.3 mm exposed diameter, and 4-contact and 10-contact depth electrodes with 6 mm, 5 mm, or 3 mm center-to-center spacing (available from Ad-Tech Corp. of Walnut, CA). Overall, electrode coverage was heterogeneous but some regions (e.g., OFC, ACC, HPC) were covered in most subjects. Anatomical location of contacts on each ECoG electrode, i.e., recording channels, were determined using the FreeSurfer neuroimaging analysis software (an open source software suite) and for electrodes in key limbic regions were validated by expert examination.

Mood states of subjects were measured with a tablet-based self-report mood assessment questionnaire designed by Posit Science Corp. of San Francisco, CA, called the immediate mood scalar (IMS). IMS provides a momentary assessment of a set of mood states related to depression and anxiety symptoms and has been validated against standard self-report measures of these disorders. In each of 24 questions, the subject is asked to rate their current mood state ("rate how you feel now") by tapping one of 7 buttons on a continuum between a pair of negative and positive mood state descriptors with scores of negative 3 and 3, respectively (e.g., "depressed" and "happy"). FIG. 21 is a table illustrating IMS questions.

The buttons on the continuum have scores from negative 3 to 3. The sum of all 24 scores gives the total IMS. A higher IMS corresponds to a more positive mood state. Only IMS points (i.e., reports) that had concurrent usable ECOG recordings were used for the analyses. Any IMS point with change of more than 50 units from a previous IMS point taken within 2 hours prior was removed due to instability (only 1 point). Each subject had 12 plus or minus 2.4 usable IMS points and answering the questions took 2.9 plus or minus 1.4 minutes.

Only 3 subjects (EC79, EC87, and EC150) were using some depression or anxiety medication. There was no systematic synchronization between the timing of IMS points and medication use. IMS points were measured at irregular times but medications were administered in regular 12 or 24-hour intervals. Other medications used by patients were for seizure, pain, and nausea and were administered on an as-needed basis and again had no systematic relation with IMS times.

Subjects were selected to have large-scale recordings along with 1) at least 10 IMS points so that there was enough IMS data for model fitting, and 2) a measured IMS range of at least 10 percent (10%) of the total possible IMS range across multiple days so that there was meaningful mood state variations. Each of the subjects had an IMS range of at least 25% of the total possible IMS range (average of 33%). FIG. 22 is a table illustrating specifications of mood state measurements in each subject.

Raw ECoG signals were first preprocessed offline to remove non-neural activity. For each subject, the ECoG signals were visually examined, and the ECOG channels and time epochs that contained clearly non-neural motion artifacts were marked. Channels that were found to be noisy for more than 10% of the time during the recording or were noisy during the mood state measurements were excluded from analysis. In other channels, neural features were later linearly interpolated during the noisy epochs.

The recordings were downsampled to a 256 Hz sampling rate (after applying a zero-phase antialiasing Chebyshev Type I IIR filter of order 8 with 100 Hz cut-off), high-pass filtered above 1 Hz (order 2 zero-phase IIR Butterworth filter), and then an order 4 zero-phase notch filter was applied at 60 Hz and harmonics to remove the line noise. Common average referencing (CAR) was performed across all channels sharing the same lead. In calculating the reference, channels and time epochs that had been marked as noisy were excluded to prevent noise from spreading to other channels through the CAR.

Log spectral power features were extracted from non-overlapping 10 second (s) windows in 5 frequency bands: 1-8 Hz ($\delta$+$\theta$), 8-12 Hz ($\alpha$), 12-30 Hz ($\beta$), 30-55 Hz ($\gamma_1$) and 65-100 Hz ($\gamma_2$) by filtering the ECOG signal within these bands (order 8 zero-phase IIR Butterworth filter) and then taking the log of the root mean-square of the ECoG signal in each window. The mood state was also decoded from coherence features.

Apart from decoding mood state variations from spectral power features, spectral coherence features were also decoded (which are an example measure of connectivity between channels) to show the robustness of the modeling framework to the choice of neural features. Coherence of pairs of channels were selected within the limbic regions from the same non-overlapping 10 s windows and in the same 5 frequency bands as the power features. The spectral coherence features were computed by using the multi-taper estimation method. It was found that in 6 subjects (all but EC79), coherence-based neural decoders were predictive of mood state. FIG. 23 is a table illustrating a summary of cross-validated prediction error of coherence-based mood state decoders. Note that all models include coherence pairs from all channels in the limbic regions. As shown in the results in FIG. 23, FDR-corrected random-test P-values included: P<0.05 in 4 subjects and P<0.066 in the other 2 subjects. However, coherence-based decoders did not have an advantage in terms of prediction compared with power-based decoders (two-sided t-test P=0.39). The analyses were focused on power features since their smaller feature space made the investigation of spatial network properties more tractable (see below).

The modeling framework for coherence features was identical to that for power features except for a few minor modifications. Since coherence is a quantity with a range of 0 to 1, the non-linear transformation $$f(x) = \ln\frac{x}{1-x}$$

was applied to expand the range of coherence features to real values. For coherence features, to avoid artificial introduction of coherent signals and to minimize the effect of volume conduction on calculating spectral coherences, instead of using CAR, bipolar referencing was used. The regularization parameter $\lambda$ was selected for coherence features just as for power features by minimizing the cross-validated prediction error within the train IMS points; however, if this $\lambda$ did not lead to identification of significantly predictive coherence neural encoding models (only for coherence features in 2 subjects, EC82 and EC108), the regularization was reduced by selecting the smallest value of $\lambda$ that still achieved an error within 1 standard deviation of the minimum cross-validated prediction error within the train IMS points. This extra attempt at fitting the regression models for coherence features was corrected for in false discovery rate (FDR) control.

The coherence feature space even within the limbic regions was very high-dimensional (459 plus or minus 497 features). So due to the large number of cross-regional coherences, they were not considered individually within the progressive region selection procedure. Instead, each region was treated together with all its limbic interactions as a single unit and encoding models were built by combining one or more such units within the progressive region selection procedure. At each stage of progressive region selection, a unit comprising of a single region's coherences with itself (intraregional coherence pairs) and all other regions (interregional coherence pairs) was added to the network. The region selection process was otherwise identical with the case of power features. Hence, in contrast with the power-based encoding models, the identified coherence-based encoding models each included some contribution from all of the limbic regions.

The experiments evaluated decoding within rigorous leave-one-out cross-validation. An IMS point to be predicted was left out as a test IMS. The rest of the IMS points were left as train data (train IMS) to select a network and fit its neural encoding model, and thus to build the decoder. This decoder is then used to predict the test IMS. Critically, the model fitting and selection have no knowledge of the test IMS. This leave-one-out procedure was repeated for all IMS points and the cross-validated IMS prediction NRMSE was computed. Statistical tests were performed on this cross-validated NRMSE (using random-test and permuted-test). The decoders were evaluated for prediction of mood state at the discrete points in time when an IMS point (i.e., report) was available.

Two statistical tests were conducted to assess decoding. The first was the random-test: for each subject, 1000 sets of random integer numbers drawn from the same range as the true IMS points were generated using a uniform distribution and placed at the same times as the true IMS points. Each random set has as many points as there are true IMS points. The exact same cross-validated modeling and decoding was repeated using the same neural data for each set of random IMS points. This results in a distribution of the 1000 random-IMS cross-validated prediction errors for each subject. The random-test P value was defined as the probability that random IMS points will have lower cross-validated prediction error than the true IMS points (see next paragraph). The second test was the permuted-test: the time indices of the IMS points were randomly permuted 1000 times for each subject and the procedure was repeated in the random-test to get the permuted-test P values. The random-test was taken as the main criteria for significance and the permuted-test was provided to show robustness to statistical tests.

FIG. 20 illustrates demographic information, intracranial implant duration, seizure foci, and any pathological findings about the resected areas for each subject if applicable.

FIG. 24 is a table 2400 illustrating specific locations of the implanted intracranial electrodes in each of the subjects. In particular, the table 2400 illustrates intracranial electrode coverage (depth and strip electrodes) in each subject (electrodes that did not have any usable channels due to noise at the time of IMS measurements are not listed). The total quantity of channels lists all the available recording channels regardless of anatomical location. Intracranial electrodes that had at least one recording channel that was verified to be in the limbic regions are listed under 'coverage within the limbic regions' (for these electrodes, only channels that were verified to be in the listed limbic regions are noted under 'number of verified channels' and used in the limbic search analyses). All other electrodes are listed under 'coverage outside the limbic regions'. Note that the quantity of power features is given by the number of channels multiplied by 5 frequency bands.

Subjects were selected to have large-scale recordings along with 1) at least 10 IMS points so that there was enough IMS data for model fitting, and 2) a measured IMS range of at least 10 percent (10%) of the total possible IMS range across multiple days so that there was meaningful mood state variations. Each of the subjects had an IMS range of at least 25% of the total possible IMS range (average of 33%). FIG. 22 is a table illustrating specifications of mood state measurements in each subject.

Mood states of subjects were measured with a tablet-based self-report mood assessment questionnaire designed by Posit Science Corp. of San Francisco, CA, called the immediate mood scalar (IMS). IMS provides a momentary assessment of a set of mood states related to depression and anxiety symptoms and has been validated against standard self-report measures of these disorders. In each of 24 questions, the subject is asked to rate their current mood state ("rate how you feel now") by tapping one of 7 buttons on a continuum between a pair of negative and positive mood state descriptors with scores of negative 3 and 3, respectively (e.g., "depressed" and "happy"). FIG. 21 is a table illustrating IMS questions.

The choice of the most appropriate mood state measure for effective closed-loop stimulation is critical to study in future work. Here, IMS was chosen because it could be useful for developing decoders that guide clinical intervention for alleviating depression and anxiety symptoms. Since mood is not directly observable, the score of a validated tablet-based self-report (IMS) was used (designed by Posit Science Corp.) as the operational definition of mood in this study. While subjective self-reports have intrinsic limitations, they have proven to be useful instruments for measuring mood states. IMS provides a momentary assessment of a set of mood states related to depression and anxiety symptoms. The mood state descriptors used in IMS questions are largely compiled from common depression and anxiety symptoms listed in the literature such as the Diagnostic and Statistical Manual of Mental Disorders (DSM-V) and the IMS score has been validated against standard self-report measures of depression and anxiety. Here, the IMS validations were expanded against these standard self-report measures.

IMS aims to measure momentary mood state variations that are related to depression and anxiety symptoms. IMS has been validated against well-known self-report measures of depression and anxiety symptoms, i.e., PHQ-9 and GAD-7, respectively. PHQ-9 and GAD-7 have been widely used in primary care, and have been shown to achieve high accuracy in diagnosis of depression and anxiety. PHQ-9 and GAD-7 measure the recurrence of symptoms over long time periods relevant for diagnosis (e.g., two weeks) and thus evaluate sustained depression and anxiety symptoms. By collecting IMS and PHQ-9/GAD-7 in the same subject across a large cohort of individuals in a previous study, four main inferences have been made, which together have been used to validate IMS.

First, IMS score has been shown to be significantly correlated with PHQ-9 and GAD-7 scores across a pool of 110/93 subjects who had taken both IMS and PHQ-9/GAD-7 (Pearson's P<0.001 in both cases). FIG. 25A illustrates the range of mood state variations observed in each subject. The lower- and upper-bounds of the boxes represent the 25th and 75th percentiles of the IMS scores, the middle line represents the median and the whiskers represent the minimum and maximum scores for the subject. FIG. 25B illustrates correlation between PHQ-9 and GAD-7 scores with the IMS score (the y-axis is transferred to the equivalent IMS scoring that is used in this study, i.e., scoring each question from negative 3 to 3). This data shows the range of IMS values reported for various values of PHQ-9 and GAD-7 across this large population. The range of IMS observed in this study across the subjects is marked on the plots. The vertical axes in FIGS. 25A and 25B cover the total possible range of IMS (−72 to +72). The horizontal axis in FIG. 25B covers the total range of PHQ-9 (0 to 27) and GAD-7 (0 to 21). This analysis has revealed that the total IMS score is correlated with baseline levels of both depression and anxiety symptoms. Comparing the subjects' IMS scores vs. their PHQ-9/GAD-7 scores suggests that the total range of IMS may cover the entire range of clinical depression/anxiety symptoms measured by PHQ-9/GAD-7.

Second, a factor analysis has shown that the total IMS score has two main factors, an IMS depression subscale (consisting of 7 IMS questions related to depression symptoms) and an IMS anxiety subscale (consisting of 5 IMS questions related to anxiety symptoms). Across the pool of 110/93 subjects, the IMS depression subscale has larger correlation with PHQ-9 than GAD-7, and the IMS anxiety subscale has larger correlation with GAD-7 than PHQ-9. Despite the high rate of comorbidity between depression and anxiety, these results suggest that the two IMS subscales can indeed capture aspects of depression and anxiety symptoms, respectively.

Third, in subjects where IMS and PHQ-9/GAD-7 were administered multiple times, IMS has been shown to have larger variations over time than the variations of PHQ-9/GAD-7. This result suggests that IMS is indeed sensitive to momentary mood state variations.

Fourth, in subjects where multiple IMS, PHQ-9/GAD-7 were administered over a period of several days, using IMS as a time-varying predictor significantly contributed to the prediction of PHQ-9/GAD-7 variations over time.

These results provide validation for IMS and suggest that while IMS is sensitive to momentary variations of mood states, it may also be related to sustained depression and anxiety symptoms over longer time periods.

The methodology could be used to investigate decoding for any measure of mood state (by addressing the challenge of modeling distributed high-dimensional neural features and sparse mood measurements) or other neuropsychiatric state. In the present disclosure, it was chosen to use IMS as the operational definition of mood and thus the decoders were built to predict the total IMS score. The motivations for this choice were rooted in an interest to develop decoders that could help guide clinical intervention for relieving mood symptoms in depression and anxiety disorders in the future.

First, interest lies in in tracking momentary variations in mood state because proof-of-concept deep brain stimulation (DBS) studies for mood disorders have shown acute mood symptom changes that happen within a short period of minutes. To close the loop in DBS, it is critical for the decoder to track such acute effects of intervention and thus IMS is a useful measure to train the decoders on. In contrast, traditional self-report measures of depression and anxiety symptoms such as PHQ-9 and GAD-7 do not measure such momentary variations because they are designed for diagnosis of depression and anxiety disorders and thus measure the recurrence of symptoms over long time periods relevant for diagnosis, e.g., two weeks. In contrast, IMS measures the current mood state, and thus, by design, is sensitive to momentary variations in mood state as also suggested by the comparison with PHQ-9 and GAD-7 above.

Second, IMS measures an overall mood state related to both depression and anxiety symptoms. Given the high comorbidity of depression and anxiety, an overall mood state measure could be useful in guiding clinical intervention in these disorders.

Third, to guide clinical intervention such as DBS, it is important to measure a full range of mood state effects due to intervention, whether positive or negative. IMS is specifically designed for this purpose by allowing the subject to explicitly indicate both negative and positive mood states. In contrast, in traditional measures of depression and anxiety symptoms (PHQ-9 and GAD-7, respectively), the subject can only indicate the absence of a negative state (e.g., 'depressed'), not the corresponding positive state (e.g., 'happy') explicitly. For example, the extreme score on the positive end of one of PHQ-9 questions represents 'not at all feeling down, depressed and hopeless' (i.e., the absence of a depression symptom not a positive state). IMS has an explicit positive mood state descriptor at the extreme of each question (e.g., 'happy'). So the subject can indicate a positive mood state on the continuum between the negative-positive descriptors. Consequently, high and low IMS scores represent positive and negative mood states, respectively.

Fourth, guiding clinical intervention using a momentary mood state measure (which the IMS provides) could help enable developing mood symptom-relieving therapies for subjects with baseline depression and anxiety disorders in the future.

The methodology described herein aims to build a mood state decoder for each subject that can generalize to predicting new IMS points from neural features. The high-dimensionality of neural features (due to the distributed representation of mood) and the sparsity of available IMS points for training (due to the difficulty of mood assessment over time) pose a challenging modeling problem. A direct fitting of a decoder using all neural features would result in overfitting to the IMS points used for training and thus would not generalize to decoding a new IMS. To build a generalizable decoder, a methodology consisting of multiple elements was developed to be specifically designed to avoid overfitting. The key idea was to construct the neural encoding model such that the number of model parameters that need to be fitted using the IMS points was smaller than the number of available IMS points. Multiple analyses validate the modeling framework in building generalizable decoders, which are summarized below.

The main results that allow for significant prediction of the test IMS, rule out overfitting to train IMS points because evaluation of IMS prediction occurs within cross-validation. In cross-validation, an IMS point is left out (test IMS), and the rest of the IMS points (train IMS) are used to fit the decoder. This fitted decoder is then tested on the test IMS. So if the model overfits to the train IMS, the cross-validated prediction error will significantly degrade and the decoder will fail to predict the test IMS.

More specifically, to get a chance level of cross-validated prediction error, the exact same cross-validated modeling and evaluation procedure are applied to IMS points that are either permuted in time or randomly drawn from the same range. The main results show that the probability that an arbitrary random/permuted set of IMS points can be decoded as accurately as the true set of IMS points is extremely small (random-test $P=3.8\times10^{-12}$ and permuted-test $P=1.1\times10^{-15}$).

Since cross-validation was performed, the test IMS to be decoded is in no way used to train the decoder. Thus the decoder cannot be informed of the test IMS (e.g., overfit to the test IMS). Nevertheless, multiple analyses in the results further confirm the validity of the cross-validation procedure based on data, thus confirming that decoding generalizes to new IMS points without overfitting.

First, the exact same modeling/decoding framework cannot decode random/permuted IMS points. If the decoding was due to any part of modeling being informed of the test IMS (e.g., due to error in cross-validation), then there should have been no difference between decoding of random/permuted vs. true IMS points. However, it is shown that the prediction error of the true IMS points was substantially lower than that of random/permuted IMS points using the exact same neural activity and modeling framework (two-sided t-test $P<10^{-207}$). Further, the probability that the cross-validated prediction error of any arbitrary set of random/permuted IMS points would be as low as that achieved for the true IMS points is extremely small overall as noted above. These results rule out the possibility that the decoder is informed by the test IMS (e.g., due to error in cross-validation).

Figure 26:
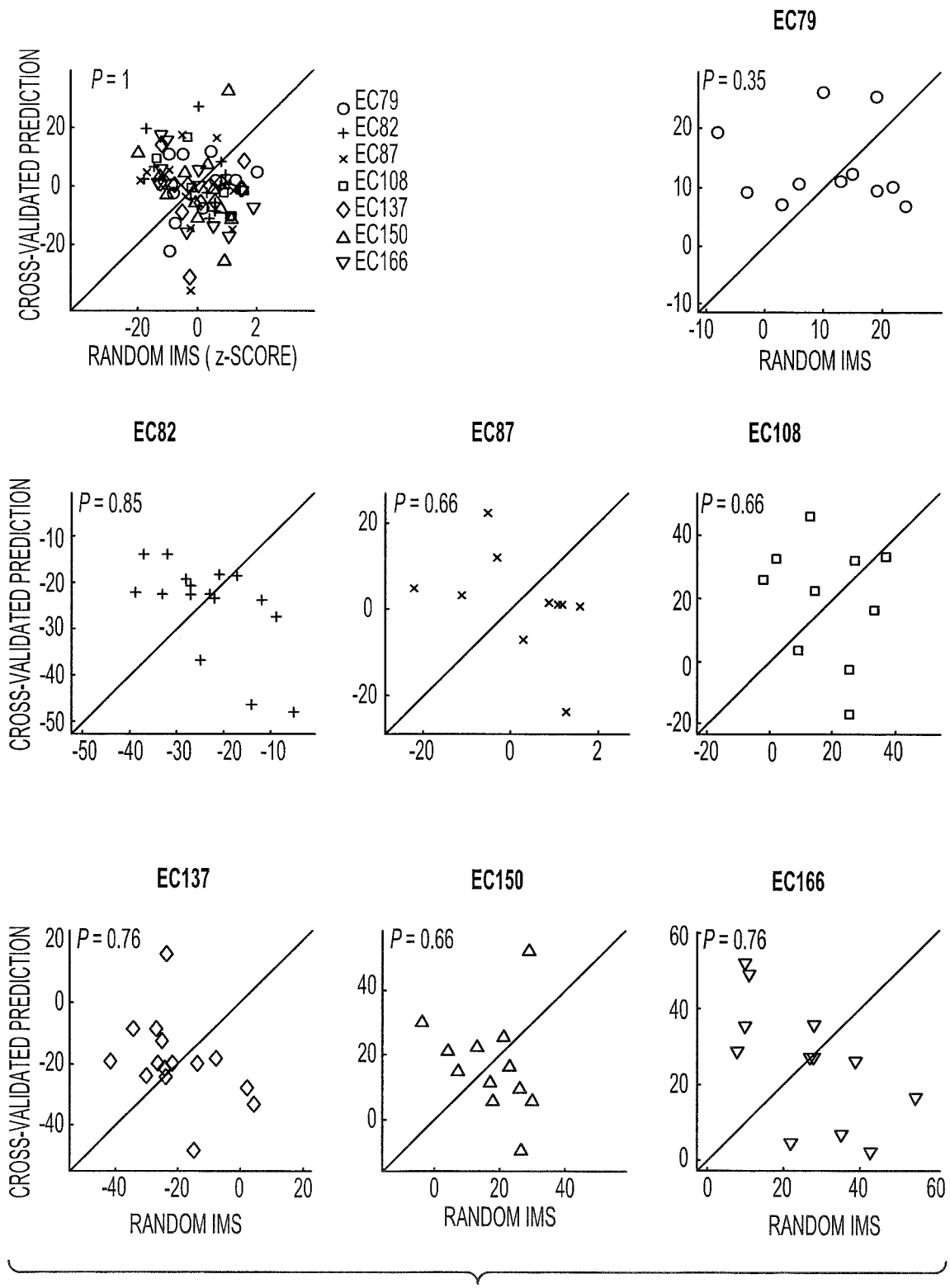
FIG. 26 illustrates cross validated predictions for an example set of random IMS points according to an embodiment of the present disclosure.

FIG. 26 illustrates cross-validated predictions for an example (randomly selected) set of random IMS points is shown pooled across subjects in (a) and within individuals in (b-h).

If the models overfitted to train IMS, there should have been no difference between random/permuted and true IMS predictions and the experiments should not have been able to obtain significant prediction results. Taken together, the main results rule out overfitting to train IMS.

Figure 27:
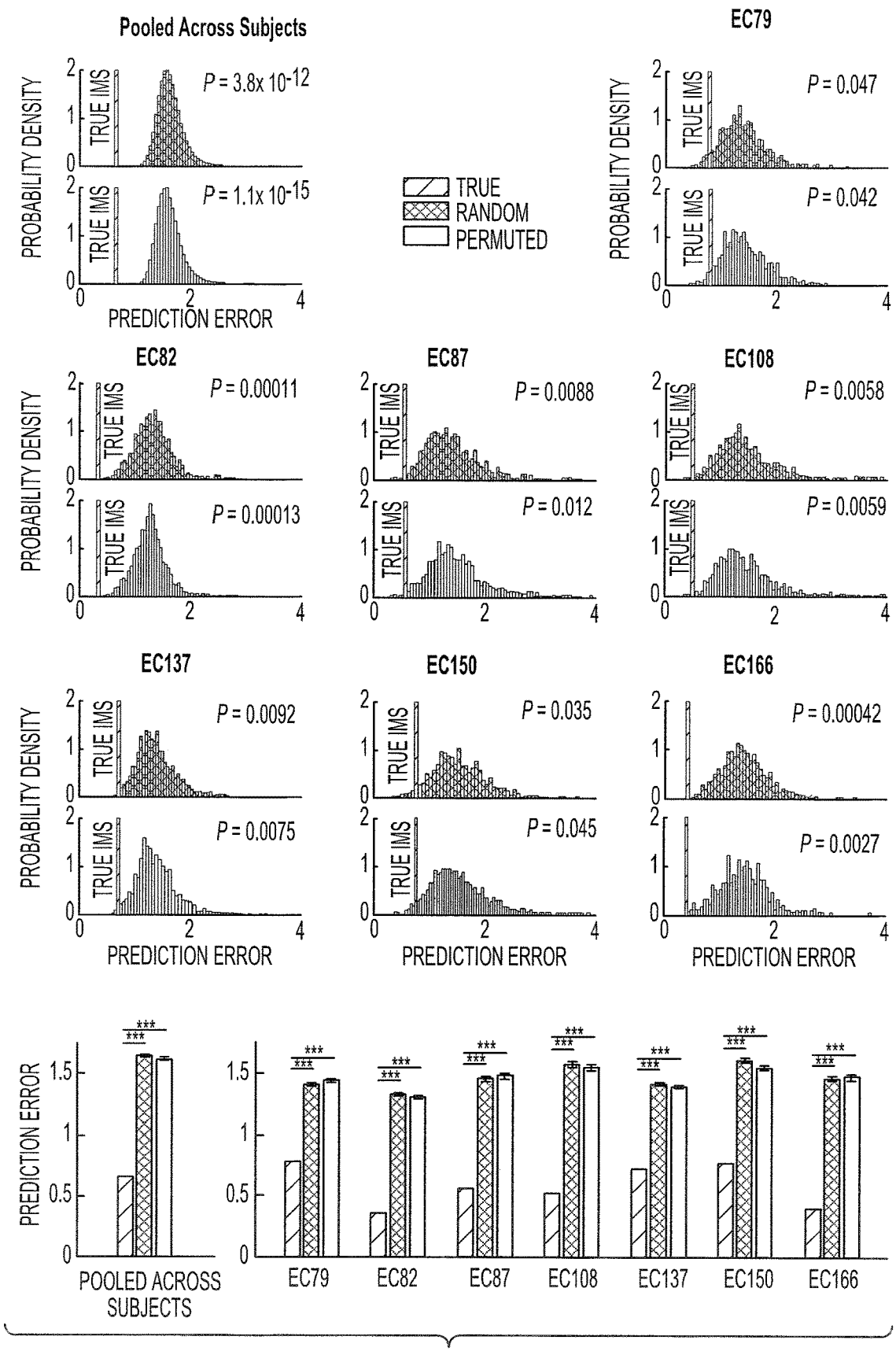
FIG. 27 illustrates cross-validated prediction error for random and permuted sets of IMS points compared with a true set of IMS points according to an embodiment of the present disclosure.

This result is further confirmed by the distribution of cross-validated error for random/permuted IMS points and by the cross-validated predictions of an example random set of IMS points. FIG. 27 illustrates cross-validated prediction error for random and permuted sets of IMS points, compared with the true set of IMS points. Cross-validated prediction error is quantified by the normalized root mean-squared error (NRMSE). Distribution of the prediction error for sets of random and permuted IMS points pooled across subjects (a) and within individuals (b-h) are shown. Cross-validated prediction error for the true IMS points is shown as a vertical line in each plot. The random/permuted test P value is computed as the probability that NRMSE for random/permuted sets of IMS will be equal to or smaller than that of the true IMS points (area under the distribution tail to the left of the vertical line). (i, j) show bar plots for average cross-validated prediction errors pooled across subjects (i) and in individual subjects (j). In all cases, a two-sided t-test comparing true IMS NRMSE with random/permuted IMS average NRMSE resulted in $P<10^{-207}$, which is indicated by ***. Error bars represent s.e.m. Quantity of samples is equal to the number of random/permuted sets, i.e. to $10^9$ in (a, i) and 1000 in (b-h, j).

Second, the exact same modeling/decoding framework cannot decode the true IMS points when using electrodes outside limbic regions. In 6 subjects, the number of neural features outside the limbic regions was similar to those inside the limbic regions. If the decoding was due to any part of modeling being informed of the test IMS (e.g., due to error in cross-validation), then there should have been no difference between decoding with electrodes inside vs. outside limbic regions. However, it was found that decoding with electrodes outside the limbic regions largely fails, it is significant only in 2 of the 6 subjects, and is insignificant across the population.

In contrast, decoding with electrodes inside limbic regions was significant in 5 of these 6 subjects and was significant across the population. As a side note, decoding in the only subject (EC137) that required electrodes outside the limbic regions, still required including the limbic regions as well (without limbic regions decoding failed). In this subject, limbic regions in addition to one electrode covering some cortical regions that are also known to be mood-relevant (middle and superior frontal gyri (dorsolateral and dorsomedial prefrontal cortex)) were selected for decoding. Also, in the two subjects that decoding without limbic regions was significant (EC108 and EC166), the best small mood-predictive network for decoding consisted of the inferior temporal cortex, which has also been implicated as mood-relevant in prior studies.

Third, when searching among all electrodes and without knowing where these electrodes are, the modeling framework consistently selects the same limbic regions for decoding as the ones selected in the limbic search. If the decoding was due to any part of modeling being informed of the test IMS, then there should have been no difference between the choice of regions; the modeling should have been able to overfit with any brain regions as long sufficient neural features were used there. The consistent selection of limbic regions regardless of the search space, and the biological consistency of this selection with prior neuroimaging studies—that have shown the central role of limbic regions in emotion and mood processing—show the validity of the cross-validation procedure and rule out overfitting.

Finally, consecutive IMS points were measured on average 13 hours apart. Nevertheless, two new analyses further rule out the possibility that leave-one-out cross-validation may contribute to prediction because of correlations in time. First, if this was the case, test IMS points that were closer to a train IMS point should have had better decoding accuracy. However, it was found that the cross-validated prediction error was not correlated with the time-distance between the test IMS and the closest train IMS (Spearman's $P=0.99$ across the population (across in total 87 IMS points) and $P>0.15$ in every subject. Second, if this was the case, there should have been no difference in decoding with electrodes inside vs. outside the limbic regions because the same leave-one-out cross-validation method was used to decode in both cases. However, as indicated above, it was found that decoding significantly deteriorates and largely fails (fails both at the population level as well as in 4 of 6 individual subjects) when using electrodes outside limbic regions.

To ensure that IMS prediction was not due to epilepsy specific neural activity, a control analysis was performed, which resulted in a finding that interictal discharge rates in the selected networks used for decoding were not significantly predictive of mood state in any subject. In each subject, the interictal epileptic discharge rates of the exact same mood-predictive networks that were used in the decoders were estimated. Epileptic interictal discharges were detected by comparing the raw ECoG signal magnitude with a threshold and finding the time points at which the signal magnitude goes beyond the threshold. As the threshold, 3.5, 4, and 4.5 times the signal standard deviation were each tested. In each of the channels included in the mood-predictive networks, the discharge incidents were counted in a 4-minute window around each IMS point, which was the same window used for neural state averaging and prediction in the original decoder. Then, a linear regression model (as in our original decoder) was built to predict the IMS points from these discharge counts. To evaluate the prediction, leave-one-out cross-validation was performed, and random and permuted tests were used as described above ($P>0.18$ for random-test and permuted-test in all subjects).

To calculate random/permuted P values for individual subjects, a Gamma distribution was fitted to the empirical baseline distribution using maximum likelihood estimation, and its goodness-of-fit was tested by using the Anderson-Darling test. If $P>0.05$ in the Anderson-Darling test, the fitted Gamma distribution was used to calculate the random/permuted-test P values as the probability of the NRMSE for random/permuted IMS being less than the NRMSE achieved for the true IMS. If the Anderson-Darling test rejects the null hypothesis (i.e., the Anderson-Darling test P<0.05), it indicates that the Gamma distribution is not a good fit. In this case, the random/permuted test P values were calculated by using a parametric generalized Pareto distribution (GPD). The distribution of the extreme values of any set of independent and identically distributed random variables can be approximated by a GPD. The smallest 250 samples were selected from the random/permuted distributions and a GPD was fitted using these samples with the maximum likelihood method. It was next confirmed that the fitted GPD passed the Anderson-Darling test (it passed in all relevant subjects) and then the random/permuted test P-values were obtained from the cumulative density function of the fitted GPD.

In random/permuted test, at stage h of progressive region selection, the complete cross-validated model fitting and selection was repeated for each set of random/permuted IMS points (each of 1000 sets) while fixing the network size to be equal to h. This procedure provides the distribution for the null hypothesis that a network with a size of h is not predictive of IMS. Hence, when a network size of 1 (using only a single region) is not sufficient for decoding and the process proceeds to the second stage, a new null hypothesis with the network size of 2 is considered. Since this would be the second attempt at forming and testing a hypothesis, FDR control is applied to correct for multiple comparisons if it is necessary to search beyond a single region (only was necessary in 2 of the 7 subjects).

To further validate the FDR correction, an alternative statistical test was devised that incorporates the effect of multiple comparisons into the hypothesis and the null distribution and thus does not require FDR correction. In this alternative test, at stage h in progressive region selection, the network size is no longer fixed to be h; instead, each random/permuted set was allowed to try all network sizes up to h (i.e., 1, 2, . . . , h) and as soon as any of these network sizes enables significant prediction for that set, the method stops, just as is the case for true IMS points. This test provides the distribution for the null hypothesis that a network with a size up to h is not predictive of IMS. Note that for a network size of 1, this test is equivalent to the original test. For larger network sizes, this second test takes the effect of the multiple comparisons in the progressive region selection into account by allowing each random/permuted set to perform the same multiple comparison procedure as the true IMS points, thus removing the need for FDR correction. As expected, the P values computed with this test were close to the FDR corrected P values computed from the original test, and did not affect the results.

The neural encoding model expressed in Equations 2-4 is a dynamic model and provides multiple benefits, which are expanded upon below.

The LSSM in Equation 3 is a dynamic model as it characterizes how neural features evolve in time in terms of a hidden neural state. The same neural state that describes the neural feature dynamics is regressed to IMS points (Equation 4). Thus the neural encoding model is also dynamic as it relates the time-variations in IMS points to temporal dynamics of neural features through this shared neural state. The dynamic LSSM explicitly models how neural states (and thus neural activity and mood state) evolve in time through the state transition matrix A, and characterizes the effect of noise on neural states through K (Equation 3). In decoding, this gives rise to Kalman filtering (discussed below with respect to Equation 6), which enables optimal suppression of noise and accumulation of information over time in estimating the neural state (since the neural state $x_t$ depends on its past values) and thus in decoding mood state. Thus dynamic modeling is beneficial in extracting information from noisy neural features. Another benefit of dynamic modeling is that it allows for studying of the time-scales of the decoded mood.

Motor BMIs use various neural signal modalities including intracortical spikes and local field potentials (LFP), and ECOG in both online and offline studies. State-space models have also been useful in some motor BMIs, though in that context the state is largely taken as the kinematic state (with random-walk evolution) rather than a hidden neural state. In computational neuroscience, state-space models with a low-dimensional hidden neural state to model and decode localized spiking activity have been used in a few studies. Here, the finding for the first time that mood state can be decoded from the low-dimensional hidden neural states estimated from large-scale ECoG signals demonstrates the utility of a linear state-space model in characterizing large-scale distributed ECoG processes.

The regularization parameter $\lambda$ was selected by using an inner-level of cross-validation. Values from $10^{-4}$ to $10^5$ (in 100 logarithmically spaced steps) were searched for and, for each, an inner cross-validation was performed within the training dataset and the cross-validated prediction error of the regression model was computed. Then, the value that minimized the prediction error in this inner cross-validation within the training dataset was selected.

The total number of parameters in the regression model is $n_x+1$ ($n_x$ parameters for T and 1 for $s_0$). When fitted using ridge regularization with parameter $\lambda$, the effective number of regression parameters is shown below in Equation 9.

$$f(\lambda) = \sum_{i=1}^{n_x+1} \frac{d_i^2}{d_i^2 + \lambda} \qquad \text{Equation 9}$$

In Equation 9, where $d_i$'s are the singular values of the data matrix $$1\begin{bmatrix} 1 & \cdots & 1 & \cdots & 1 \\ \bar{x}^{(1)} & \cdots & \bar{x}^{(k)} & \cdots & \bar{x}^{(M)} \end{bmatrix} \in \mathbb{R}^{(n_x+1) \times M} \text{ with } \bar{x}^{(k)}$$

being the averaged neural state around the k'th train IMS, and M being the number of train IMS points. From the above equation, it is easy to see that $f(\lambda) < \min(n_x+1, M)$ for any $\lambda > 0$. This is a well-known result. Briefly, this is because the maximum number of non-zero singular values in the above data matrix cannot be larger than the number of its rows ($n_x+1$) or columns (M). Thus there are at most $\min(n_x+1, M)$ non-zero terms, each smaller than 1, in the above summation. Consequently, regularization ensures that the effective number of regression parameters $f(\lambda)$ is strictly less than the number of regression parameters and less than the number of available IMS points (see FIG. 29). Note that ridge regularization alone is not sufficient for solving the challenge of IMS sparsity. The dimensionality reduction steps before the ridge regression (i.e., progressive region selection, PCA, and LSSM), which restrict the number of regression parameters ($n_x+1$), are crucial in enabling fitting of a non-trivial regression model. Without those dimensionality reduction steps, the number of regression parameters (equal to the number of neural predictors) will be much larger than the number of IMS points. Thus, a very large $\lambda$ resulting in a trivial regression model with $T \cong 0$ may be the optimal solution to ridge regression in this case, which will result in decoding to fail in cross-validation.

Progressive region selection finds the smallest network size that is sufficient for decoding by selecting among available anatomical regions. Within a given small network, all neural features are modeled at all frequency bands, without selecting the specific frequency bands to include in the model. There are several reasons for the above choices.

First, neural circuits underlying mood representation involve multiple distributed cortico-limbic regions, and prior neuroimaging studies have shown that anatomical cortico-limbic regions have differential roles and varying relevance to mood representation, e.g., limbic regions including OFC, anterior cingulate cortex, amygdala, and hippocampus have been shown to play critical roles in mood representation. Hence, selectively including them in the models can help reduce dimensionality by eliminating less relevant regions or avoiding redundancy caused from using all regions.

In contrast, there is no similar conclusive evidence about a systematic difference among various frequency bands of electrophysiological neural signals in terms of mood representation. Prior studies largely use neuroimaging signal modalities such as the Blood Oxygenation Level Dependent (BOLD) signal in functional magnetic resonance imaging (fMRI) and do not study the roles of neural activity frequency bands in mood representation. Also, prior electrophysiological studies that use the electroencephalogram (EEG) or local field potential (LFP) to classify depression subjects and healthy individuals have not provided converging evidence for a systematic difference in various frequency bands in terms of mood representation. Consistent with these studies, the neural feature tuning results discussed herein show that powers of various frequency bands were tuned to mood state variations, with both positive and negative correlations.

Given the lack of evidence on differential roles of frequency bands, no selection was made among frequency bands because doing so would have unnecessarily increased the number of possible candidate models and made it more difficult to select a generalizable model within cross-validation.

Figure 28:
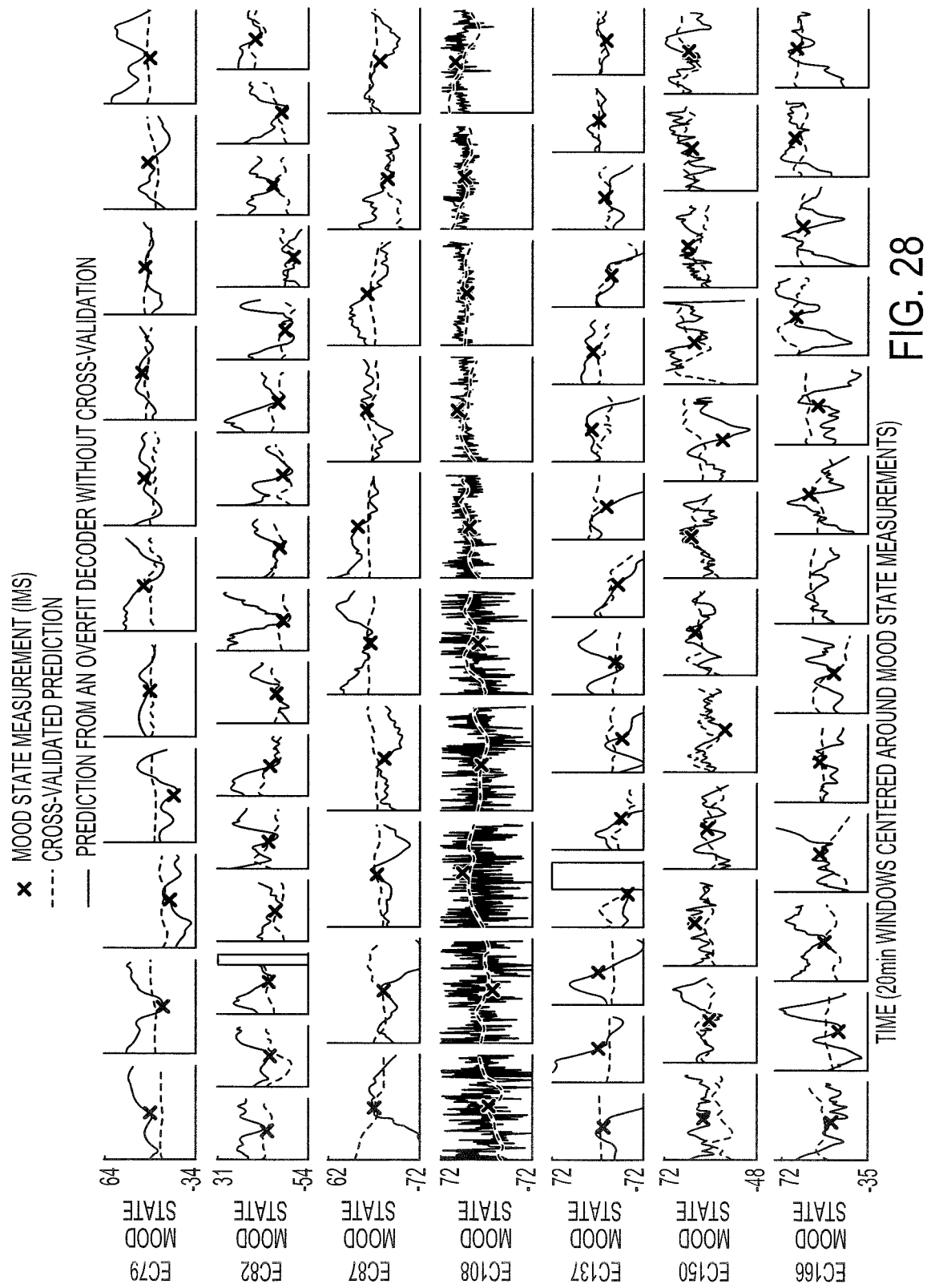
FIG. 28 illustrates that mood state decoders provided a slowly changing prediction of mood state around measured IMS points according to an embodiment of the present disclosure.

FIG. 28 illustrates that mood state decoders provided a slowly-changing prediction of mood state around the measured IMS points. Cross-validated prediction of mood state over time in a 20-minute window centered around each measured IMS point is shown. The true value of the measured IMS point is marked with a cross. The decoder used to obtain the trace in each subplot for prediction around each IMS point is trained only using the other IMS points in the subject (i.e., cross-validation). For 2 IMS points, decoding is shown for less than 10 minutes after the IMS point since the subject was going to sleep immediately after the completion of the IMS report rendering the neural features unreliable. For comparison, traces of an overfit decoder trained with a degenerate version of our method and without cross-validation is also shown. This overfit decoder was constructed by deliberately removing several components in the modeling framework, which are designed to prevent overfitting (i.e., progressive region selection, regularization in regression, and the sensitivity measure and inner-level cross-validation for model selection). Moreover, the leave-one-out cross-validation was fully removed, and the overfit decoder was trained on all IMS points. So to obtain the trace, the IMS point in each subfigure is used in the training of the overfit decoder. In contrast to the decoder formed using the methods herein, the overfit decoder results in mood traces that often have large variations even within minutes. The standard deviation of the overfit trace during a 20-minute window around each IMS point was significantly larger than the standard deviation of the cross-validated decoded trace across all subjects (one-sided Wilcoxon signed-rank $P=8.5\times 10^{-15}$).

To train generalizable decoders with sparse mood state measurements, one key idea was to restrict the number of parameters that need to be fitted using the IMS points to be smaller than the number of available IMS points. In particular, FIG. 29 is a table 2900 that illustrates details of the fitted neural encoding model corresponding to the best small mood-predictive network for decoding in each subject. The table provides key variable dimensions in the process of dimensionality reduction. Dimensionality reduction reduced the quantity of regression parameters to be between 30% and 50% of the quantity of available IMS points, as shown in the last two columns.

FIG. 30A is a table providing details of the best small mood-predictive networks for decoding in each subject.

FIG. 30B is a table providing abbreviations used for anatomical regions. As shown in FIGS. 30A and 30B, networks selected when searching (1) only inside limbic regions, (2) among all regions, (3) only outside limbic regions are provided. When significant decoding was not possible within a search for a given subject, no network is given. Compared with the limbic search, the expanded search among all regions resulted in exactly the same network in all applicable subjects (EC82, EC108, EC150 and EC166) except EC87 in whom a larger network with the same limbic regions in addition to some other mood-relevant regions were selected. This limbic vs. all-region comparison was not applicable for 2 subjects, as for EC137 all regions had already been searched in the main analysis, and in EC79 searching all regions did not result in a robust neural encoding model likely because of the large search space.

Adaptive Tracking of Human ECoG Methods

Identification and tracking of brain network dynamics is important both for understanding neural mechanisms and for developing various neurotechnologies. For example, such tracking is essential in uncovering biomarkers for neurological disorders such as depression, for decoding neuropsychiatric state, or for developing adaptive closed-loop stimulation therapies or brain-machine interfaces (BMIs) to treat various neurological and neuropsychiatric disorders.

However, brain network dynamics may be non-stationary and time-variant in some cases, especially over long periods of days or weeks. Indeed, various neurotechnologies, such as closed-loop brain stimulation systems, need to operate over these long periods. Hence the prediction power of a time-invariant SSM estimated with an offline batch of data can degrade over time. Developing adaptive models that can track non-stationarities may improve the prediction of brain network dynamics relative to time-invariant models, and in turn improve neural biomarker discovery, neuropsychiatric state such as mood decoding, and model-based closed-loop electrical stimulation systems.

Adaptive methods have significantly improved the performance of spike-based closed-loop motor BMIs and electroencephalogram (EEG)-based closed-loop systems for anesthetic delivery. In addition to spikes and EEG, ECoG provides a new recording modality that has a higher signal-to-noise ratio compared to EEG and could improve longevity compared to spikes. As such, ECoG holds great promise as the feedback signal to estimate the brain state. It is therefore important to examine the nonstationary nature of human ECoG network activity and to develop adaptive SSM identification algorithms to track its non-stationary dynamics online.

An adaptive subspace identification algorithm may be used to estimate time-variant SSMs online. A forgetting factor is applied and time-variant output covariances computed to deal with non-stationarity over time. Recursive QR-decomposition enables online implementation of the algorithm. The non-stationary nature of high-density ECoG data (around 105 channels) from three epilepsy patients was recorded by comparing the prediction of the time-variant SSM with a time-invariant SSM estimated with traditional non-adaptive subspace identification algorithms such as N4SID. Spontaneous ECOG signals were continuously recorded over on average 5 days, for example. The adaptive identification algorithm resulted in time-variant models that predicted the ECOG network dynamics better than the non-adaptive models in all three subjects. Results confirmed that non-stationary dynamics exist in high-dimensional human ECoG signals, and that the proposed adaptive identification algorithm can successfully track the non-stationary dynamics and improve the ECOG prediction power.

Under the assumption that brain network dynamics are stationary, the present inventors propose time-invariant linear SSMs to predict ECOG dynamics. To model spontaneous human ECoG dynamics, the time-invariant linear SSM may be written as shown in Equation 10 below:

$$\begin{cases} x_{t+1} = Ax_t + w_t \\ y_t = Cx_t + v_t \end{cases} \quad \text{Equation 10}$$

In Equation 10, $y_t \in R^{n_y}$ is the observed neural features, which is selected as ECOG log-powers, $x_t \in R^{n_x}$ is a hidden state and $w_t$ and $v_t$ summarize modeling errors and unmeasured disturbances/inputs, and are modeled as white Gaussian noises with zero mean and $$\mathbb{E}\left[\begin{pmatrix} w_i \\ v_j \end{pmatrix} (w_j' v_j')\right] = \begin{pmatrix} Q & S \\ S' & P \end{pmatrix} \delta_{ij} \text{ with } \delta_{ij} = 1 \text{ if } i = j$$

covariance and 0 otherwise. Here, ·' represents the transpose of a vector or a matrix. Subspace identification algorithms can be used, such as N4SID, to identify the time-invariant model parameters, including the model order $n_x$, system matrices $A \in R^{n_x \times n_x}$, $C \in R^{n_y \times n_x}$, and noise covariance matrices $Q \in R^{n_x \times n_x}$, $P \in R^{n_y \times n_y}$, and $S \in R^{n_x \times n_y}$.

The dynamics of long-term human ECoG recordings could be non-stationary, violating the assumption for the time invariant model. The goal is to develop an adaptive SSM identification framework to track the non-stationary dynamics. A time-variant linear SSM was built as shown in Equation 11 below:

$$\begin{cases} x_{t+1} = A_t x_t + w_t \\ y_t = C_t x_t + v_t \end{cases} \quad \text{Equation 11}$$

In Equation 11, the system matrices $A_t$, $C_t$, and noise covariances matrices $Q_t$, $R_t$, and $S_t$ are modeled to be time-variant. Tracking non-stationary dynamics is then equivalent to tracking these time-variant model parameters. To estimate these online, an adaptive identification algorithm was developed. For compactness of exposition, the details of the algorithm are omitted and some key components are introduced.

The core of traditional subspace algorithms such as N4SID consists of two steps. The first step is to compute the time-invariant output covariance matrices $$\Lambda_\tau = \mathbb{E}[y_{t+\tau} y_t'] \propto \sum_{k=1}^T y_{k+\tau} y_k',$$

with T denoting the total time of recordings. The second step is to estimate A, C, Q, P, and S from those output covariance matrices via subspace estimation techniques such as singular-value decomposition. To implement the algorithms in a robust and efficient way, QR-decomposition of a particular matrix formed by the outputs has been used. From the upper triangular matrix R in this QR-decomposition, A, C, Q, P, and S can be efficiently calculated.

Here, a modified subspace learning algorithm is developed to estimate time-variant SSMs online. The key idea is that, in contrast with traditional subspace algorithms, the time-variant output covariance matrices are estimated as shown in Equation 12 below.

$$\Lambda_\tau(t) = \mathbb{E}[y_{t+\tau} y_t'] \propto \sum_{k=1}^T \beta^{t-k} y_{k+\tau} y_k' \quad \text{Equation 12}$$

In Equation 12, t is the current time and $\beta \in (0,1)$ is a user-defined constant forgetting factor. Thus, the estimate of output covariance matrices is updated at every time step, where more weight is placed on the recent data than past data.

Since new output covariance matrices are calculated at every time step, the QR-decomposition also needs to be recalculated at every time step. To enable online operation of the QR-decomposition, a recursive algorithm is used to update the R matrix in the QR-decompositions. Based on Equation 12, after straightforward algebraic manipulations, the R matrix of the current time step, i.e., $R_t$, can be calculated as shown in Equation 13 below.

$$R_t = \sqrt{\beta G_1 R_{t-1}} + G_2 \tilde{y}_t \quad \text{Equation 13:}$$

In Equation 13, $R_{t-1}$ is the R matrix of the previous time step, $\tilde{y}_t = [y_{t-d+2}', y_{t-d+1}', \ldots, y_t']$ is the current data vector, with d a user-defined delay factor, and $G_1$, $G_2$ are Givens rotation matrices calculated from $R_{t-1}$ and $\tilde{y}_t$. As the last step, $A_t$, $C_t$, $Q_t$, $P_t$, and $S_t$ are extracted from $R_t$ following the procedures of standard subspace algorithms.

Together, these steps provide an adaptive identification algorithm to track ECoG non-stationarity over time.

Figure 31:
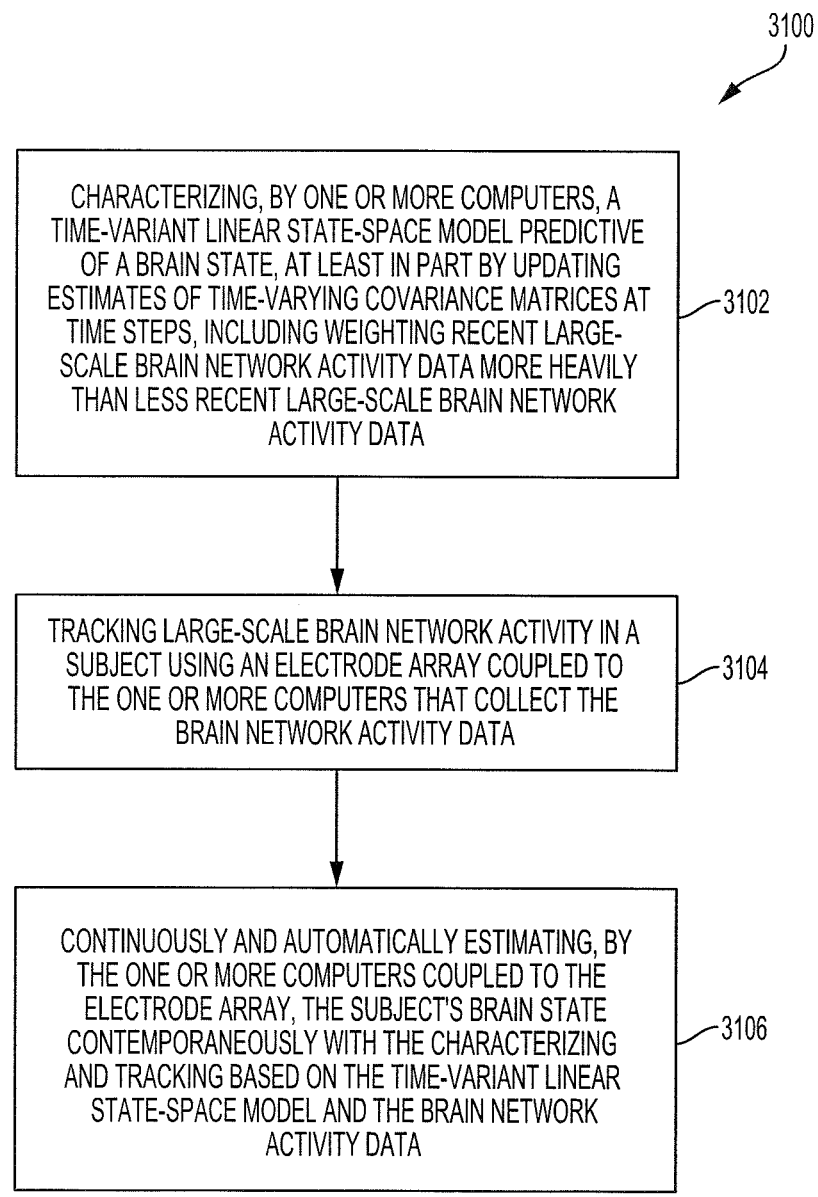
FIG. 31 illustrates a method for adaptive tracking of large-scale brain network activity and estimating a brain state based on brain network activity data according to an embodiment of the present disclosure.

FIG. 31 is a flowchart illustrating a method 3100 for adaptive tracking of large-scale multisite or single-site brain network activity. The method 3100 may be performed, for example, by a computer system having one or more processor and a non-transitory memory.

The method 3100 may include, at 3102, characterizing a time-variant linear state-space model predictive of a brain state. The characterizing 3102 may include using one or more computers or processors receiving signals from an electrode network. The characterizing may be performed at least in part by updating estimates of time-varying covariance matrices at time steps, including weighting recent large-scale brain network activity data more heavily than less recent large-scale brain network activity data. In some embodiments, characterizing the time-variant linear state-space model may include recalculating QR-decomposition at every time step, or at selected intervals of time steps.

The method 3100 may further include, at 3104, tracking large-scale brain network activity in a subject using an electrode array coupled to the one or more computers that collect the brain network activity data. The network may be multisite or single-site. The brain network activity data may include neurophysiological signal data for a subject collected over a period long enough to include detectable time-variance in correlation the subject's brain state to the brain network activity. The neurophysiological data may include at least one of electroencephalogram (EEG) data, ECoG data, local field potential data, or spike firing rates data, which may be collected by any suitable method, such as by implanted or external electrodes. The method 3100 may include collecting the neurophysiological signal data using electrodes covering large-scale brain regions, at multiple sites ("multisite") or at a single site ("single-site").

The method 3100 may further include, at 3106, continuously and automatically estimating, by the one or more computers or processors coupled to the electrode array, the brain state of the subject such as mood or neuropsychiatric state. In some embodiments, this may be performed contemporaneously with the characterizing and tracking based on the time-variant linear state-space model and the brain network activity data.

Some embodiments of the characterizing 3102 may include deriving at least one signal feature from ECoG or equivalent data. The deriving may include one or more processes, including removing noise by common average referencing, dividing the neurophysiological signal data into time delimited windows, and estimating a power spectral density of each window. Deriving the at least one signal feature may further include at least one of calculating a power characteristic of multiple frequency bands thereby obtaining a high-dimensional power characteristic time series, or calculating coherence of the neurophysiological signal data across multiple pairs of electrodes. The at least one signal feature may include one or more of the following: phase, power, log power or other function of power, coherence or a function of coherence, phase-amplitude coupling, or the like. Any suitable signal feature may be used for characterizing the time-variant linear state-space model.

Figure 32:
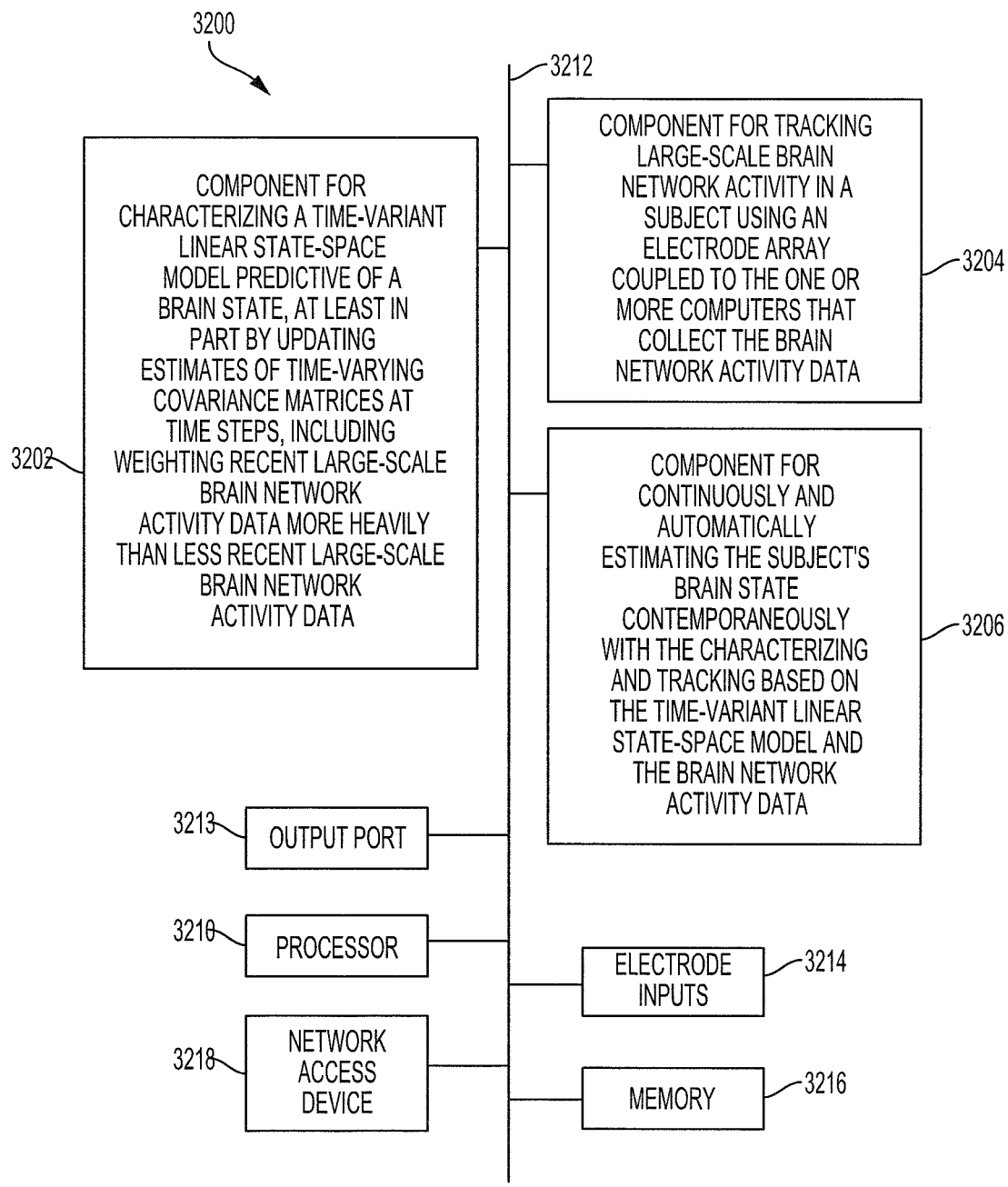
FIG. 32 illustrates a system for adaptive tracking of large-scale brain network activity and estimating a brain state based on brain network activity data according to an embodiment of the present disclosure.

FIG. 32 is a block diagram illustrating components of an apparatus or system 3200 for adaptive tracking of large-scale brain network activity. The network may be multisite or single-site. The apparatus or system 3200 may include additional or more detailed components for performing functions or process operations as described herein. As depicted, the apparatus or system 3200 may include functional blocks that can represent functions implemented by a processor, software, or combination thereof (e.g., firmware). For example, the functional blocks may be implemented by one or more processor 3210.

As illustrated in FIG. 32, the apparatus or system 3200 may comprise an electrical component 3202 for characterizing a time-variant linear state-space model predictive of a brain state, at least in part by updating estimates of time-varying covariance matrices at time steps, including weighting recent large-scale brain network activity data more heavily than less recent large-scale brain network activity data. The component 3202 may be, or may include, a means for said characterizing. Said means may include the processor 3210 coupled to the memory 3216, and to an output port or device 3213, the processor executing an algorithm based on program instructions stored in the memory 3216. Such algorithm may include a sequence of more detailed operations, for example, as described above.

The apparatus 3200 may further include an electrical component 3204 for tracking large-scale brain network activity in a subject using an electrode array coupled to the one or more computers or processors that collect the brain network activity data. The component 3203 may be, or may include, a means for said tracking. Said means may include the processor 3210 coupled to the memory 3216, the processor executing an algorithm based on program instructions stored in the memory. Such algorithm may include a sequence of more detailed operations, for example, receiving an analog signal from one or more electrodes 3214, correlating the input signal to a time index, and converting the signal to an encoded sequence of derived signal features.

The apparatus 3200 may further include an electrical component 3206 for continuously and automatically estimating, by the one or more computers or processors coupled to the electrode array, the brain state of the subject such as mood or another neuropsychiatric state, which may be performed contemporaneously with the characterizing and tracking based on the time-variant linear state-space model and the brain network activity data. The component 3205 may be, or may include, a means for said estimating. Said means may include the processor 3210 coupled to the memory 3216, the processor executing an algorithm based on program instructions stored in the memory 3216. Such algorithm may include a sequence of more detailed operations, for example, accessing an updated characteristic model from the component 3202, applying the updated model to an encoded sequence from the tracking component 3204, and generating an estimate of brain state based on the updated model and latest tacking data.

The apparatus 3200 may optionally include the processor 3210 which may include any discrete logic, processor, controller, or the like. The processor 3210 may be in operative communication with the components 3202-3206 via a bus 3212 or similar communication coupling. In the alternative, one or more of the modules may be instantiated in the processor 3210. The processor 3210 may effect initiation and scheduling of the processes or functions performed by the electrical components 3202-3206.

The apparatus may further include an electrode array 3214 designed to sense neurophysiological signals collected from large-scale brain regions or from a single site network, coupled to the processor, or a port for receiving signals from said array. In some embodiments, the apparatus 3200 may include a network access device 3218 operable for communicating with system components over a computer network. The network access device may communicate via any wired or wireless protocol and may be, or may include, for example, an Ethernet port or serial port (e.g., a Universal Serial Bus (USB) port), a Wi-Fi port, a Bluetooth port, or the like.

In some embodiments, the apparatus 3200 may include a component for storing information, such as, for example, a non-transitory memory 3216. The memory 3216 may be operatively coupled to the other components of the apparatus 3200 via the bus 3212 or the like. The memory 3216 may be designed to store computer readable instructions and data for effecting the processes and behavior of the components 3202-3206, and subcomponents thereof, or the processor 3210, or the method 3100 and one or more of the additional operations disclosed herein. The memory 3216 may retain instructions for executing functions associated with the components 3202-3206. While shown as being external to the memory 3216, it is to be understood that the components 3202-3206 can exist within the memory 3216 or an on-chip memory of the processor 3210. In some embodiments, the processor 3210 may include networked microprocessors from devices operating over a computer network.

In addition, the apparatus or system 3200 may include any suitable output device 3213 for outputting data, such as estimates from the components 3202-3206. For example, the output device 3213 may include a display, a touchscreen, a speaker, or the like. The apparatus or system 3200 may also include inputs ports for one or more user interface devices, for example, a keyboard, touchscreen, microphone, or pointing device, or may include such user interface devices.

Adaptive Tracking of Human ECoG Data

Experiments were carried out using high-density ECoG data from three human epilepsy patients (S1-S3) for on average 5 days (S1: 126 hours; S2: 111 hours; S3: 123 hours). On average 105 ECoG electrodes were used on each patient (S1: 128, S2: 114; S3: 75) covering various brain regions at a sampling rate of 1 kilohertz (kHz).

Figure 33A:
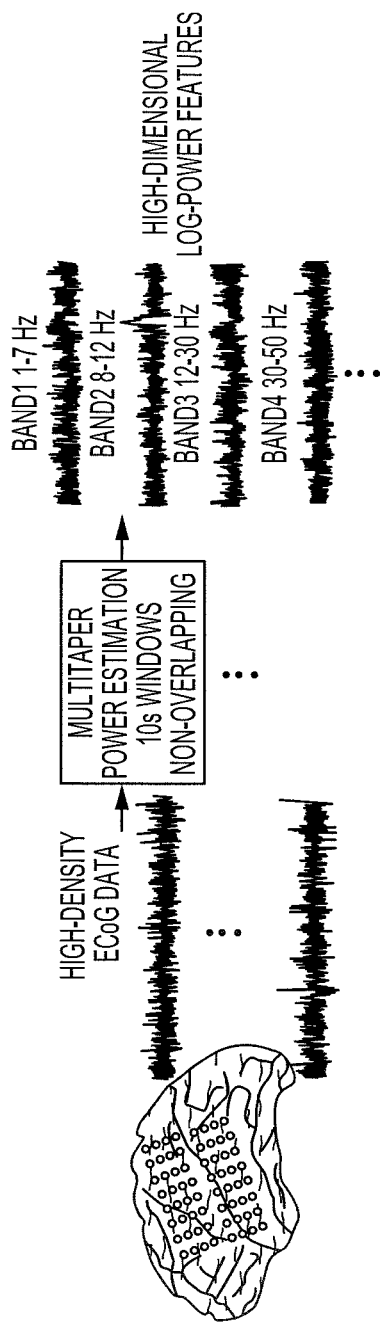
FIGS. 33A and 33B illustrate a data processing procedure according to an embodiment of the present disclosure.

FIG. 33A is an illustration of a calculation of ECoG log-power features. Log-power features were used as the neural observations $y_t$, as shown in FIG. 33A. To obtain the log-power features, common average referencing was first used to remove common noises. Next, 10 second rectangular windows were used to divide the ECoG across time. For each window, a multi-taper method was used to estimate the power spectral density (PSD) of the windowed ECOG. The log-powers of four frequency bands were then calculated, [1 7]Hz, [8 12]Hz, [13 30]Hz, and [31 50]Hz. Consequently, a high-dimensional log-power time series was obtained, with an average dimension of 420 across subjects. To have a consistent number of total features across subjects, 300 features were randomly selected as $y_t$ (since S3 has the minimum total number of features, which is 300). Therefore, for each subject, $y_t$ has a dimension of $n_y=300$. Finally, for each component of $y_t$, the mean was removed from the time-series to have zero mean outputs.

Figure 33B:
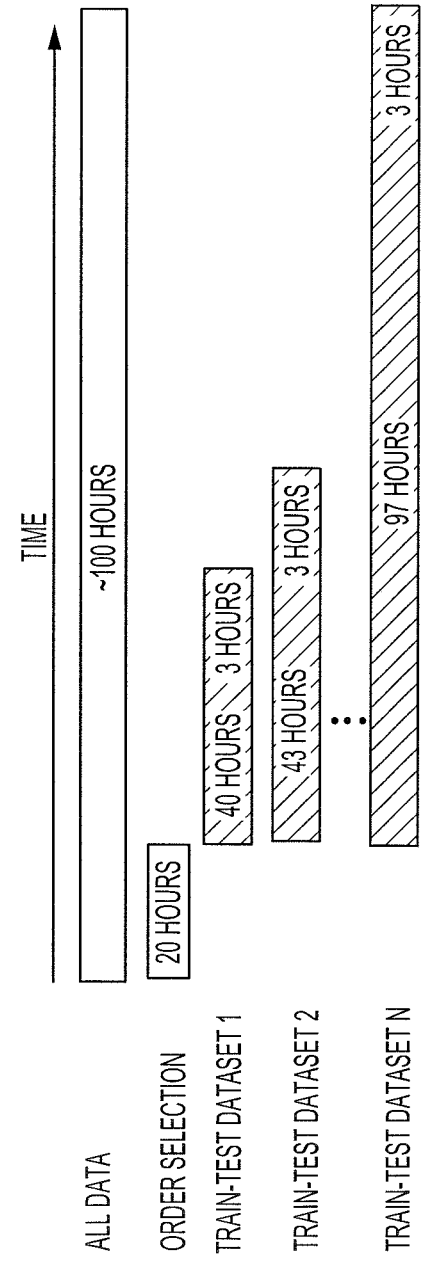

FIG. 33B illustrates a procedure of state-space model training and testing. For each subject, $y_t$ was divided into training and testing datasets as shown in FIG. 33B. Using the same training dataset, two SSMs were estimated by the adaptive and non-adaptive identification algorithms, referred to as $SSM_{adpt}$ and $SSM_{non-adpt}$, respectively. For the adaptive identification algorithm, the SSM was adaptively estimated until the end of the training dataset and then was fixed as $SSM_{adpt}$. For the nonadaptive identification algorithm, a single model was trained, $SSM_{non-adpt}$, using the entire batch of training data. The prediction power of $SSM_{adpt}$ and $SSM_{non-adpt}$ were compared on a subsequent testing dataset. Note that $SSM_{adpt}$ was not further adapted in the testing dataset. This means that both $SSM_{adpt}$ and $SSM_{non-adpt}$ are trained using the exact same data. By comparing the prediction power of the two models, it is shown that ECOG dynamics could be non-stationary and that the $SSM_{adpt}$ can better track ECoG dynamics in the testing dataset compared with $SSM_{non-adpt}$.

To make a comprehensive comparison between $SSM_{adpt}$ and $SSM_{non-adpt}$, 1) the same model order n, was used for both models and 2) the models were compared on multiple testing datasets. To estimate $n_x$, data from the first 20 hours was used to estimate $n_x$ by non-adaptive subspace algorithms and Akaike information criterion (AIC). Then, $n_x$ was fixed for both the adaptive and non-adaptive identification algorithm for subsequent SSM training.

To compare $SSM_{adpt}$ and $SSM_{non-adpt}$ on multiple testing datasets, "train-test" datasets were formed as described below. This started with a 40-hour training and 3-hour testing "traintest" dataset. $SSM_{adpt}$ and $SSM_{non-adpt}$ were trained on the 40-hour training dataset using algorithms introduced above. Here, β was set to be equal to 0:9999, and d was set to be equal to 10 in the adaptive identification algorithm for all subjects. Then, the prediction power of $SSM_{adpt}$ and $SSM_{non-adpt}$ was computed on the 3-hour testing dataset. After this first "train-test" dataset, the training dataset was successively enlarged to form multiple "train-test" datasets. The last "train-test" dataset will cover all the data until the end of the ECOG log-power time series. For each "train-test" dataset, the model identification and performance assessment procedure was repeated. Finally, for every subject, the prediction power of $SSM_{adpt}$ and $SSM_{non-adpt}$ was compared on multiple testing sets (number of testing sets Ntest=22; 17; 21 for the 3 subjects).

To compare the prediction power of $SSM_{adpt}$ and $SSM_{non-adpt}$ quantitatively, one-step-ahead prediction error was calculated on testing datasets. For a given SSM with estimated parameters $\hat{A}$, $\hat{C}\sim$, $\hat{Q}$, $\hat{P}$ and $\hat{S}$, the one-step-ahead prediction of $y_{t+1}$ provides an estimate of the neural features at time t+1 given their observations up to time t. This prediction is given by the following Kalman predictor as shown below in Equation 14:

$$\begin{cases} \hat{x}_{t+1|t} = \hat{A}\hat{x}_{t|t-1} + \hat{K}(y_t - \hat{C}\hat{x}_{t|t-1}) \\ \hat{y}_{t+1|t} = \hat{C}\hat{x}_{t+1|t} \end{cases} \quad \text{Equation 14}$$

In Equation 14, $\hat{K}=(\hat{A}X\hat{C}'+\hat{S})(\hat{C}X\hat{C}'+\hat{P})^{-1}$, and matrix X obtained from the Ricatti equation $X=\hat{A}X\hat{A}'+\hat{Q}-(\hat{A}X\hat{C}'+\hat{S})(\hat{C}X\hat{C}'+\hat{P})^{-1}(\hat{C}X\hat{A}'+\hat{S}')$. Initialization was performed such that $\hat{X}_{1|0}=0$. The relative prediction error (RPE) was defined as shown below in Equation 15.

$$RPE = \frac{1}{n_y}\sum_{i=1}^{n_y} \sqrt{\frac{\sum_{t|t=1}^{T_{test}} (\hat{y}_{t|t-1}^{(i)} - y_t^{(i)})^2}{\sum_{t=1}^{T} (y_t^{(i)})^2}} \quad \text{Equation 15}$$

In Equation 15, $T_{test}$ is the total number of time samples in a test dataset. $RPE_{adpt}$ and $RPE_{non-adpt}$ were defined as the RPE of $SSM_{adpt}$ and $SSM_{non-adpt}$. For a particular SSM, the model was defined to have significant prediction power if its RPE across testing datasets are significantly less than 1 (p<0:05 in a Wilcoxon signed-rank test). This is because mean prediction, i.e., predicting the feature value simply as its mean (0 in the present case), corresponds to RPE=1 and provides no real prediction power.

Next, to better demonstrate the results, a baseline RPE was introduced using prediction errors on training datasets. $RPE_{baseline}$ was defined as the minimum one of the RPEs of $SSM_{adpt}$ and $SSM_{non-adpt}$ on the training dataset. It is clear that $RPE_{baseline}$ is a lower bound of $RPE_{adpt}$ and $RPE_{non-adpt}$, since the latter are prediction errors on the testing dataset whereas the former is over the training dataset. Next, a normalized RPE was defined (NRPE) as RPE on a testing dataset normalized to $RPE_{baseline}$, as shown below in Equation 16.

$$NRPE = \frac{RPE - RPE_{baseline}}{RPE_{baseline}} \quad \text{Equation 16}$$

Finally, the improvement from $NRPE_{non-adpt}$ was summarized to $NRPE_{adpt}$ across testing datasets using the following error reduction percentage (ERP) shown in Equation 17 below.

$$ERP = \frac{\mathbb{E}[NRPE_{non-adpt}] - \mathbb{E}[NRPE_{adpt}]}{\mathbb{E}[NRPE_{non-adpt}]} \times 100\% \quad \text{Equation 17}$$

Next, results will be shown from an example subject (S2), as well as results from all subjects.

Consistent with prior work of the inventors, it was confirmed that both $SSM_{adpt}$ and $SSM_{non-adpt}$ could predict the high-dimensional ECOG features. For S2, compared with mean prediction, both models had significant prediction power using an AIC-selected model order $n_x$ of 28. That is, $RPE_{adpt}$ and $RPE_{non-adpt}$ were significantly below 1 across 17 testing datasets, as shown in FIGS. 34A and 34B (p<0:0005). In particular, FIG. 34A illustrates prediction errors on testing datasets, and FIG. 34B illustrates normalized relative prediction errors. In FIG. 34B, bars represent mean and whiskers represent standard error of the mean, with * corresponding to p<0.05,  corresponding to p<0.005, and * corresponding to p<0.0005. Note that all statistical tests discussed with respect to the above data are performed using the Wilcoxon signed-rank test. The same results held across all 3 subjects (p<0:0005).

Second, by examining some example predictions of $SSM_{non-adpt}$, it was found that ECoG data could exhibit nonstationary dynamics. For example, in S2, it was seen that the trained $SSM_{non-adpt}$ can have large bias in predicting the true power features in the testing dataset, as shown in FIG. 34C. In particular, FIG. 34C illustrates examples of prediction of output log-power features. It was hypothesized that this bias came from data non-stationarity since the training datasets spanned a relatively long time-period (at least 40 hours). Hence, the dynamics at the end of the training dataset could be different from the dynamics at the beginning of the training dataset. In this case, the average time-invariant model $SSM_{non-adpt}$ cannot adapt to the time variations and thus has large prediction errors on the testing datasets ($RPE_{adpt}$>1 in these two particular features). To confirm this hypothesis, next, the predictions of the time-variant model $SSM_{adpt}$ were examined, which showed that $SSM_{adpt}$ can largely reduce the bias, as shown in FIG. 34C. This shows that nonstationarities indeed exist in human ECoG data.

Figure 35:
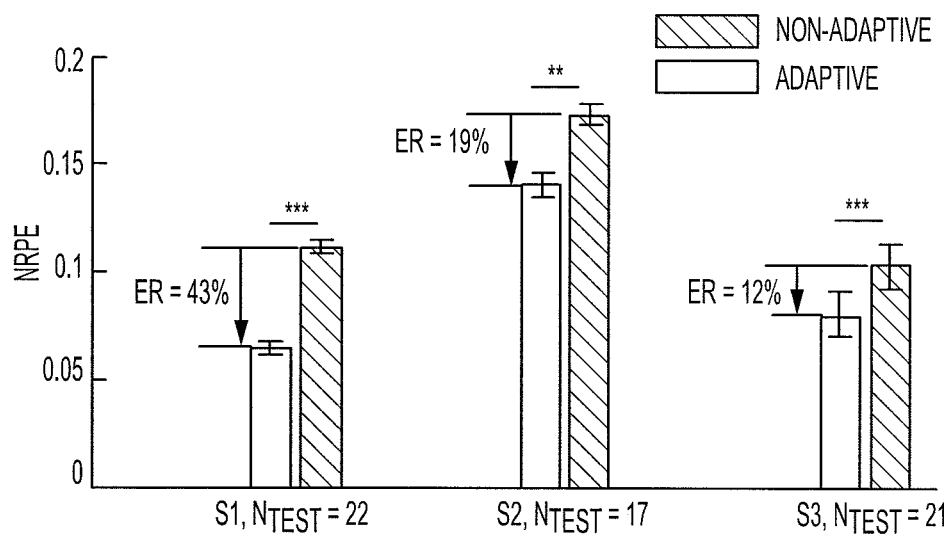
FIG. 35 illustrates performance of adaptive and non-adaptive state-space model (SSM) across three subjects according to an embodiment of the present disclosure.

Third, by comparing the prediction powers of $SSM_{adpt}$ and $SSM_{non-adpt}$, it was found that the proposed adaptive algorithm can successfully account for the nonstationarity. For example, in S2, (N)$RPE_{adpt}$ was significantly less than (N)$RPE_{non-adpt}$ across 16 testing datasets (as shown in FIGS. 34A and 34B, p<0:005). This indicates that the time-variant model $SSM_{adpt}$ better captured the non-stationary dynamics than the time-invariant model $SSM_{non-adpt}$. The above results were consistent across subjects. For each subject, $SSM_{adpt}$ had significantly smaller NRPEs compared with $SSM_{non-adpt}$ across testing datasets, as shown in FIG. 35. In particular, FIG. 35 illustrates performance of $SSM_{adpt}$ and $SSM_{non-adpt}$ (p<0:005). Across subjects, the error reduction percentage from $NRPE_{non-adpt}$ to $NRPE_{adpt}$ was on average 25 percent (25%, as shown in FIG. 35). These results further confirm that non-stationary dynamics exist in human ECoG data. The results also demonstrate that the proposed adaptive algorithm can successfully estimate time-variant SSMs to track non-stationary dynamics, and can improve the prediction performance of time-invariant SSMs.

A method for adaptive tracking of large-scale brain network activity may include characterizing, by one or more computers, a time-variant linear state-space model predictive of a brain state such as mood or other neuropsychiatric state, at least in part by updating estimates of time-varying covariance matrices at time steps, including weighting recent large-scale brain network activity data more heavily than less recent large-scale brain network activity data. The adaptive tracking of large-scale brain network activity may include tracking large-scale brain network activity in a subject using an electrode array coupled to the one or more computers that collect the brain network activity data. The adaptive tracking of large-scale brain network activity may include continuously and automatically estimating, by the one or more computers coupled to the electrode array, the subject's brain state such as mood or neuropsychiatric state contemporaneously with the characterizing and tracking based on the time-variant linear state-space model and the brain network activity data.

In some embodiments, the brain network activity data may include neurophysiological signal data for a subject collected over a period long enough to include detectable time-variance in correlation the subject's brain state to the brain network activity. The neurophysiological data may comprise at least one of electroencephalogram (EEG) data, electrocorticogram (ECoG) data, local field potential data, or spike firing rates data. In some embodiments, the brain network activity data may be a collection of neurophysiological signal data using electrodes covering large-scale brain regions.

In some embodiments, the brain network activity data may include a derivation of at least one signal feature from the ECOG data. The derivation may include removing noise by common average referencing according to various embodiments. In other embodiments, the derivation may include dividing the neurophysiological signal data into time delimited windows. The brain network activity data may be an estimation of a power spectral density of each window. The at least one signal feature may be selected from a group consisting of: phase, power, log power or other function of power, coherence or a function of coherence, phase-amplitude coupling, or any combination of the foregoing.

According to some embodiments, the derivation may include at least one of calculating a power characteristic of multiple frequency bands thereby obtaining a high-dimensional power characteristic time series, or calculating coherence of the neurophysiological signal data across multiple pairs of electrodes.

A method for adaptive tracking of large-scale brain network activity may include characterizing the time-variant linear state-space model comprises recalculating QR-decomposition at every time step.

In some embodiments, the electrode array may be a multisite array comprising multiple electrodes. In other embodiments, the electrode array may be a single-site array.

An apparatus for adaptive tracking of large-scale brain network activity may include one or more processors coupled to a memory, the memory holding program instructions that when executed by the one or more processors causes the apparatus to perform the previously disclosed method.

In some embodiments, the apparatus may include an electrode array configured for sensing neurophysiological signals collected from large-scale brain regions, coupled to the processor. In other embodiments, the apparatus may include means for sensing neurophysiological signals collected from large-scale brain regions.

The present disclosure describes an adaptive subspace identification algorithm to estimate time-variant state-space models that track non-stationary brain network dynamics. This adaptive subspace identification algorithm is applied to high-dimensional human ECoG data. It is shown that, compared to traditional non-adaptive identification algorithms, the proposed adaptive identification algorithm could better predict high-dimensional ECoG log-power time series in three human subjects. These results demonstrate that 1) human ECoG dynamics could be non-stationary over long time-periods, and that 2) the presented adaptive SSM identification algorithm can track data non-stationarities and time-variations.

Tracking non-stationary neural dynamics is essential for developing closed-loop stimulation systems that achieve better treatment of various neurological disorders. Adaptive model identification can lead to more precise estimation of neural biomarkers, and can facilitate the design of more effective feedback-controlled stimulation strategies. In addition, stimulation therapy might induce plasticity and changes in network dynamics. Stimulation induced plasticity is a special case of non-stationarity, and hence the adaptive algorithm has the potential to also track and account for plasticity effects. The results shown and discussed herein thus have important implications for more accurate estimation of neural biomarkers and for better closed-loop stimulation therapies for a wide range of neurological disorders.

Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A method for decoding mood or other neuropsychiatric states from large-scale brain activity signals, comprising:
    receiving, by one or more computers, the large-scale brain activity signals from an electrode assembly coupled to a subject;
    receiving, by the one or more computers, independently derived measures of a mood state or a neuropsychiatric state;
    identifying, by the one or more computers, a predictive network from the large-scale brain activity signals based on the independently derived measures of the mood state or the neuropsychiatric state, wherein the predictive network comprises brain activity signals predictive of one of the mood state or the neuropsychiatric state; and
    responsive to the predictive network including at least one predictive brain activity signal, the one or more computers is configured to perform the steps of:
        modeling a brain activity model from the at least one predictive brain activity signal;
        decoding, through the brain activity model, the mood state or the neuropsychiatric state of the subject from the at least one predictive brain activity signal; and
        providing a signal indicative of the decoded mood state or the decoded neuropsychiatric state, based on the decoding.

2. The method of claim 1, further comprising extracting neural signal features from the large-scale brain activity signals prior to the identifying the predictive network, wherein the predictive network is identified at least partially from the extracted neural signal features, the modeling the brain activity model is at least partially based on the extracted neural signal features from the predictive network, and the decoding the at least one of the mood state or the neuropsychiatric state includes decoding at least partially based on the extracted neural signal features from the predictive network.

3. The method of claim 2, wherein the extracting neural signal features from the large-scale brain activity signals is by measuring a coherence between a set of signals from the large-scale brain activity signals across electrode pairs associated with a plurality of frequency bands.

4. The method of claim 2, wherein the extracting neural signal features from the large-scale brain activity signals is by measuring a set of power factors associated with a plurality of signals from the large-scale brain activity signals across electrodes associated with a plurality of different frequency bands.

5. The method of claim 2, wherein the extracting the neural signal features from the large-scale brain activity signals is by selecting from a set including one or more signal attributes having a function of power, a function of coherence, phase, phase-amplitude coupling, waveform, and waveform transform associated with a particular signal.

6. The method of claim 2, wherein at least one of the identifying the predictive network, the modeling the brain activity model, and the decoding the mood state or the neuropsychiatric state includes aggregating information from a set of multiple recording channels associated with a plurality of frequency bands and the extracted neural signal features.

7. The method of claim 1, wherein the decoding further comprises estimating low-dimensional neural states from at least one signal from the predictive network by filtering, wherein the filtering includes one of a Kalman filtering or another filtering using state system parameters derived from the at least one predictive brain activity signal by the brain activity model.

8. The method of claim 7, wherein the decoding comprises executing a regression algorithm on the estimated low-dimensional neural states using regression parameters for the brain activity model, wherein the brain activity model includes a regression model.

9. The method of claim 8, wherein the modeling the brain activity model further comprises fitting the regression model based on the estimated low-dimensional neural states and at least one of the independently derived measures of the mood state or the neuropsychiatric state, the independently derived measures of the mood state or the neuropsychiatric state including at least one of a measure of behavior, psychology, physiology, self-reports, facial tracking, audio tracking and speech recognition.

10. The method of claim 1, wherein the identifying the predictive network further comprises identifying the predictive network at least in part by comparing sensitivity and error of competing regression models.

11. The method of claim 1, wherein the large-scale brain activity signals are collected by a multisite electrode array.

12. The method of claim 1, wherein the large-scale brain activity signals are collected by a single-site electrode array.

13. The method of claim 1, wherein the modeling the brain activity model further comprises fitting a regression model based on at least one signal from the predictive network and at least one of a measure of behavior, psychology, physiology, self-reports, facial tracking, audio tracking and speech recognition, or biometric data associated with the at least one of the mood state or the neuropsychiatric state.

14. The method of claim 1, wherein the predictive network includes zero or more brain activity signals from the large-scale brain activity signals.

15. An apparatus for decoding mood or neuropsychiatric states from large-scale brain activity signals, comprising one or more processors coupled to a memory, the memory holding program instructions that when executed by the one or more processors causes the apparatus to:
receive, by the one or more processors, large-scale brain activity signals from an electrode assembly adapted to be coupled to a subject;
receive, by the one or more processors, independently derived measures of a mood state or a neuropsychiatric state;
identify, by the one or more processors, a predictive network from the large-scale brain activity signals based on the independently derived measures of the mood state or the neuropsychiatric state, wherein the predictive network comprises brain activity signals predictive of one of the mood state or the neuropsychiatric state;
responsive to the predictive network including at least one predictive brain activity signal, the one or more processors is configured to perform the steps of:
model a brain activity model from the at least one predictive brain activity signal;
decode through the brain activity model, the mood state or the neuropsychiatric state of the subject from the at least one predictive brain activity signal; and
provide a signal indicative of the decoded mood state or the decoded neuropsychiatric state, based on the decoding.

16. The apparatus of claim 15, further comprising means for sensing neurophysiological signals collected from large-scale brain regions, including an electrode array configured for sensing neurophysiological signals collected from large-scale brain regions, coupled to the one or more processors.

17. A method for enabling decoding of mood or neuropsychiatric state from large-scale brain activity signals using a state space brain activity model that estimates a subject's mood or neuropsychiatric state from neurophysiological signal data, the method comprising:
receiving, by one or more computers, independently derived measures of a mood state or a neuropsychiatric state, and neurophysiological signal data;
selecting, by the one or more computers, a predictive network from the large-scale brain activity signals that are received from a large-scale electrode network coupled to a brain of a subject by a progressive region selection technique based on the independently derived measures, wherein the predictive network comprises brain activity signals predictive of one of the mood state or the neuropsychiatric state;
responsive to the predictive network including at least one predictive brain activity signal, the one or more computers is configured to perform the steps of:
fitting the state space brain activity model to the at least one predictive brain activity signal from the predictive network and to the independently derived measures of the mood state or the neuropsychiatric state using a machine learning solution resulting in a brain activity model that estimates a brain state indicator of the mood state or the neuropsychiatric state;
regressing the brain state indicator or at least one neurophysiological signal feature from the neurophysiological signal data to at least one of the independently derived measures of the mood state or the neuropsychiatric state; and
automatically selecting regression parameters that minimize error and sensitivity of a regression model in decoding of the mood state or the neuropsychiatric state.

18. The method of claim 17, wherein the state space brain activity model is a linear state-space model (LSSM).

19. The method of claim 18, wherein the linear state-space model (LSSM) is used to analytically calculate at least one time-scale of predictive neural dynamics for decoding the mood state or the neuropsychiatric state.

20. The method of claim 17, wherein the independently derived measures of the mood state or the neuropsychiatric state are associated with behavioral, psychological, and physiological measurements and comprise at least one of a subject survey or a measure derived automatically from biometric data collected from the subject exclusive of any data from the large-scale electrode network.

21. The method of claim 17, further comprising recording in a computer-readable medium a definition of the selected predictive network, a set of state space model parameters, and the regression parameters for use in decoding the mood state or the neuropsychiatric state from large-scale brain activity of the subject.

22. The method of claim 17, wherein the large-scale electrode network comprises a multisite electrode array.

23. The method of claim 17, wherein the large-scale electrode network comprises a single-site electrode array.

24. The method of claim 17, wherein the neurophysiological signal data comprises at least one of electroencephalogram (EEG) data, intracranial neural recording data, electrocorticogram (ECoG) data, local field potential data, or spike firing rates data.

25. An apparatus for enabling decoding of mood or neuropsychiatric state from large-scale brain activity signals, comprising one or more processors coupled to a memory, the memory holding program instructions that when executed by the one or more processors causes the apparatus to:
receive independently derived measures of a mood state or a neuropsychiatric state;
select a predictive network from the large-scale brain activity signals that are received from a large-scale electrode network adaptable to be coupled to a brain of a subject by a progressive region selection technique based on the independently derived measures of the mood state or the neuropsychiatric state, wherein the predictive network comprises brain activity signals predictive of the mood state or the neuropsychiatric state;
responsive to the predictive network including at least one predictive brain activity signal, the one or more processors is configured to perform the steps of:
fit a state space brain activity model to a feature set including at least one signal from the predictive network and the independently derived measures of the mood state or the neuropsychiatric state using a machine learning solution resulting in a brain activity model that estimates a brain state indicator of the mood state or the neuropsychiatric state;
regress the brain state indicator or the at least one signal from the predictive network to at least one of the independently derived measures of the mood state or the neuropsychiatric state; and automatically select regression parameters that minimize error and sensitivity of a regression model in decoding of the mood state or the neuropsychiatric state.

26. The apparatus of claim 25, further comprising an electrode array configured for sensing neurophysiological signals collected from large-scale brain regions, coupled to the one or more processors.

27. A method for adaptive tracking of large-scale brain network activity, comprising:
characterizing, by one or more computers, a time-variant linear state-space model predictive of a brain state including a mood state or other neuropsychiatric state, at least in part by updating estimates of time-varying covariance matrices at time steps, including weighting recent large-scale brain network activity data more heavily than less recent large-scale brain network activity data;
tracking large-scale brain network activity received from an electrode assembly that is coupled to the one or more computers that collect the brain network activity data; and
estimating, by the one or more computers coupled to the electrode assembly, the brain state based on the time-variant linear state-space model and the brain network activity data.

28. The method of claim 27, wherein the brain network activity data comprises neurophysiological signal data for a subject collected over a period to include detectable time-variance for correlation of the brain state to brain network activity.

29. The method of claim 28, wherein the neurophysiological signal data comprises at least one of electroencephalogram (EEG) data, intracranial neural recording data electrocorticogram (ECoG) data, local field potential data, or spike firing rates data.

30. The method of claim 28, further comprising collecting the neurophysiological signal data using electrodes covering large-scale brain regions.

31. The method of claim 28, wherein the characterizing further comprises deriving at least one signal feature from the neurophysiological signal data.

32. The method of claim 31, wherein the deriving comprises removing noise by common average referencing.

33. The method of claim 31, wherein the deriving comprises dividing the neurophysiological signal data into time delimited windows.

34. The method of claim 33, wherein the deriving further comprises estimating a power spectral density associated with the neurophysiological signal data of each time delimited window.

35. The method of claim 31, wherein deriving the at least one signal feature further comprises at least one of calculating a power characteristic of multiple frequency bands thereby obtaining a high-dimensional power characteristic time series, or calculating a coherence between neurophysiological signal data across multiple pairs of electrodes.

36. The method of claim 31, wherein the at least one signal feature is selected from the group consisting of: phase, power, log power or other function of power, coherence or a function of coherence, phase-amplitude coupling, or any combination of the foregoing.

37. The method of claim 27, wherein characterizing the time-variant linear state-space model comprises recalculating QR-decomposition at every time step.

38. The method of claim 27, wherein the electrode assembly is a multisite array comprising multiple electrodes.

39. The method of claim 27, wherein the electrode assembly is a single-site array.

40. An apparatus for adaptive tracking of large-scale brain network activity, comprising one or more processors coupled to a memory, the memory holding program instructions that when executed by the one or more processors causes the apparatus to:
characterize, by the one or more processors, a time-variant linear state-space model predictive of a brain state including a mood state or a neuropsychiatric state, at least in part by updating estimates of time-varying covariance matrices at time steps, including weighting recent large-scale brain network activity data more heavily than less recent large-scale brain network activity data;
track large-scale brain network activity in a subject received from an electrode assembly coupled to the one or more processors that collect the brain network activity data; and
estimate, by the one or more processors coupled to the electrode assembly, the brain state based on the time-variant linear state-space model and the brain network activity data.

41. The apparatus of claim 40, further comprising the electrode assembly configured for sensing neurophysiological signals collected from large-scale brain regions, coupled to the one or more processors.

* * * * *